US012400355B2

(12) United States Patent
Dorman

(10) Patent No.: US 12,400,355 B2
(45) Date of Patent: Aug. 26, 2025

(54) SYSTEMS AND METHODS FOR ARTIFICIAL INTELLIGENCE BASED IMAGE ANALYSIS FOR PLACEMENT OF SURGICAL APPLIANCE

(71) Applicant: Circinus Medical Technology LLC, Concord, MA (US)

(72) Inventor: John Kyle Dorman, Midland, TX (US)

(73) Assignee: Circinus Medical Technology LLC, Concord, MA (US)

( * ) Notice: Subject to any disclaimer, the term of this patent is extended or adjusted under 35 U.S.C. 154(b) by 296 days.

(21) Appl. No.: 17/530,311

(22) Filed: Nov. 18, 2021

(65) Prior Publication Data

US 2022/0237817 A1    Jul. 28, 2022

Related U.S. Application Data

(60) Provisional application No. 63/115,992, filed on Nov. 19, 2020.

(51) Int. Cl.
*G06T 7/73* (2017.01)

(52) U.S. Cl.
CPC ...... *G06T 7/73* (2017.01); *G06T 2207/20084* (2013.01)

(58) Field of Classification Search
None
See application file for complete search history.

(56) References Cited

U.S. PATENT DOCUMENTS

D323,504 S    1/1992  Langton
5,143,076 A    9/1992  Hardy et al.
(Continued)

FOREIGN PATENT DOCUMENTS

CN    101198958 A    6/2008
CN    101528122 A    9/2009
(Continued)

OTHER PUBLICATIONS

Harrison, Peter. âSimpler Line Follower Sensors.â Micromouse Online, Apr. 15, 2011, https://web.archive.org/web/20120422001123/https://micromouseonline.com/2011/04/15/simpler-line-follower-sensors/. (Year: 2011).*
(Continued)

*Primary Examiner* — Matthew C Bella
*Assistant Examiner* — Johnny B Duong
(74) *Attorney, Agent, or Firm* — Foley & Lardner LLP

(57) ABSTRACT

Systems and methods for artificial intelligence based, such as machine learning-based, image analysis and suggestion of optimal or desired placement of surgical appliances and/or medical alignment devices, with, in certain implementations, supervised learning provided by users. A computing device may receive a target image captured via an image sensor; process the captured target image to identify anatomical features within the captured target image; calculate, via a trained neural network or artificial intelligence algorithm, a placement orientation and position of a virtual surgical appliance and/or desired item within the identified anatomical features; and render, on a display screen, the captured target image and the virtual surgical appliance and/or desired item at the calculated placement orientation and position.

16 Claims, 35 Drawing Sheets

(56) References Cited

U.S. PATENT DOCUMENTS

| | | | |
|---|---|---|---|
| 5,603,318 | A | 2/1997 | Heilbrun et al. |
| 5,824,085 | A | 10/1998 | Sahay et al. |
| 5,880,976 | A | 3/1999 | DiGioia, III et al. |
| 6,129,670 | A | 10/2000 | Burdette et al. |
| 6,139,544 | A | 10/2000 | Mikus et al. |
| 6,246,474 | B1 | 6/2001 | Cerni et al. |
| 6,511,236 | B1 | 1/2003 | Webjorn et al. |
| 6,638,281 | B2 | 10/2003 | Gorek |
| RE40,176 | E | 3/2008 | Peshkin et al. |
| 7,611,522 | B2 | 11/2009 | Gorek |
| 8,086,077 | B2 | 12/2011 | Eichhorn |
| 8,442,621 | B2 | 5/2013 | Gorek et al. |
| 9,038,971 | B1 | 5/2015 | Guthrie |
| 9,119,572 | B2 | 9/2015 | Gorek et al. |
| 9,216,048 | B2 | 12/2015 | Markey et al. |
| D772,859 | S | 11/2016 | Alesi et al. |
| 9,585,700 | B2 | 3/2017 | Wehrle et al. |
| 9,687,306 | B2 | 6/2017 | Markey et al. |
| 9,975,497 | B2 | 5/2018 | Kim |
| 10,064,687 | B2 | 9/2018 | Haimerl et al. |
| 10,123,840 | B2 | 11/2018 | Dorman |
| 10,342,619 | B2 | 7/2019 | Bracke et al. |
| 10,561,466 | B2 | 2/2020 | Hedblom et al. |
| 10,602,114 | B2 | 3/2020 | Casas |
| 10,603,116 | B2 | 3/2020 | Markey et al. |
| 10,864,023 | B2 | 12/2020 | Pak et al. |
| 10,908,771 | B2 * | 2/2021 | Berquam ............ G06F 3/04815 |
| 11,000,335 | B2 | 5/2021 | Dorman |
| 11,191,592 | B2 | 12/2021 | Gorek et al. |
| 11,484,381 | B2 | 11/2022 | Pak et al. |
| 11,826,111 | B2 * | 11/2023 | Mahfouz ................ G06T 19/20 |
| 11,832,886 | B2 | 12/2023 | Dorman |
| 12,096,993 | B2 * | 9/2024 | Toporek ................ G06N 3/084 |
| 2002/0035323 | A1 | 3/2002 | Saha et al. |
| 2002/0077540 | A1 | 6/2002 | Kienzle, III |
| 2002/0120252 | A1 | 8/2002 | Brock et al. |
| 2002/0140694 | A1 | 10/2002 | Sauer et al. |
| 2003/0181919 | A1 | 9/2003 | Gorek |
| 2003/0199882 | A1 | 10/2003 | Gorek |
| 2003/0236548 | A1 | 12/2003 | Hovanes et al. |
| 2004/0068187 | A1 | 4/2004 | Krause et al. |
| 2005/0113846 | A1 | 5/2005 | Carson |
| 2005/0192575 | A1 | 9/2005 | Pacheco |
| 2005/0236545 | A1 | 10/2005 | Seil et al. |
| 2006/0004322 | A1 | 1/2006 | Uesugi et al. |
| 2007/0262223 | A1 | 11/2007 | Wang et al. |
| 2007/0276397 | A1 | 11/2007 | Tacheco |
| 2008/0057889 | A1 | 3/2008 | Jan |
| 2008/0086160 | A1 | 4/2008 | Mastri et al. |
| 2008/0200927 | A1 | 8/2008 | Hartmann et al. |
| 2009/0090757 | A1 | 4/2009 | Kim et al. |
| 2009/0157083 | A1 | 6/2009 | Park et al. |
| 2009/0163901 | A1 | 6/2009 | Fisher et al. |
| 2009/0270868 | A1 | 10/2009 | Park et al. |
| 2009/0292201 | A1 | 11/2009 | Kruecker |
| 2009/0292279 | A1 | 11/2009 | Bliweis et al. |
| 2009/0311655 | A1 | 12/2009 | Karkanias et al. |
| 2010/0100081 | A1 | 4/2010 | Tuma et al. |
| 2010/0153081 | A1 | 6/2010 | Bellettre et al. |
| 2010/0198402 | A1 | 8/2010 | Greer et al. |
| 2010/0210939 | A1 | 8/2010 | Hartmann et al. |
| 2010/0274256 | A1 | 10/2010 | Ritchey et al. |
| 2011/0098721 | A1 | 4/2011 | Tran et al. |
| 2011/0214279 | A1 | 9/2011 | Park et al. |
| 2011/0268248 | A1 | 11/2011 | Simon et al. |
| 2012/0116203 | A1 | 5/2012 | Vancraen et al. |
| 2012/0150243 | A9 | 6/2012 | Crawford et al. |
| 2012/0232834 | A1 | 9/2012 | Roche et al. |
| 2012/0319859 | A1 | 12/2012 | Taub et al. |
| 2013/0060146 | A1 | 3/2013 | Yang et al. |
| 2013/0085344 | A1 | 4/2013 | Merkl et al. |
| 2013/0095855 | A1 | 4/2013 | Bort |
| 2013/0114866 | A1 | 5/2013 | Kasodekar et al. |
| 2013/0245461 | A1 | 9/2013 | Maier-Hein et al. |
| 2013/0253599 | A1 | 9/2013 | Gorek et al. |
| 2014/0148808 | A1 | 5/2014 | Inkpen et al. |
| 2015/0010220 | A1 | 1/2015 | Teichman et al. |
| 2016/0022374 | A1 | 1/2016 | Haider et al. |
| 2016/0106202 | A1 | 4/2016 | Ford |
| 2016/0235481 | A1 | 8/2016 | Dorman |
| 2016/0250040 | A1 | 9/2016 | Hermle et al. |
| 2016/0324580 | A1 | 11/2016 | Esterberg |
| 2016/0373647 | A1 | 12/2016 | Morate et al. |
| 2017/0007328 | A1 | 1/2017 | Cattin et al. |
| 2017/0027651 | A1 | 2/2017 | Esterberg |
| 2017/0035517 | A1 | 2/2017 | Geri et al. |
| 2017/0071673 | A1 | 3/2017 | Ferro et al. |
| 2017/0135706 | A1 | 5/2017 | Frey et al. |
| 2017/0172696 | A1 | 6/2017 | Saget et al. |
| 2017/0202633 | A1 | 7/2017 | Liu |
| 2017/0221244 | A1 | 8/2017 | Hiraga et al. |
| 2017/0245947 | A1 | 8/2017 | Bozung et al. |
| 2017/0304011 | A1 | 10/2017 | Markey et al. |
| 2017/0333134 | A1 | 11/2017 | Wollowick et al. |
| 2017/0367771 | A1 | 12/2017 | Tako et al. |
| 2018/0000380 | A1 | 1/2018 | Stein et al. |
| 2018/0008358 | A1 | 1/2018 | Kostrzewski et al. |
| 2018/0092699 | A1 | 4/2018 | Finley et al. |
| 2018/0140362 | A1 | 5/2018 | Cal et al. |
| 2018/0303559 | A1 | 10/2018 | Shepherd et al. |
| 2018/0310956 | A1 | 11/2018 | Polster |
| 2018/0325618 | A1 | 11/2018 | Justin et al. |
| 2019/0029757 | A1 | 1/2019 | Roh et al. |
| 2019/0046278 | A1 | 2/2019 | Steinle et al. |
| 2019/0060000 | A1 | 2/2019 | Dorman |
| 2019/0090959 | A1 | 3/2019 | Haider et al. |
| 2019/0223962 | A1 | 7/2019 | Roldan et al. |
| 2019/0254754 | A1 | 8/2019 | Johnson et al. |
| 2019/0336179 | A1 | 11/2019 | Pak et al. |
| 2019/0357809 | A1 | 11/2019 | Borja |
| 2019/0388173 | A1 | 12/2019 | Pak et al. |
| 2020/0051274 | A1 | 2/2020 | Siemionow et al. |
| 2020/0111213 | A1 | 4/2020 | Chacon et al. |
| 2020/0197191 | A1 | 6/2020 | Akhlaghpour et al. |
| 2020/0229869 | A1 | 7/2020 | Dorman |
| 2020/0305985 | A1 | 10/2020 | Tolkowsky |
| 2021/0038340 | A1 | 2/2021 | Itkowitz et al. |
| 2021/0100536 | A1 | 4/2021 | Spindle |
| 2021/0186617 | A1 | 6/2021 | Gorek et al. |
| 2021/0228279 | A1 | 7/2021 | Dorman |
| 2022/0192756 | A1 | 6/2022 | Dorman |
| 2022/0201199 | A1 | 6/2022 | Dorman |
| 2022/0241018 | A1 | 8/2022 | Dorman |
| 2022/0351410 | A1 * | 11/2022 | Siemionow ............ A61B 34/10 |
| 2023/0036038 | A1 | 2/2023 | Finley et al. |
| 2023/0054394 | A1 | 2/2023 | Luo et al. |
| 2023/0131831 | A1 | 4/2023 | Dorman |
| 2023/0172631 | A1 | 6/2023 | Richter et al. |
| 2023/0346481 | A1 | 11/2023 | Dorman |

FOREIGN PATENT DOCUMENTS

| | | |
|---|---|---|
| CN | 101721231 A | 6/2010 |
| CN | 101984931 A | 3/2011 |
| CN | 103519895 A | 1/2014 |
| EP | 2 901 957 A1 | 8/2015 |
| KR | 101478522 B1 | 1/2015 |
| KR | 101901521 B1 | 9/2018 |
| WO | WO-2013/020026 | 2/2013 |
| WO | WO-2014/025305 A1 | 2/2014 |
| WO | WO-2014/063181 A1 | 5/2014 |
| WO | WO-2015/168781 | 11/2015 |
| WO | WO-2016/007936 | 1/2016 |
| WO | WO-2016/131016 A2 | 8/2016 |
| WO | WO-2017/167799 A1 | 10/2017 |
| WO | WO-2018/200767 A1 | 11/2018 |
| WO | WO-2019/036524 A1 | 2/2019 |
| WO | WO-2020/105049 A1 | 5/2020 |
| WO | WO-2020/214645 A1 | 10/2020 |
| WO | WO-2020/214744 A1 | 10/2020 |

(56) References Cited

FOREIGN PATENT DOCUMENTS

| WO | WO-2020/216934 A1 | 10/2020 |
|---|---|---|
| WO | WO-2022/109185 A1 | 5/2022 |

OTHER PUBLICATIONS

Harrison, Peter. "Simpler Line Follower Sensors." Micromouse Online, Apr. 15, 2011, https://web.archive.org/web/20120422001123/https://micromouseonline.com/2011/04/15/simpler-line-follower-sensors/. (Year: 2011).*

NumPy—Data Types. https://web.archive.org/web/20181126133733/https://www.tutorialspoint.com/numpy/numpy_data_types.htm. 2018 (Year: 2018).*

Harrison, Peter. "Simpler Line Follower Sensors." Micromouse Online, 15 Apr. 2011, https://web.archive.org/web/20120422001123/https://micromouseonline.com/2011/04/15/simpler-line-follower-sensors/. (Year: 2011).*

Herold, Maternus. Using Deep Convolutional Networks to Regress a C-arm's Position from a single X-ray Image. Diss. 2020. (Year: 2020).*

Wells, Gordon, Christophe Venaille, and Carme Torras. "Vision-based robot positioning using neural networks." Image and vision computing 14.10 (1996): 715-732. (Year: 1996).*

Elmi-Terander, Adrian, et al. "Surgical navigation technology based on augmented reality and integrated 3D intraoperative imaging: a spine cadaveric feasibility and accuracy study." Spine 41.21 (2016): E1303-E1311. (Year: 2016).*

International Search Report and Written Opinion for International Patent Application PCT/US2022/024683 dated Jun. 21, 2022.

Foreign Search Report on PCT PCT/US2021/059965 dated Feb. 3, 2022.

International Patent Appl. No. PCT/US2022/022204, International Search Report and Written Opinion dated Jun. 10, 2022, 18 pgs.

Julian Horsey, "Ozaki iCoat Finger Case Makes Draw Something Even More Fun", Apr. 20, 2012, pp. 1-11, XP093028330, Retrieved from the Internet: URL:https://www.geeky-gadgets.com/ozaki-icoat-finger-case-makes-draw-someting-even-more-fun-20-4-2012/ [retrieved on Mar. 2, 2023].

International Search Report and Written Opinion on PCT/US2022/047306 Dated Mar. 28, 2023.

U.S. Appl. No. 18/513,155, filed Nov. 17, 2023, Circinus Medical Technology LLC.

U.S. Appl. No. 18/553,025, filed Sep. 28, 2023, Circinus Medical Technology LLC.

U.S. Appl. No. 18/554,969, filed Oct. 11, 2023, Circinus Medical Technology LLC.

U.S. Appl. No. 16/639,107, filed Feb. 13, 2020, System and Method Using Augmented Reality With Shape Alignment for Medical Device Placement.

U.S. Appl. No. 17/604,359, filed Oct. 15, 2021, Attachment Apparatus to Secure a Medical Alignment Device to Align a Tool.

U.S. Appl. No. 17/604,362, filed Oct. 15, 2021, Orientation Calibration System for Image Capture.

U.S. Appl. No. 17/591,478, filed Feb. 2, 2022, Systems and Methods for Simulating Three-Dimensional Orientations of Surgical Hardware Devices About an Inseration Point of an Anatomy.

U.S. Appl. No. 18/553,025, filed Sep. 28, 2023, System and Method for Simulating an Orientation of a Medical Device at an Insertion Point.

U.S. Appl. No. 17/970,378, filed Oct. 20, 2022, Attachment Apparatus to Secure a Medical Alignment Device to Align a Tool.

U.S. Appl. No. 18/350,672, filed Jul. 11, 2023, System and Method for Medical Device Placement.

U.S. Appl. No. 18/554,969, filed Oct. 11, 2023, System and Method for Lidar-Based Anatomical Mapping.

International Pat. Appl. No. PCT/US2020/028220, International Search Report and Written Opinion, dated Aug. 14, 2020, 22 pgs.

International Pat. Appl. No. PCT/US2020/028375, International Search Report and Written Opinion dated Jul. 21, 2020, 10 pgs.

International Search Report and Written Opinion in corresponding international application No. PCT/US2016/017897, mailed Aug. 24, 2016, 13 pages.

International Search Report and Written Opinion in PCT/US18/46786, dated Dec. 13, 2018, 10 pgs.

International Search Report and Written Opinion issued in PCT/US2022/014988 DTD Apr. 6, 2022, 17 pages.

Merloz et al., "Pedicle Screw Placement Using Image Guided Techniques." Clinical Orthopaedics and Related Research, No. 354, pp. 39-48, 1998, entire document [online] URL=<https://journals.lww.com/clinorthop/Fulltext/1998/09000/Pedicle_Screw_Placement_Using_Image_Guided.6.aspx>.

Supplementary Partial European Search Report corresponding to EP 18846995.1 dated Jun. 11, 2021, 4 pages.

Crescendo CR-30 phone holder. Amazon datasheet [online]. Crescendo, first available on Nov. 18, 2017. [Retrieved on Jun. 13, 2024]; Retrieved from the Internet. <URL: https://a.co/d/fyEOcbM>.

International Search Report and Written Opinion in PCT/US2024/041823 dated Jan. 13, 2025.

Extended European Search Report on EP 22788881.5 DTD Jan. 21, 2025 (12 pgs.).

U.S. Appl. No. 16/639,107, filed Feb. 13, 2020, System and Method Using Augmented Reality With Shape Alignment for Medical Device Placement in Bone.

U.S. Appl. No. 17/233,301, filed Apr. 16, 2021, System and Method for Medical Device Placement in Bone.

U.S. Appl. No. 17/591,478, filed Feb. 2, 2022, Systems and Methods for Simulating Three-Dimensional Orientations of Surgical Hardware Devices About an Insertion Point of an Anatomy.

* cited by examiner

SYSTEMS AND METHODS FOR ARTIFICIAL INTELLIGENCE BASED IMAGE ANALYSIS FOR PLACEMENT OF SURGICAL APPLIANCE

CROSS-REFERENCE TO RELATED APPLICATIONS

This application claims the benefit of and priority to U.S. Provisional Patent Application No. 63/115,992, filed Nov. 19, 2020, the contents of which are incorporated herein by reference in its entirety

TECHNICAL FIELD

The present disclosure is related to artificial intelligence based, such as machine learning-based, computer vision systems and methods. In particular, the present disclosure relates to systems and methods for capturing and analyzing photos for calculating and determining optimal or desired placement of surgical appliances, desired items, such as, for example, a posterior fixation placement.

BACKGROUND

When images are captured using an image capture device, such as a camera, the angle in which the image is captured may skew or alter critical details of the image. This could, for example, cause unintended consequences if such altered critical details are used in connection with images used for medical procedures or for diagnoses. For example, in connection with spinal fusion surgery, these patients may have pedicle screws placed into their vertebrae. The pedicle screws are typically implanted into the vertebrae through the pedicles of the vertebrae. A pilot hole may be created through the cortex of the bone to create the path or tract through which the pedicle screw will be placed. Placing the pedicle screw at the correct angle helps to ensure a mechanically sound construct and to avoid injury to surrounding structures such as the spinal cord, nerve roots, and blood vessels. The orientation of the pedicle screw can be described by a three-dimensional alignment angle or insertion angle, and the correct image capture of any diagnostic images used in determining such an alignment insertion angle needs to be properly and accurately performed.

Other situations in which having a true alignment and image capture of an object or the subject is important. Examples include construction, interior design, CAD drawings, and three-dimensional printing. Another example, as mentioned above, is a surgical navigation system in which having a true and accurate angle is a prerequisite for safe functioning. If the camera or image capture is held at an angle, in any plane, the resulting photo will not be truly orthogonal. Sometimes the problem may be corrected with image processing software in the post-processing phase provided the image has a straight line, or edge, but this cannot be guaranteed. Often times the subject of the image does not have a straight line or edge, like an axial CT for example. In this case, it is imperative that the camera, which can be an iPhone or iPod touch, be held orthogonal in all planes at the time the image is captured so as not to introduce skew and error.

SUMMARY

This summary is provided to introduce a selection of elements and aspects that are further described below in the detailed description. This summary is not intended to identify key or essential features of the claimed subject matter, nor is it intended to be used as an aid in limiting the scope of the claimed subject matter.

In a first general aspect, an orientation calibration system for image capture is provided that ensures that the camera of the device, which may be implemented on a smartphone, iPhone, iPod touch, or other electronic device, tablet, or tablet like device, captures an image while being orthogonal in all planes.

In one general aspect, an orientation calibration system for image capture is provided, and this may be implemented or referred to as a medical alignment device. The orientation calibration system may be configured to be oriented to capture a target image, which may be referred to as a reference image. The orientation calibration system may include a camera operable to capture a target image, a display screen configured to display the target image captured using the camera, and an orientation sensor configured to determine two (or three axes of rotation in certain other embodiments) of the orientation calibration system. The orientation calibration system may include one or more processors to determine a present orientation of the orientation calibration system using the orientation sensor, to display at least a portion of the present orientation of the orientation calibration system and a desired orientation of the orientation calibration system on the display screen, to receive a request to capture the target image, and to capture the target image using the camera in response to receiving the request to capture the target image, and when a difference between the present orientation of the orientation calibration system and the desired orientation of the orientation calibration system is within a threshold.

In another general aspect, an orientation calibration system for image capture is provided for use in aligning an image source that displays the target image. For example, the target image that is being captured is displayed on an external monitor having four sides with each adjacent side being orthogonal to one another, and the orientation calibration system includes a first side and a back side, and is configured to assist in aligning/orienting the external monitor in an orthogonal or desired orientation or position relative to the ground before the target image is captured by the orientation calibration system. The one or more processors of the orientation calibration system may be configured to display a left/right graphical indicator when the first side of the orientation calibration system is positioned along a side edge of the external monitor to display an indication from the orientation sensor of the present left/right orientation of the orientation calibration system and a desired left/right orientation of the external monitor, wherein the left/right graphical indicator changes as the left/right orientation of the external monitor is adjusted while the first side of the orientation calibration system is positioned along the side edge of the external monitor and the present left/right orientation of the orientation calibration system changes. The one or more processors of the orientation calibration system may be further configured to display an up/down graphical indicator when the back side of the orientation calibration system is positioned along the front surface of the external monitor to display an indication from the orientation sensor of the present up/down orientation of the orientation calibration system and a desired up/down orientation of the external monitor, wherein the up/down graphical indicator changes as the up/down orientation of the external monitor is adjusted while the back side of the orientation calibration system is positioned along the front surface of the external monitor and the present up/down orientation of the orientation calibration system changes.

In one specific aspect, the display screen of the orientation calibration system may be further configured to display a graphical representation of the present orientation when the orientation calibration system is aligned or abutted with an imaging source providing the target image so as to place the imaging source at a desired orientation.

In another specific aspect, the indication or notification of the present orientation may be displayed on the display screen using a graphical element, which may be referred to as a dynamic graphical element showing a tilt of the medical alignment device along one, two, or, in some embodiments, three axis.

In some embodiments, the dynamic graphical element includes a circle movable in a curved track, wherein the circle changes color when the difference between the present orientation of the medical alignment device and the reference orientation of the medical alignment device is within the threshold.

In other embodiments, the processor of the orientation calibration system may be configured to capture the reference image upon receiving a command from a user in response to the circle changing color. In some other embodiments, the dynamic graphical element may include a circle movable in a track or a gauge about a center position of the track or gauge, and wherein a notification is generated when the circle is within a predetermined range of the center position.

In yet some other embodiments, the processor may be configured to capture the reference image upon receiving a command from a user in response to the circle reaching the predetermined range of the center position.

In some other embodiments, the processor may be configured to capture the reference image automatically in response to the circle reaching the predetermined range of the center position.

In certain other embodiments, the orientation calibration system may elicit notifications when certain alignment or orientation of the orientation calibration system are achieved, and these notifications may be any known or available visual, graphical, auditory, and/or tactile notifications.

In another specific aspect, the orientation sensor may include at least one of a gyroscope, an accelerometer, and an inertial measurement unit.

In another general aspect, a method is disclosed for orienting a system for capture of a target image. The method may include determining a present orientation of the system using an orientation sensor, displaying a graphical representation of at least a portion of the present orientation of the system on a display screen of the system, capturing the target image from an imaging source using a camera of the system when a difference between at least a portion of the present orientation of the system and a reference orientation of the system is within a threshold, and displaying the captured target image on the display screen.

In one specific aspect, the method further includes displaying a graphical representation of at least a portion of the reference orientation of the system on the display screen along with the at least a portion of the present orientation of the system that indicates a difference between the at least a portion of the reference orientation and the at least a portion of the present orientation.

In another specific aspect, the method further includes receiving a request to capture the target image. Another aspect may include that the image is not captured until after receiving the request to capture the target image, and after the difference between the at least the portion of the present orientation of the system and the reference orientation of the system is within the threshold.

In yet another aspect, the method further includes generating a notification when the difference between at least a portion of the present orientation of the system and the reference orientation of the system is within the threshold. Another aspect may include that the notification may include one or more from the group that includes a visual notification, an auditory notification, a tactile notification, and a change in color notification.

In yet another aspect, the method may include that the captured target image also includes at least a portion of a graphical representation of the difference between the at least a portion of the reference orientation and the at least a portion of the present orientation.

In yet another general aspect, a method is disclosed for using an orientation calibration system to align a display monitor in an orthogonal position relative to the ground, and the display monitor having four sides with each adjacent side being orthogonal to one another and configured to display a target image. The disclosed method may include positioning a first side of the orientation calibration system adjacent a first side of the display monitor, determining the alignment of the first side of the display monitor using the orientation calibration system, adjusting the alignment of the first side of the display monitor to ensure it is in an orthogonal position relative to the ground within an acceptable threshold as determined by the orientation calibration system, positioning a back side of the orientation calibration system adjacent a front surface of the display monitor, determining the alignment of the front surface of the display monitor using the orientation calibration system, and adjusting the alignment of the front surface of the display monitor to ensure it is in an orthogonal position relative to the ground within an acceptable threshold as determined by the orientation calibration system.

In one specific aspect of the method, the orientation calibration system displays a left/right graphical indicator when the first side of the orientation calibration system is positioned along the first side of the display monitor to display an indication of the present left/right orientation of the orientation calibration system and a desired left/right orientation of the display monitor, and the left/right graphical indicator changes as the left/right orientation of the display monitor is adjusted while the first side of the orientation calibration system is positioned along the first side of the display monitor and the present left/right orientation of the orientation calibration system changes. Further, the orientation calibration system may display an up/down graphical indicator when the back side of the orientation calibration system is positioned along the front surface of the display monitor to display an indication from the orientation sensor of the present up/down orientation of the orientation calibration system and a desired up/down orientation of the display monitor, and the up/down graphical indicator changes as the up/down orientation of the display monitor is adjusted while the back side of the system is positioned along the front surface of the display monitor and the present up/down orientation of the orientation calibration system changes.

In another specific aspect, the method further includes capturing the target or reference image from an imaging source when a difference between the present orientation of the medical alignment device and the reference orientation of the medical alignment device is within a threshold. In some embodiments, capturing the target image or reference image from the imaging source when a difference between the present orientation of the medical alignment device and the reference orientation of the medical alignment device is within a threshold is automatically executed.

In another general aspect, a system is disclosed for optimal or desired placement of surgical appliances or other items. The system includes a processor configured to: receive a target image captured via an image sensor; process the captured target image to identify anatomical features within the captured target image; calculate, via a trained neural network, a placement orientation and position of a virtual surgical appliance within the identified anatomical features; and render, on a display screen, the captured target image and the virtual surgical appliance or other item at the calculated placement orientation and position.

In a specific aspect, the system includes an orientation sensor configured to determine at least two axes of rotation of the orientation calibration system; and the processor is further configured to: ascertain a present orientation of the orientation calibration system using the orientation sensor, and render, on the display screen, at least a portion of the present orientation of the orientation calibration system and the virtual surgical appliance at the calculated orientation and position.

In another specific aspect, the processor is further configured to measure a bit depth of the captured target image. In still another specific aspect, the processor is further configured to identify a largest area of homogeneity within the captured target image. In a further aspect, the processor is further configured to identify at least one region adjacent to the identified largest area of homogeneity. In a still further aspect, the processor is further configured to calculate the placement orientation and position of the virtual surgical appliance within a first region of the identified at least one regions adjacent to the identified largest area of homogeneity.

In another specific aspect, the processor is further configured to calculate the placement orientation and position of the virtual surgical appliance according to a weighted average of historical placement orientations and positions of the virtual surgical appliance. In still another specific aspect, the processor is further configured to: receive a second target image captured via a second image sensor, the second target image orthogonal to the target image; and process the captured second target image to identify anatomical features within the captured second target image; and calculating the placement orientation and position of the virtual surgical appliance further includes calculating a three-dimensional orientation and position of the virtual surgical appliance within a region defined by the target image and the orthogonal second target image.

In still another specific aspect, the system includes a network interface configured to transmit the processed target image to a remote computing device executing the trained neural network; and the processor is further configured to receive, from the remote computing device, the calculated placement orientation and position of the virtual surgical appliance. In yet still another specific aspect, the anatomical features within the captured target image comprise a portion of a vertebra and the virtual surgical appliance is a virtual pedicle screw.

In another general aspect, disclosed is a method for optimal or desired placement of surgical appliances or other items. The method includes receiving, by a computing device, a target image captured via an image sensor; processing, by the computing device, the captured target image to identify anatomical features within the captured target image; calculating, by the computing device via a trained artificial intelligence system or neural network, a placement orientation and position of a virtual surgical appliance or other item within the identified anatomical features; and rendering, by the computing device on a display screen, the captured target image and the virtual surgical appliance at the calculated placement orientation and position.

In a specific aspect, the method includes ascertaining, by the computing device via an orientation sensor configured to determine at least two axes of rotation of the orientation calibration system, a present orientation of the orientation calibration system using the orientation sensor; and rendering, on the display screen, at least a portion of the present orientation of the orientation calibration system and the virtual surgical appliance at the calculated orientation and position.

In another specific aspect, the method includes measuring a bit depth of the captured target image. In yet another specific aspect, the method includes identifying a largest area of homogeneity within the captured target image. In a further aspect, the method includes identifying at least one region adjacent to the identified largest area of homogeneity. In a still further aspect, the method includes calculating the placement orientation and position of the virtual surgical appliance within a first region of the identified at least one regions adjacent to the identified largest area of homogeneity.

In another specific aspect, the method includes calculating the placement orientation and position of the virtual surgical appliance according to a weighted average of historical placement orientations and positions of the virtual surgical appliance.

In yet another specific aspect, the method includes receiving, by the computing device, a second target image captured via a second image sensor, the second target image orthogonal to the target image, and processing, by the computing device, the captured second target image to identify anatomical features within the captured second target image; and calculating the placement orientation and position of the virtual surgical appliance further comprises calculating a three-dimensional orientation and position of the virtual surgical appliance within a region defined by the target image and the orthogonal second target image.

In another specific aspect, the method includes transmitting, via a network interface of the computing device, the processed target image to a remote computing device executing the trained neural network; and receiving, from the remote computing device, the calculated placement orientation and position of the virtual surgical appliance. In yet another specific aspect, the anatomical features within the captured target image comprise a portion of a vertebra and the virtual surgical appliance is a virtual pedicle screw.

BRIEF DESCRIPTION OF THE DRAWINGS

For a more complete understanding of various embodiments of the present invention and the advantages thereof, reference is now made to the following brief description, taken in connection with the accompanying drawings, appendices, and detailed description, wherein like reference numerals represent like parts, and in which:

FIGS. 6A-6D illustrate example user interfaces for a computer-implemented program to perform the methods shown in FIGS. 5A-5D, wherein FIG. 6A illustrates an interface for selecting vertebra of a patient, FIG. 6B illustrates aligning the longitudinal axis of the apparatus with the sagittal plane, FIG. 6C illustrates defining a pedicle screw's position and its sagittal angle, and FIG. 6D illustrates generating an angle-indicative line for showing the angle between the longitudinal axis of the apparatus and the sagittal plane;

Like elements are indicated with like reference numerals.

DETAILED DESCRIPTION

Figure 1:
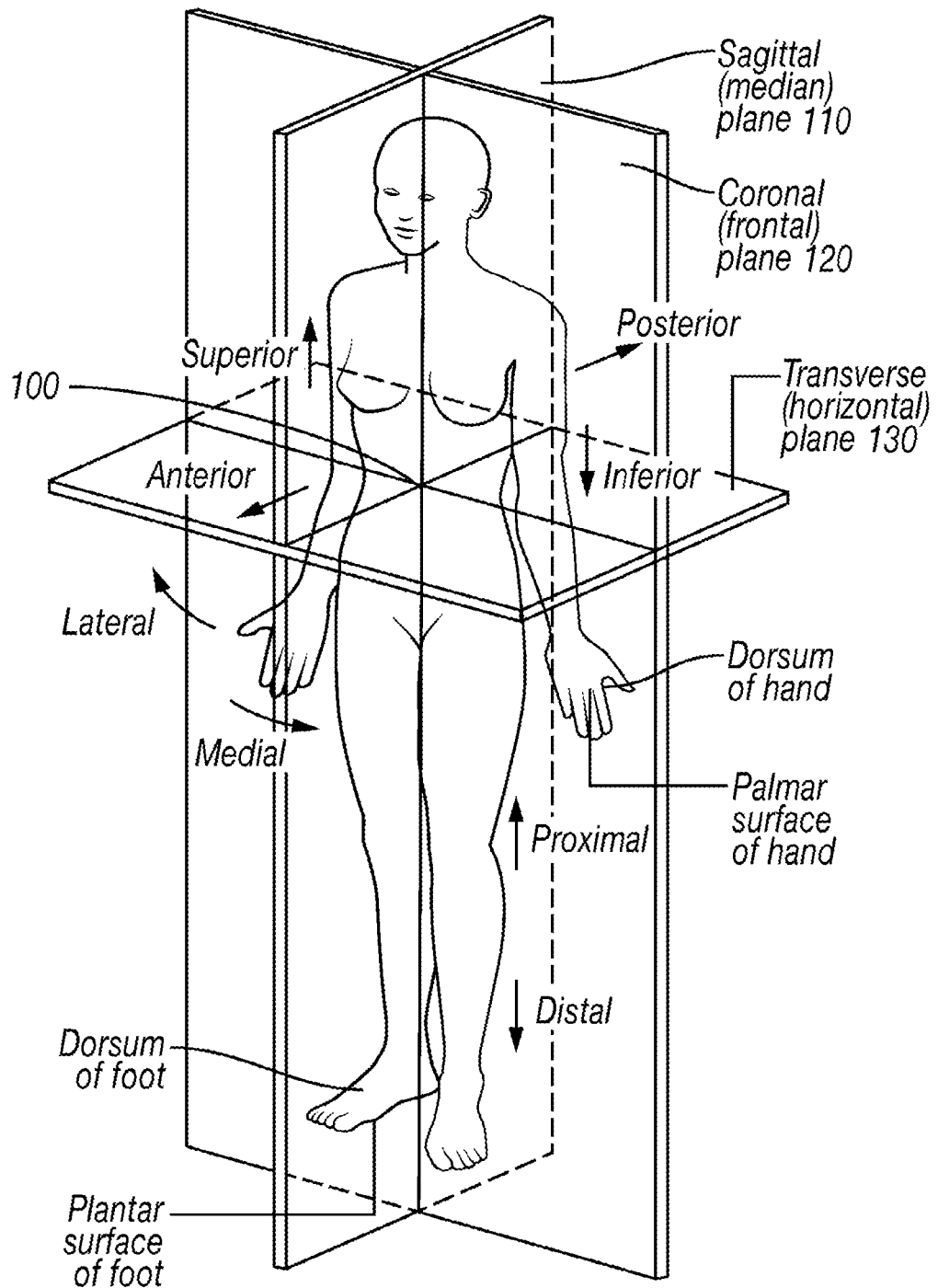
FIG. 1 illustrates definitions of a sagittal plane, a frontal plane, and a transverse plane relative to a patient's body.

For purposes of reading the description of the various embodiments below, the following descriptions of the sections of the specification and their respective contents may be helpful:

Section A describes orientation calibration systems and methods for image capture; and Section B describes systems and methods for capturing and analyzing photos for calculating and determining placement of posterior fixation placement. Although the placement of a posterior fixation device is illustrated herein, it should be understood that the present disclosure should not be limited to a posterior fixation device, but may be applicable to the placement or positioning of a surgical device, or any other device, at a desired location.

In the following detailed description and the attached drawings and appendices, numerous specific details are set forth to provide a thorough understanding of the present disclosure. However, those skilled in the art will appreciate that the present disclosure may be practiced, in some instances, without such specific details. In other instances, well-known elements have been illustrated in schematic or block diagram form in order not to obscure the present disclosure in unnecessary detail. Additionally, for the most part, specific details, and the like, have been omitted inasmuch as such details are not considered necessary to obtain a complete understanding of the present disclosure, and are considered to be within the understanding of persons of ordinary skill in the relevant art.

It is further noted that, unless indicated otherwise, all functions described herein may be performed in hardware or as software instructions for enabling a computer, radio or other device to perform predetermined operations, where the software instructions are embodied on a computer readable storage medium, such as RAM, a hard drive, flash memory or other type of computer readable storage medium known to a person of ordinary skill in the art. In certain embodiments, the predetermined operations of the computer, radio or other device are performed by a processor such as a computer or an electronic data processor in accordance with code such as computer program code, software, firmware, and, in some embodiments, integrated circuitry that is coded to perform such functions. Furthermore, it should be understood that various operations described herein as being performed by a user may be operations manually performed by the user, or may be automated processes performed either with or without instruction provided by the user.

A. Orientation Calibration Systems and Methods for Image Capture

This disclosure describes an orientation calibration system for capturing a target image (also referred to as a reference image) and ensuring that the captured image is accurately captured, as well as methods of using and achieving the same. The orientation calibration system is illustrated herein in connection with FIGS. 1-18 as a medical alignment device operable to align a medical tool to a desired orientation relative to a patient (and a body part thereof). Although the current disclosure primarily describes orientation calibration system in connection with medical and diagnostic image applications, the orientation calibration system and related methods should not be understood to be limited to only medical type applications. On the contrary, such an orientation calibration system and related methods may be used for any of a variety of applications including, without limitation, for accurately capturing images at correct orientations, alignments, or angles for CAD drawings, construction drawings, maps, geology maps and formations, interior design, surgical navigation systems, three-dimensional printing applications, and the like.

The orientation calibration system enables an accurate measurement of relative orientation between the medical alignment device and the patient. For example, the medical alignment device simulates an insertion angle relative to a reference image, such as a CT scan or other scan of a bone of the patient. The orientation calibration avoids a mistaken reading of the relative angle as measured by the orientation sensor between the medical alignment device and the reference image, and thus enabling accurate subsequent alignment indications.

At a high level, the orientation calibration system is applicable to both the medical alignment device and an image provider, such as a display monitor showing or displaying a target image, such as a diagnostic image such as a CT or MRI scan. In one embodiment, the medical alignment device includes a display and an orientation sensor. The display shows a present orientation of the medical alignment device relative to a known reference frame, such as to a reference orientation. The reference orientation may be determined by aligning to a gravitational direction or the image provider, such as the monitor displaying an image. For example, the medical alignment device may be positioned and aligned to the image provider in the same plane. When capturing a copy of the reference image shown in the image provider, the medical alignment device can be oriented to be parallel to the image provider and have one longitudinal axis aligned with the gravitational direction (or forming a known angle relative to the gravitational direction). As such, the calibration enables the medical alignment device to ascertain subsequent increments of orientation to provide accurate readings.

FIG. 1 illustrates a sagittal or median plane 110, a frontal or coronal plane 120, and a horizontal or transverse plane 130 relative to a patient's body part 100 located at the intersection of the sagittal plane 110, the coronal plane 120, and the transverse plane 130. Each plane is orthogonal to each other such that if the position or orientation of an object, device, or medical hardware, such as a pedicle screw, is known in two of the orthogonal planes, the three-dimensional orientation angle of such item may be calculated or known. When discussing a vertebra (or other body parts) in the following disclosure, reference is made to the sagittal plane, coronal plane, and transverse plane. It should be understood that, when these planes are mentioned, they are not intended as a reference only to the specific sagittal, coronal, and transverse planes illustrated in FIG. 1, but rather, are intended as a reference to illustrate an orientation or location relative to the specific vertebra or body part being discussed.

Figure 2A:
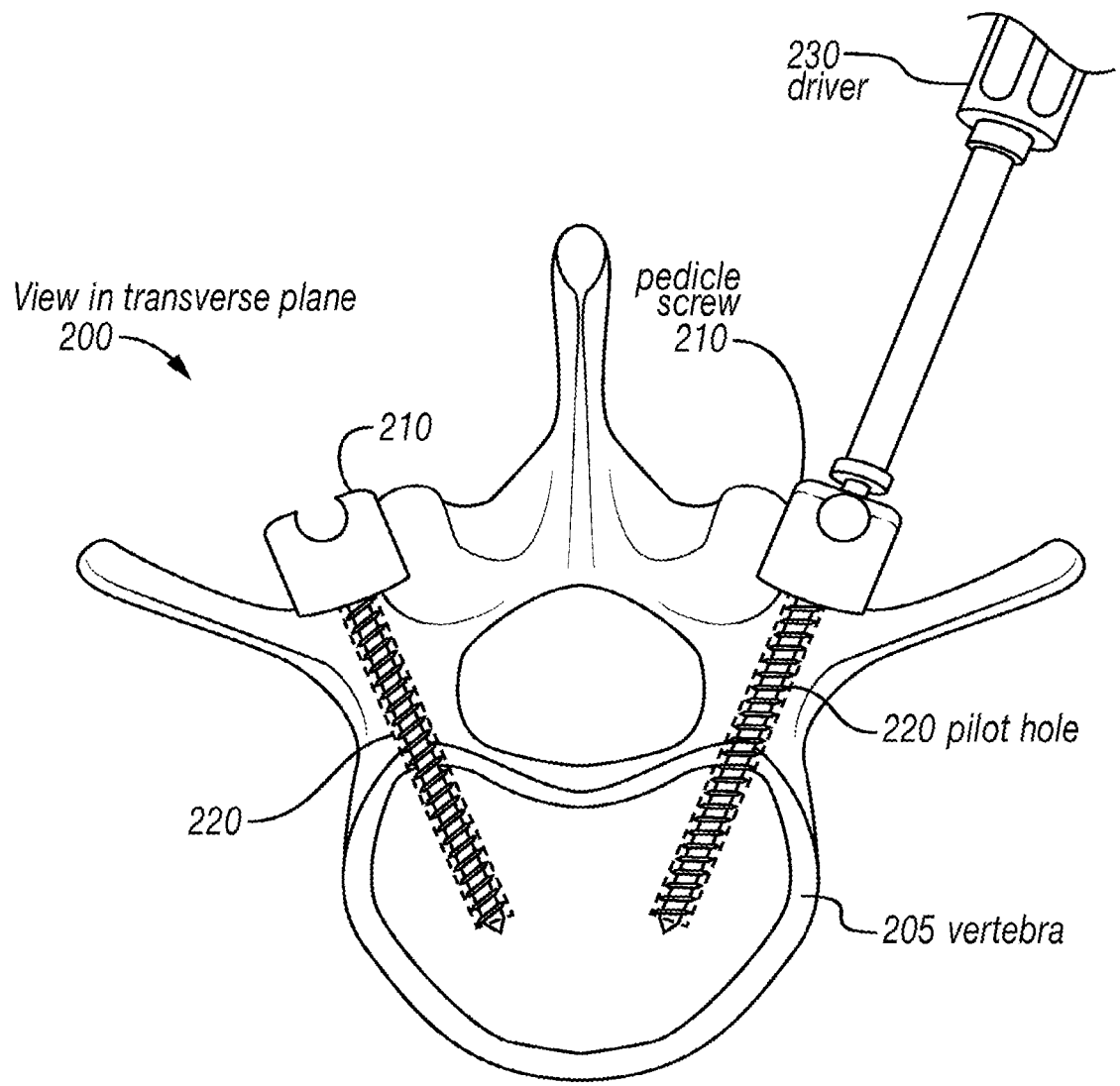
FIG. 2A illustrates a cross-sectional, axial view of a vertebra having pedicle screws installed in respective pilot holes.
Figure 2B:
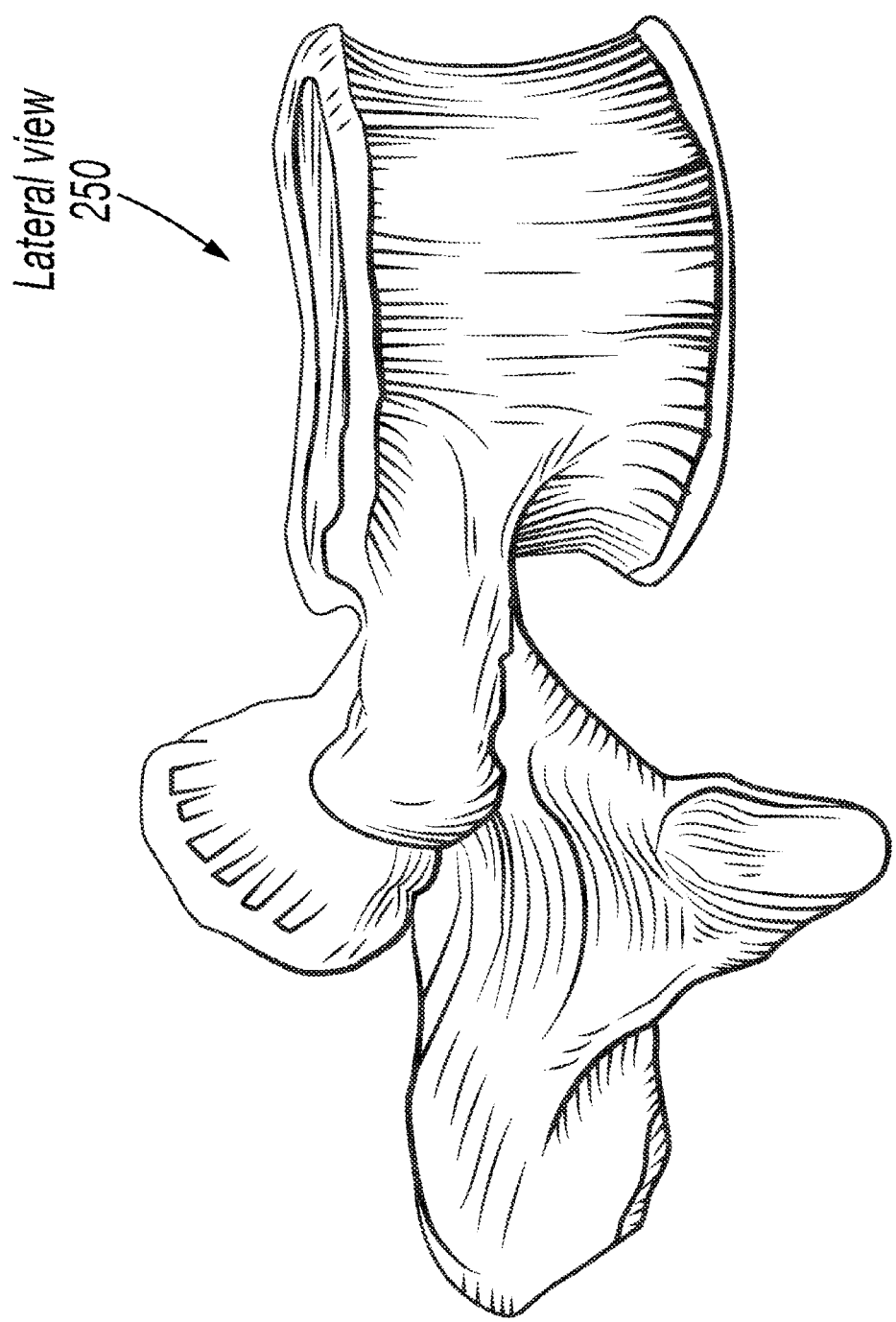
FIG. 2B illustrates an example lateral view of a vertebra for installing pedicle screws.
Figure 2C:
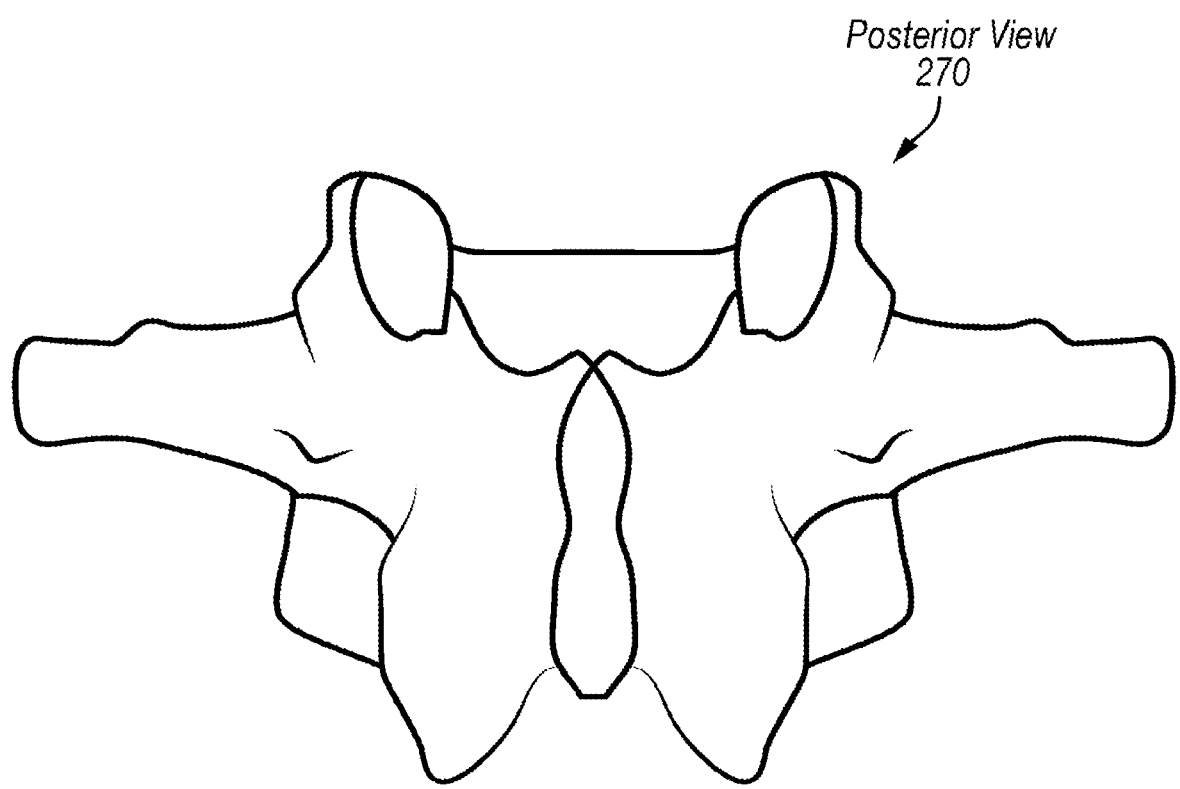
FIG. 2C illustrates an example posterior view of a vertebra for installing pedicle screws.

FIG. 2A illustrates a cross-sectional, axial view (may be referred to as a superior view) 200 of a vertebra 205 having pedicle screws 210 installed in respective pilot holes 220. A driver 230 may be used to screw the pedicle screws 210 positioned in pilot holes 220. Various shapes and types of pedicle screws 210 and driver 230 may be used. The pedicle screws 210 and driver 230 shown in FIG. 2A are for illustrative purpose only. A mating portion of the driver 230, which may be referred to as a tool or a medical tool, may be provided to allow a medical alignment device in an attachment apparatus to "mate" or position adjacent such mating portion to ensure that the driver 230 is installing the pedicle screw at a desired alignment angle, such as a three-dimensional alignment angle. FIG. 2B illustrates a lateral view (i.e., side view) 250 of a vertebra, which could be an orthogonal view of the vertebra 205 of FIG. 2A. FIG. 2C illustrates a posterior view 270 of a vertebra. The following discussion focuses on properly creating the pilot holes with a tool guided by the present disclosure.

Figure 3A:
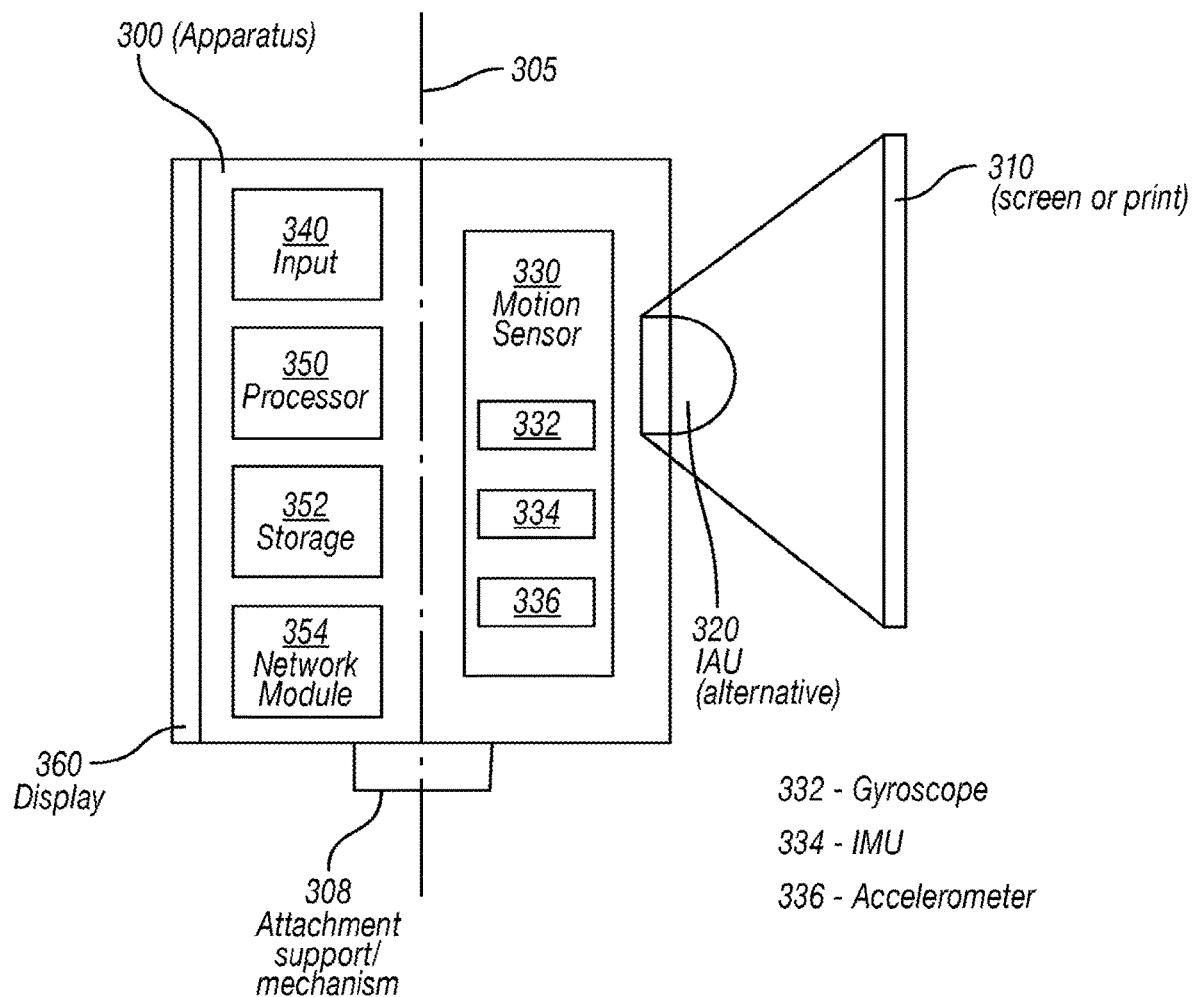
FIG. 3A presents a schematic diagram of an apparatus, which may be referred to as a medical alignment device, used in accordance with an embodiment to define and verify a three-dimensional alignment angle, which may also be referred to as an insertion angle, for use in installing devices, objects, hardware, and the like at a desired alignment angle.

FIG. 3A presents a schematic diagram of an apparatus 300, which may be referred to as a medical alignment device or alignment device, used in accordance with an embodiment to define and verify an angle, such as a three-dimensional alignment angle, for use in installing devices, objects, hardware, and the like, such as to align a pilot hole, or tract, such as the pilot hole 220 of FIG. 2. The apparatus 300 has an axis 305 (such as, for example, a longitudinal axis) that is used in some embodiments to align the apparatus 300 for image capture. The apparatus 300 includes an image acquisition unit 320 (or camera) for capturing an image 310 of the vertebra. In some embodiments, the image 310 may be obtained by positioning the apparatus 300 and/or image acquisition unit 320 in parallel with the transverse, sagittal, or coronal plane to obtain an image of the vertebra. These images may be diagnostic images such as, for example, CT scans, MIll scans, X-rays, and the like of items of interest, such as a vertebra. In some implementations, an attachment support and/or mechanism 308 is used to align and/or secure the apparatus 300 to a tool that creates a pilot hole for example.

In some embodiments, the image acquisition unit 320 can be a camera having sufficient field of view 360 to properly align the axis 305 of the apparatus 300 with a desired plane. In some embodiments, the axis 305 is representative of a vertical line centered laterally with respect to the image being captured. For example, if the desired image is intended to capture the vertebra from a cross sectional, axial view (e.g., see FIG. 2A), the axis 305 is aligned with the sagittal plane (i.e., the plane that is sagittal to the vertebra) and the image acquisition unit 320 is positioned parallel to the transverse plane to capture the top-down view of the vertebra shown in FIG. 2A. If the desired image is intended to capture the vertebra from a side view (e.g., a lateral image of the vertebra, see FIG. 2B), the axis 305 is aligned with the transverse plane (i.e., the plane that is transverse to the vertebra) and the image acquisition unit 320 is positioned parallel to the sagittal plane. If the desired image is intended to capture the vertebra from a posterior or anterior view (see, for example, FIG. 2C), the axis 305 is aligned with the sagittal plane and the image acquisition unit 320 is positioned parallel to the coronal plane.

In some embodiments, the image 310 may be a processed diagnostic image, e.g., an image displayed on a screen, a film, or a printed photograph. In other embodiments, the image acquisition unit 320 can directly use an image taken from an external machine (not illustrated), such as a radiograph, computed tomography (CT) scanner, or a magnetic resonance imaging (MM) machine.

The orientation apparatus 330 is operable to detect changes in movement, orientation, and position. In some embodiments, the orientation apparatus 330 includes at least one of a gyroscope 332, an inertial measurement unit 334, and an accelerometer 336, in other embodiments it may only include the gyroscope 332 with three axes of rotation to be able to determine a three-dimensional orientation of the apparatus 300. The gyroscope 332 is operable to measure at least one axis of rotation, for example, the axis parallel to the intersection of the sagittal plane and the coronal plane. In other embodiments, the gyroscope 332 includes more than one sensing axes of rotation, such as three axes of rotation, for detecting orientation and changes in orientation. The inertial measurement unit 334 can detect changes of position in one or more directions in, for example, a cardinal coordinate system. The accelerometer 336 can detect changes of speeds in one or more directions in, for example, a cardinal coordinate system. In some embodiments, data from all components of the orientation apparatus 330 are used to calculate the continuous, dynamic changes in orientation and position.

The apparatus 300 further includes, in some embodiments, an input component 340 that is operable to receive user input, such as through a keypad or touchscreen, to receive a device, such as a pedicle screw to be installed in a vertebra, insertion location and the desired angle representing an insertion direction of the pedicle screw. An example illustration of the user input component 340 is presented in accordance with FIGS. 6A-6D, as well as FIGS. 12, 13A, 13B, and 18. In some embodiments, the input component 340 can include a multi-touch screen, a computer mouse, a keyboard, a touch sensitive pad, or any other input device.

In some embodiments, the apparatus 300 further includes a processor 350. The processor 350 can be any processing unit capable of basic computation and capable of executing a program, software, firmware, or any application commonly known in the art of computer science. As to be explained, the processor 350 is operable to generate a three-dimensional alignment angle based on alignment inputs from to views orthogonal to one another, and to output an angle-indicative line representing the orientation of a device, such as a pedicle screw, pilot hole, etc. on the display showing a diagnostic image where the device, such as a pedicle screw, is to be installed. In some embodiments, the angle-indicative line provides a notation that the orientation of the apparatus 300 approximately forms the desired angle. The angle-indicative line is not limited to showing sagittal angles, but also angles in different planes, such as, for example, the coronal plane or the transverse plane.

The apparatus 300 may, in some embodiments, further include a memory storage unit 352 and network module 354. The memory storage unit 352 can be a hard drive, random access memory, solid-state memory, flash memory, or any other storage device. Memory storage unit 352 saves data related to at least an operating system, application, and patient profiles. The network module 354 allows the apparatus 300 to communicate with external equipment as well as communication networks.

In some embodiments, the apparatus 300 further includes a display 360. In some embodiments, the display 360 is a liquid crystal display that also serves as an input using a multi-touch screen. In some embodiments, the display 360 shows the angle-indicative line to a user and provides a notification when the apparatus is approximately aligned with the predefined desired angle, as determined by the gyroscope 332 or the orientation apparatus 330. For example, the notification can include a highlighted line that notifies the user the axis 305 has reached the desired angle, or is within an acceptable range of the desired angle. The apparatus 300 may provide any number of notifications to a user, including visual, auditory, and tactile, such as, for example, vibrations. The apparatus 300 will include a speaker as well as a device to impart vibrations to a user to alert or notify a user.

Figure 7:
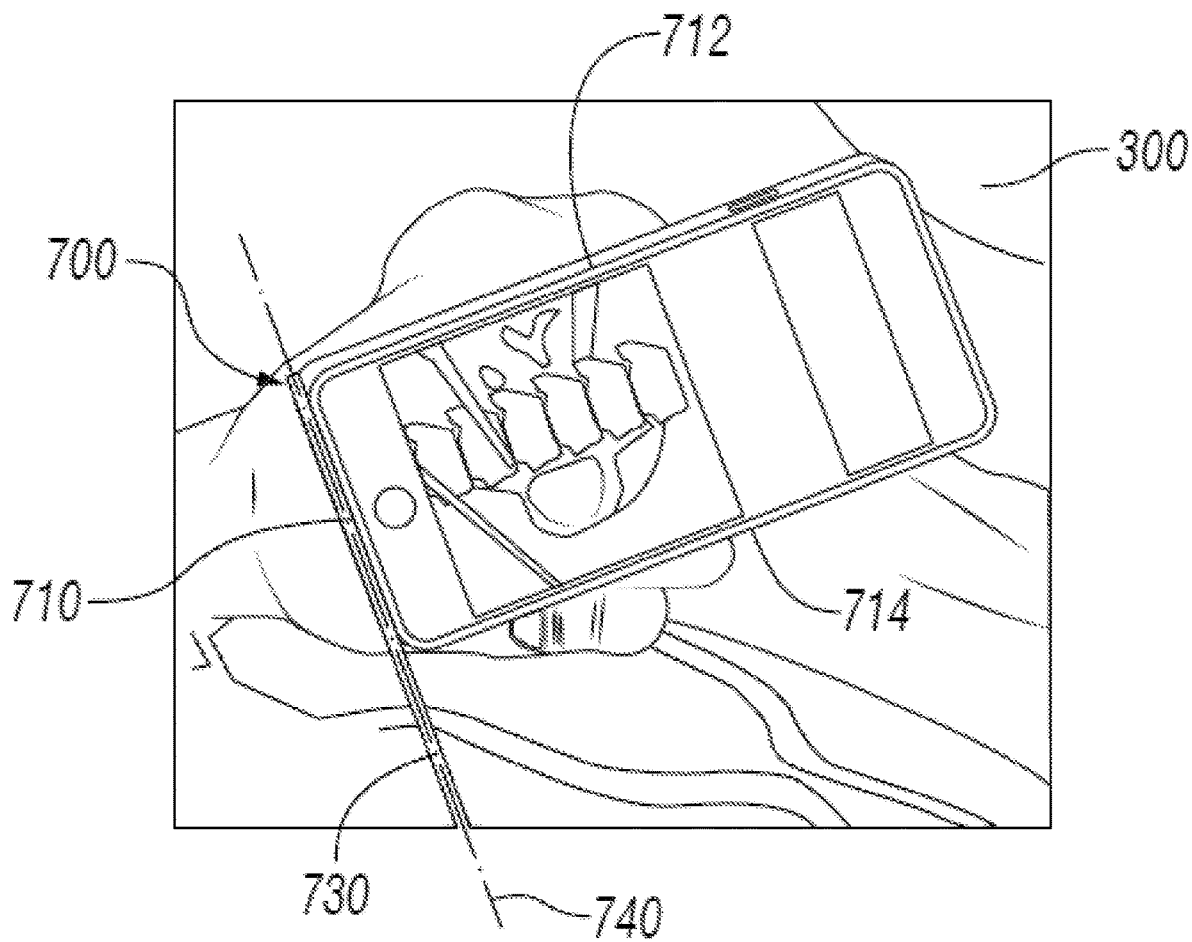
FIG. 7 illustrates an example of aligning the apparatus or medical alignment device.

Referring briefly to FIG. 7, in some implementations, the apparatus 300 (i.e., the medical alignment device) further includes an attachment support or mechanism 700 (also 308 of FIG. 3A) that allows the medical alignment device or apparatus 300 to be attached or provided adjacent to a tool, medical hardware, or equipment (i.e. a medical tool 730). The attachment apparatus 700 may be made of plastic, stainless steel, titanium, or any other material. The attachment apparatus 700 couples to the medical alignment device or apparatus 300 to the tool 730 by, for example, providing a casing that is attached to the medical alignment device 300 and is configured to connect to or abut the medical tool 730, for example, by aligning a first surface 710 of the medical alignment device 300 to the attachment apparatus 700 and thus to the medical tool 730. For example, the attachment apparatus 700 may be aligned to a longitudinal axis 740 of the medical tool 730. As such, orientation sensors in the medical alignment device 300 are properly aligned with the longitudinal axis 740.

In other implementations, a second surface 712 and a third surface 714 of the medical alignment device 300 may be used to secure and/or align the medical alignment device 300 to the attachment apparatus 700. In some embodiments, the attachment apparatus 700 may include a magnetic attachment apparatus for coupling the medical alignment device 300 to the tool 730 or to the attachment apparatus 700. The attachment apparatus 700 allows the medical alignment device 300 to provide real-time measurement and display of the orientation of the attached or aligned medical tool 730.

Returning to FIG. 3B, a schematic diagram of an axial view of a vertebra defining an alignment or insertion angle for a pilot hole in the vertebra in this plane for insertion or installation of a pedicle screw is provided. This view or diagnostic image of the vertebra may be electronically transmitted to the medical alignment device 300, or the view or image may be captured from a monitor or display of a diagnostic image using the image acquisition unit 320 of the medical alignment device 300 (sometimes referred to as apparatus 300). A sagittal angle 370 may be defined for the pilot hole 220 in the vertebra 205 that starts at the initial position 375, which may be referred to as the insertion location. The display 360 shows the field of view of the view captured by the image acquisition unit 320, assuming that was how the image was acquired, and allows a user to align the axis 305 of the apparatus 300 with the desired plane (e.g., the sagittal plane). In the embodiment shown in FIG. 3B, the sagittal angle 370 is the angle between the central axis 365 of the pilot hole 220 and the sagittal plane.

Figure 3B:
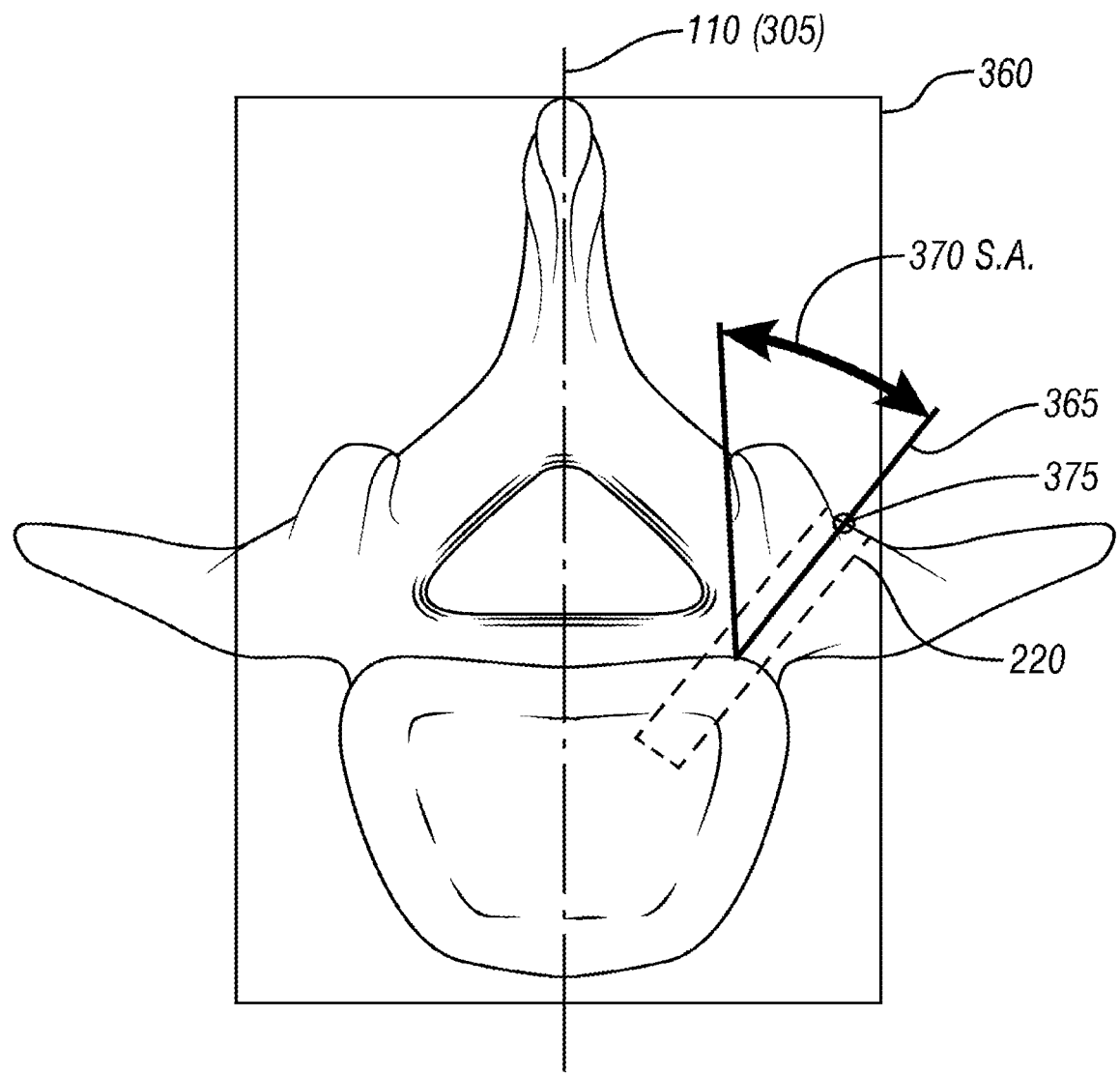
FIG. 3B illustrates a schematic diagram of an axial view of a vertebra for defining an alignment or insertion angle for a pilot hole in the vertebra in this plane.
Figures 4A, 4B:
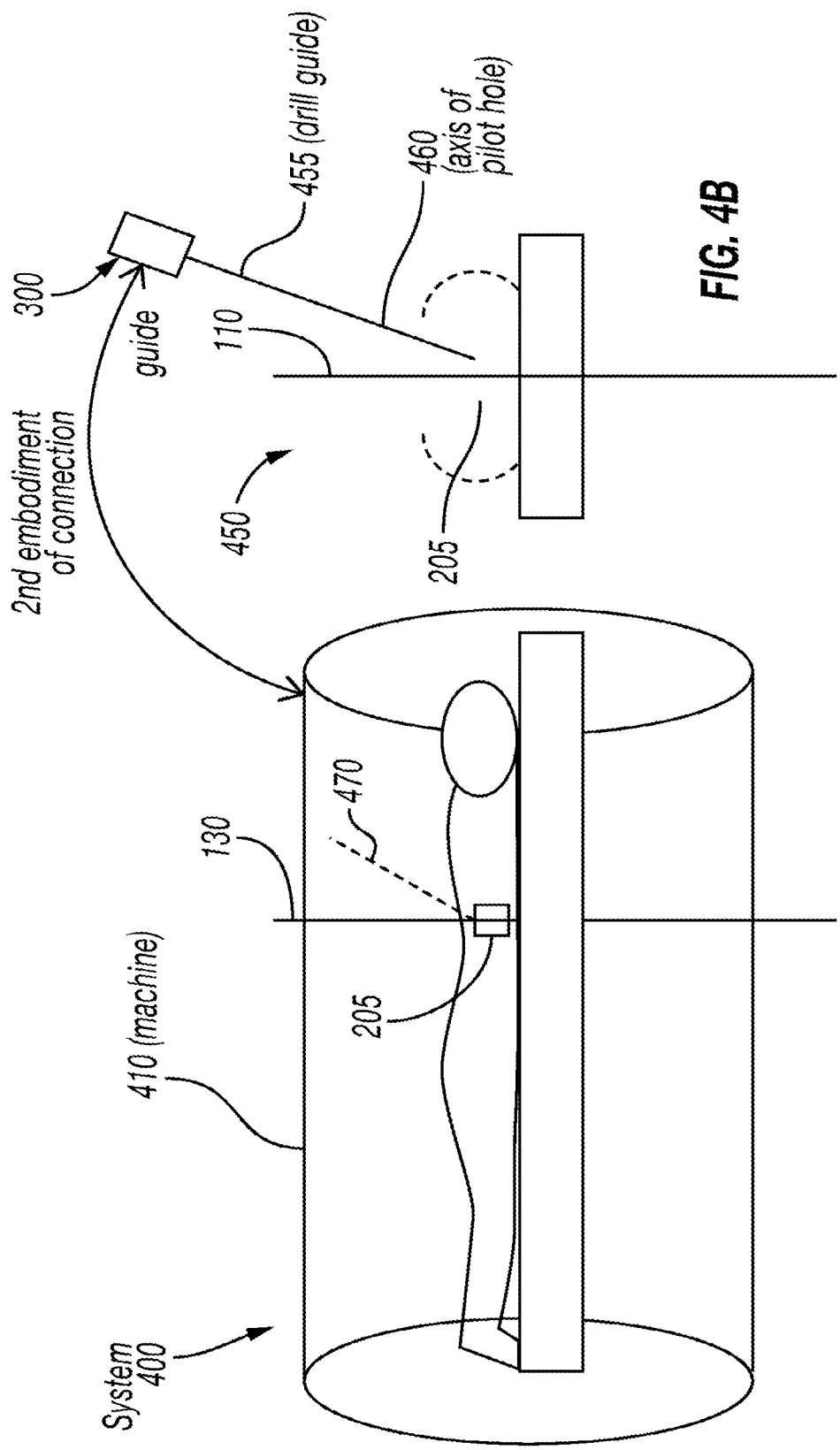
FIG. 4A illustrates a schematic side view of a medical operation system used in some embodiments for defining the sagittal angle of a pilot hole to be made in a vertebra.
FIG. 4B illustrates a schematic front view of a medical operation system used in some embodiments for defining the sagittal angle of a vertebra.

FIG. 4A illustrates a schematic side view of a medical operation system 400 used in some embodiments for defining the sagittal angle 370 of a pilot hole to be made in a vertebra which may be used in some embodiments for defining the sagittal angle 370 of the vertebra shown in FIGS. 3A and 3B. The medical operation system 400 includes a machine 410 for capturing a cross-sectional view of the vertebra 205. The machine 410 may be, for example, a CT scanner or Mill machine. The patient exits the machine 410 after the image is taken, as shown in FIG. 4B.

FIG. 4B illustrates a schematic front view 450 of the medical operation system 400 taken in the transverse plane for defining the sagittal angle 370 of the vertebra 205. The front view axis 460 (and correspondingly, the side view axis 470) of the pilot hole should to be precisely defined for the drilling guide 455. In some embodiments, the apparatus 300 may be attached to the drilling guide 455 with the attachment support/mechanism 308. Defining and verifying the sagittal angle 370 may be performed at the apparatus 300, as explained in connection with the method illustrated in FIG. 5B.

Figure 5A:
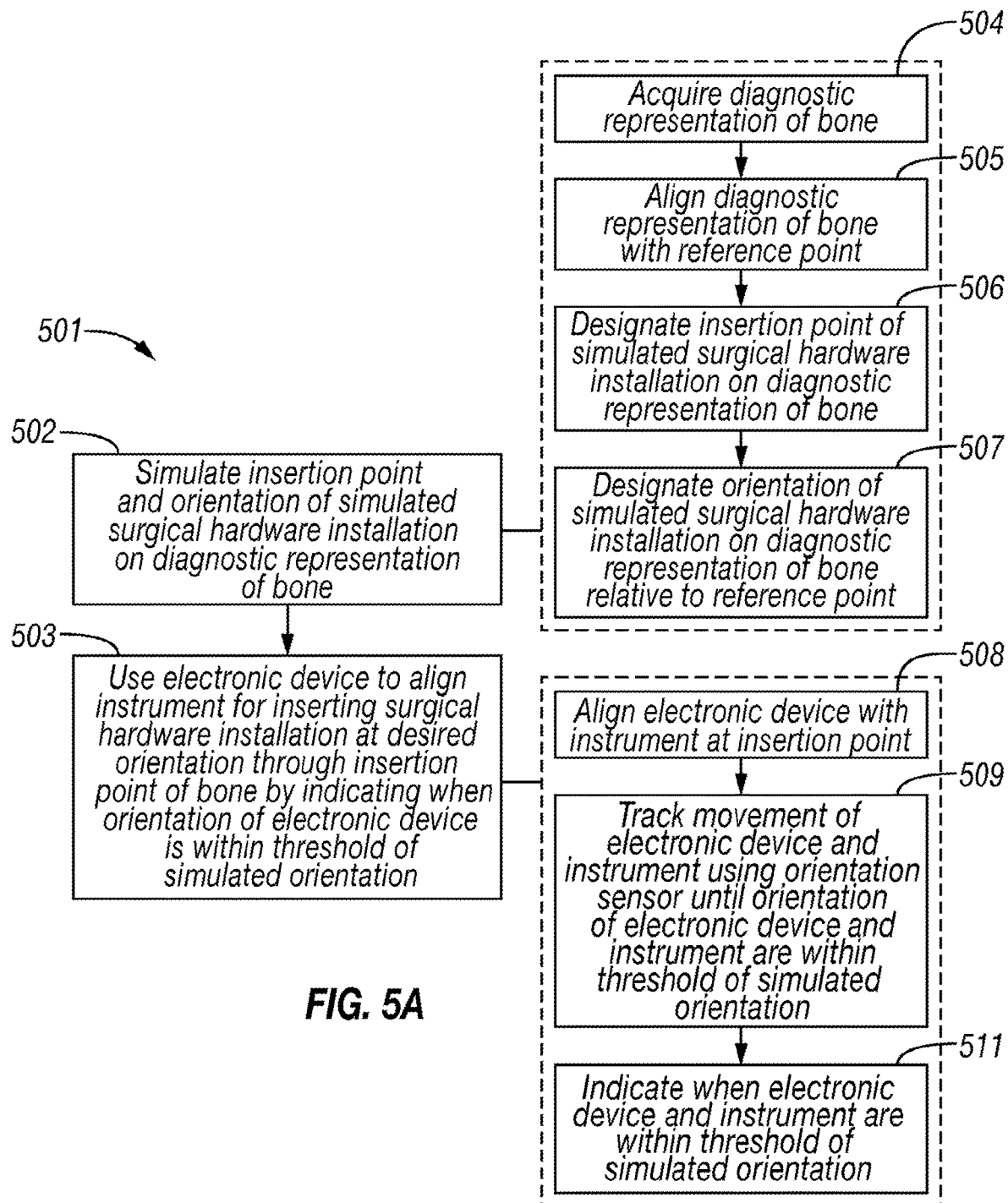
FIG. 5A illustrates an example flowchart for a method of determining an orientation of an instrument for inserting a medical device in a bone, in accordance with one or more embodiments of the present disclosure.

First, however, an example method of determining an orientation of an instrument for inserting a medical device in a bone is now described with reference to the flowchart 501 of FIG. 5A. A diagnostic image is obtained at the apparatus 300 and displayed. An insertion point and a desired orientation of a simulated surgical hardware installation are simulated and displayed on a diagnostic representation of a bone at block 502 and the desired alignment orientation is stored. Proceeding to block 503, the apparatus or medical alignment device 300 with orientation sensor, such as gyroscope 332, is used to align a tool, such as a medical tool, drill or the like for inserting or installing the surgical hardware at the desired alignment orientation from block 502 and through the insertion point of the bone by indicating when an orientation of the medical alignment device 300 is within a threshold of the simulated orientation with the desired alignment angle.

Simulating the insertion point and the orientation of the simulated surgical hardware installation on the diagnostic representation of the bone includes acquiring the diagnostic representation of the bone at block 504, aligning the diagnostic representation of the bone with a reference point at block 505, designating the insertion point of the simulated surgical hardware installation on the diagnostic representation of the bone at block 506, and designating the orientation of the simulated surgical hardware installation on the diagnostic representation of the bone relative to the reference point at block 507.

If block 502 is repeated using a second diagnostic representation of the bone that is orthogonal to the first diagnostic representation, the same steps 504 through 507 may be repeated on the second diagnostic representation with the location of the simulated surgical hardware constrained to the selections or settings made when the insertion point and orientation were selected in the first diagnostic representation. Once this is done, a three-dimensional alignment angle may be calculated or determined. This may be done by the apparatus or medical alignment device 300.

Using the electronic device, which may be the apparatus or medical alignment device 300, to align the instrument or tool for inserting the surgical hardware installation at the desired orientation through the insertion point includes aligning the electronic device with the instrument or tool at the insertion point in block 508, tracking movement or orientation of the electronic device and the instrument or tool using an orientation sensor, such as gyroscope 332, of the electronic device until the orientation of the electronic device and the instrument are within the threshold of the simulated orientation at block 509, and indicating when the electronic device and the instrument are within the threshold of the simulated orientation at block 511. The indication may be visual, auditory, or tactile. The orientation of the electronic device, and hence the alignment of the instrument or tool, may be a two-dimensional alignment angle, in certain implementations, or a three-dimensional alignment angle. FIG. 7 illustrates an example application of the alignment of block 508.

Figure 5B:
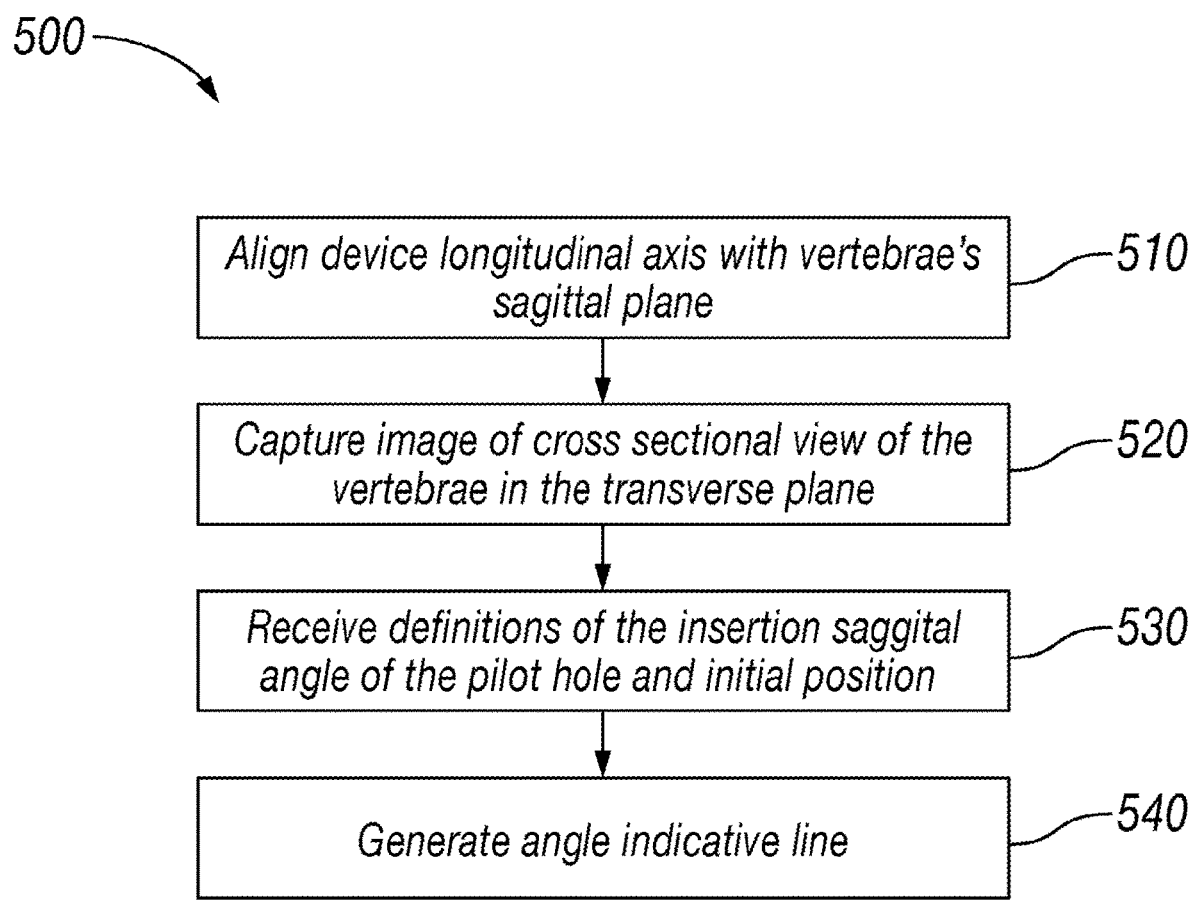
FIGS. 5B, 5C, and 5D illustrate example flowcharts for methods for indicating the sagittal angle, transverse angle, and coronal angle, respectively, in accordance with one or more embodiments of the present disclosure.
Figure 5C:
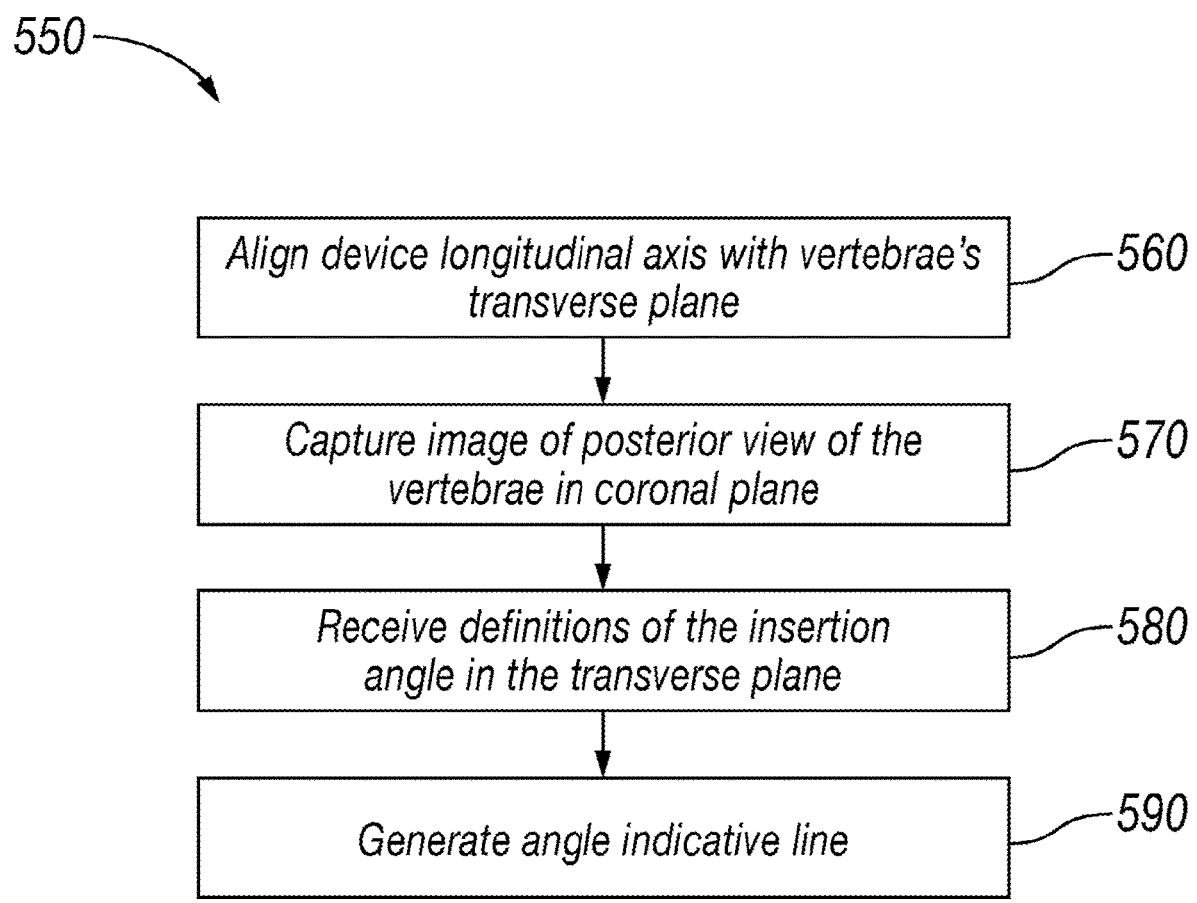
Figure 5D:
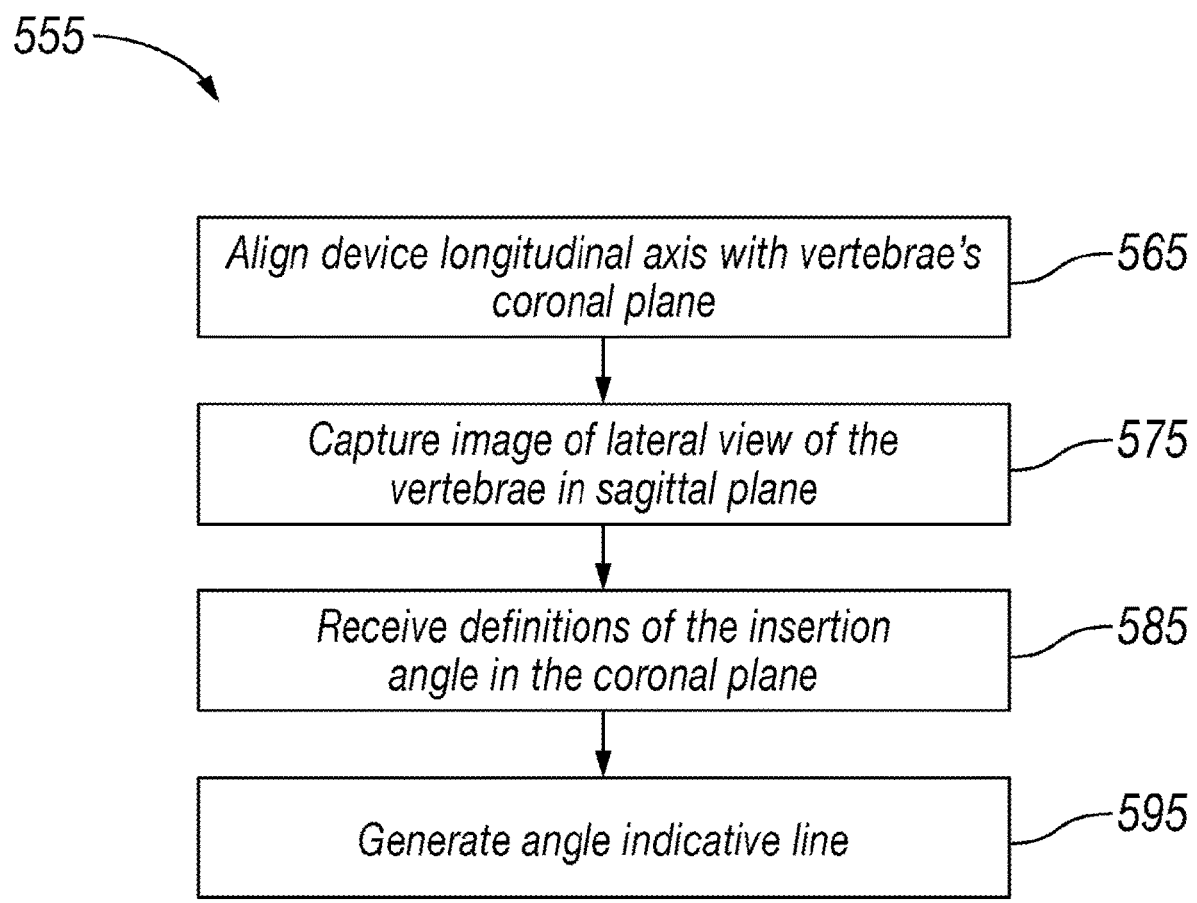

FIGS. 5B, 5C, and 5D illustrate example flowcharts for methods for indicating or determining a desired alignment angle, which also may be referred to as an insertion angle, in the: (i) sagittal plane, which may be referred to as the sagittal angle, (ii) the transverse plane, which may be referred to as the transverse angle, and (iii) the coronal plane, which may be referred to as the coronal angle, respectively, in accordance with one or more embodiments of the present disclosure. Each of these methods may be thought of as generating or determining a two-dimensional alignment angle in their respective plane.

FIG. 5B illustrates an example flowchart 500 of a method for indicating the sagittal angle 370. The method of the flowchart 500 is for verifying any insertion angle 370 of the pilot hole 220 in the sagittal plane 110 for receiving a pedicle screw 210 in the vertebra 205. At 510, the axis 305 of the apparatus 300 is aligned or is oriented with the sagittal plane of an image of the vertebra, in this embodiment. In some embodiments, a user may hold the apparatus 300 and rotate the apparatus 300 to match a marking indicating the axis 305 with features of the vertebra 205 that indicate the sagittal plane. In some embodiments, the marking may be displayed on the screen as the user aligns the device. In other embodiments, the image of the vertebra (or other desired object or bone) is a diagnostic image that is displayed on the apparatus 300, which may be a medical alignment device 300, and is already oriented in some manner to the sagittal plane.

At 520, the image of the cross-sectional view is captured in the transverse plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent or transmitted to the apparatus 300 via a wired or wireless connection to be displayed on the apparatus 300 such that no physical representation (e.g., films, photos, monitors) may be needed for this step.

At 530, definitions of the insertion sagittal angle 370 of the pilot hole 220 and the initial position 375, also referred to as the insertion location, of the pilot hole 220 are provided or specified by a user. This input operation may be performed using various input devices of the apparatus 300, including a computer mouse, a keyboard, a touchscreen, or the like. In one embodiment, a multi-touch screen (e.g., the display 360) is used for both displaying the image and receiving the definition input from a user. Example illustrations of this input are provided in FIGS. 6A-6D, where the insertion location or initial position 375 of the pilot hole 220 for the installation of a pedicle screw are established by locating (or simulating) graphically the insertion location on the displayed diagnostic image, and the applicable alignment angle for the displayed plane may defined by moving or locating (or simulating) the desired position of the alignment angle of the pilot hole/pedicle screw.

At 540, an angle-indicative line is generated by a processor and displayed on the display 360 along with the diagnostic image. The angle-indicative line can rotate in response to the apparatus 300 rotation and provides a notification when the orientation or position of the apparatus 300 approximately forms the insertion sagittal angle 370 between the apparatus 300 longitudinal axis 305 and the sagittal plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of apparatus 300 to generate the current orientation of the apparatus 300. This current orientation may be compared to the desired insertion angle (or alignment angle) discussed above in connection with 530 to determine whether or not alignment exists or the extent of alignment, and this may be compared or shown graphically.

The indicative line may generate notations in various forms, including a visual alert such as highlighting the angle-indicative line, an audio alert such as providing a continuous sound with variable frequency indicative of the proximity between the current angle and the desired angle, and a small vibration that allows the user to notice the angular change. It should be appreciated that any audio alert may be used, such as a single sound or series of sounds when the desired angle is reached. Likewise, a single vibration or a series of vibrations may be emitted when the desired angle is reached. In some implementations, the flowchart 500 illustrated in FIG. 5B may be applicable for generating indication angles in the transverse plane or the coronal plane for indicating a respective transverse angle or a coronal angle.

FIG. 5C illustrates a flowchart 550 of an implementation for indicating a transverse angle, which is an angle with respect to the transverse plane of the vertebra. The method of the flowchart 550 is for verifying any pedicle screw insertion angle in the transverse plane of the vertebra 205. At 560, the axis 305 of the apparatus 300 is aligned with the transverse plane. In some embodiments, a user may hold the apparatus 300 and rotate the apparatus 300 to match a marking indicating the axis 305 with features of the vertebra 205 that indicate the transverse plane. In some embodiments, the marking may be displayed on the screen as the user aligns the device.

At 570, an image of the posterior view is captured or provided in the coronal plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 580, definitions of the insertion angle in the transverse plane 130, and the initial position 375 of the pilot hole are provided by a user, as similar to the sagittal angle defined at 530.

At 590, an angle-indicative line for the corresponding transverse angle is generated by a processor and displayed on the display 360. The angle-indicative line can rotate in response to the apparatus 300 rotation and provides a notification when the apparatus 300 approximately forms the insertion transverse angle, as defined in step 580, between the apparatus 300 longitudinal axis 305 and the transverse plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of the apparatus.

FIG. 5D illustrates a flowchart 555 of another implementation for indicating a coronal angle. The method of the flowchart 555 is for verifying any insertion angle of a pedicle screw 210 in the vertebra 205 in the coronal plane 120. At 565, the axis 305 of the apparatus 300 is aligned with the coronal plane. In some embodiments, a user may hold the apparatus 300 and rotate the apparatus 300 to match a marking indicating the axis 305 with features of the vertebra 205 that indicate the coronal plane. In some embodiments, the marking may be displayed on the screen as the user aligns the device.

At 575, the image of the lateral view is captured in the sagittal plane. In one embodiment, the apparatus 300 includes a smart phone, a tablet computer, a laptop computer, or any portable computational device including those that include a camera for capturing a representation of the posterior view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 585, respective definitions of the insertion angle in the coronal plane 120, and the initial position 375 of the pilot hole are provided by a user, as similar to the sagittal angle defined at 530.

At 595, an angle-indicative line for one of the corresponding coronal angle is generated by a processor and displayed on the display 360. The angle-indicative line can rotate in response to the apparatus 300 orientation and provides a notification when the apparatus 300 approximately forms the insertion coronal angle between the apparatus 300 longitudinal axis 305 and the coronal plane. In some implementations, the angle-indicative line is a rotating line generated in the display 360 that allows a user to monitor the change of orientation of the apparatus 300. The orientation monitoring is performed with an orientation apparatus 330 of the apparatus 300. More specifically, in some embodiments, a gyroscope 332 that includes at least one axis of rotation may provide the function of monitoring the apparatus's orientation or position.

Figure 6A:
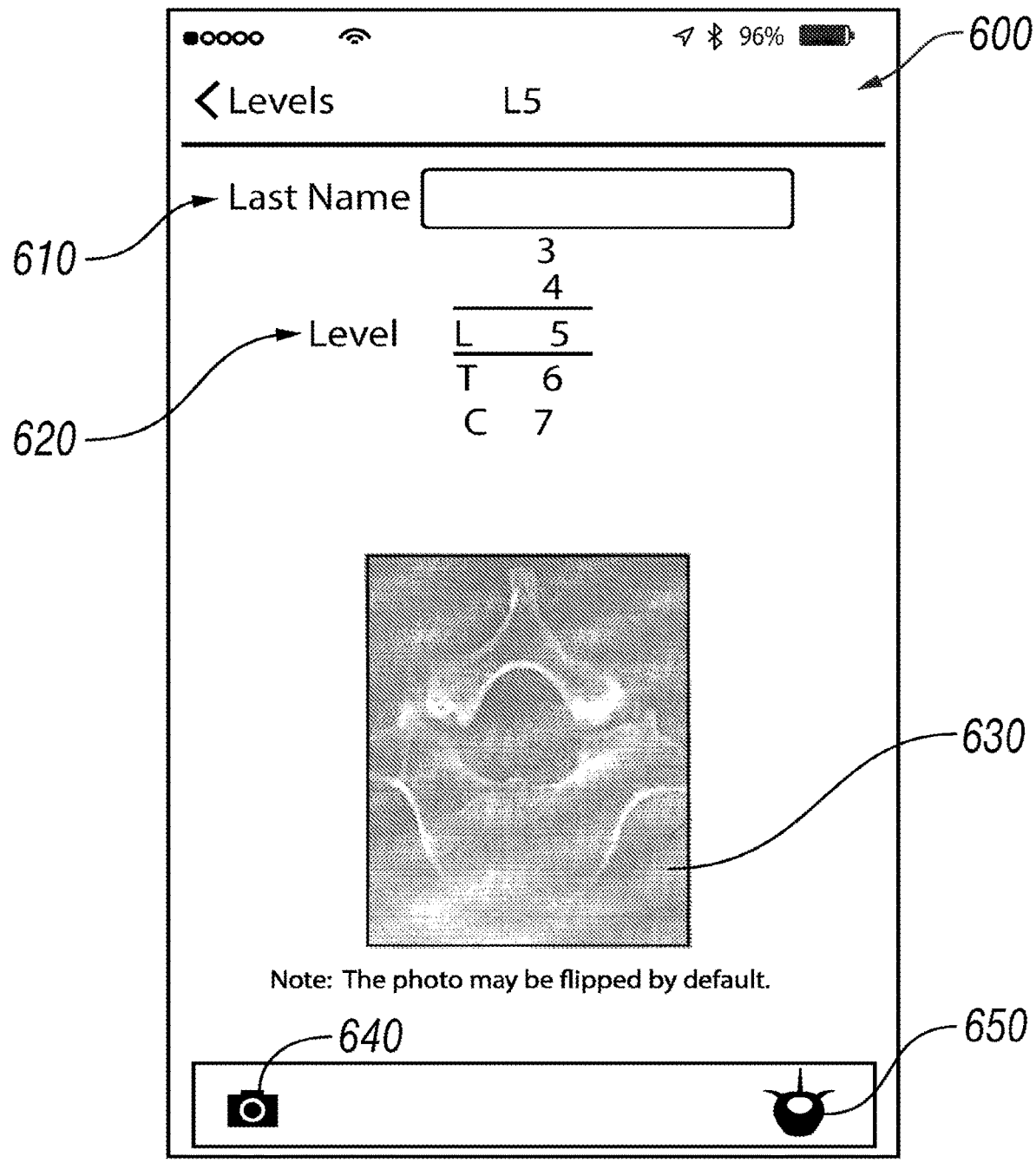
Figure 6B:
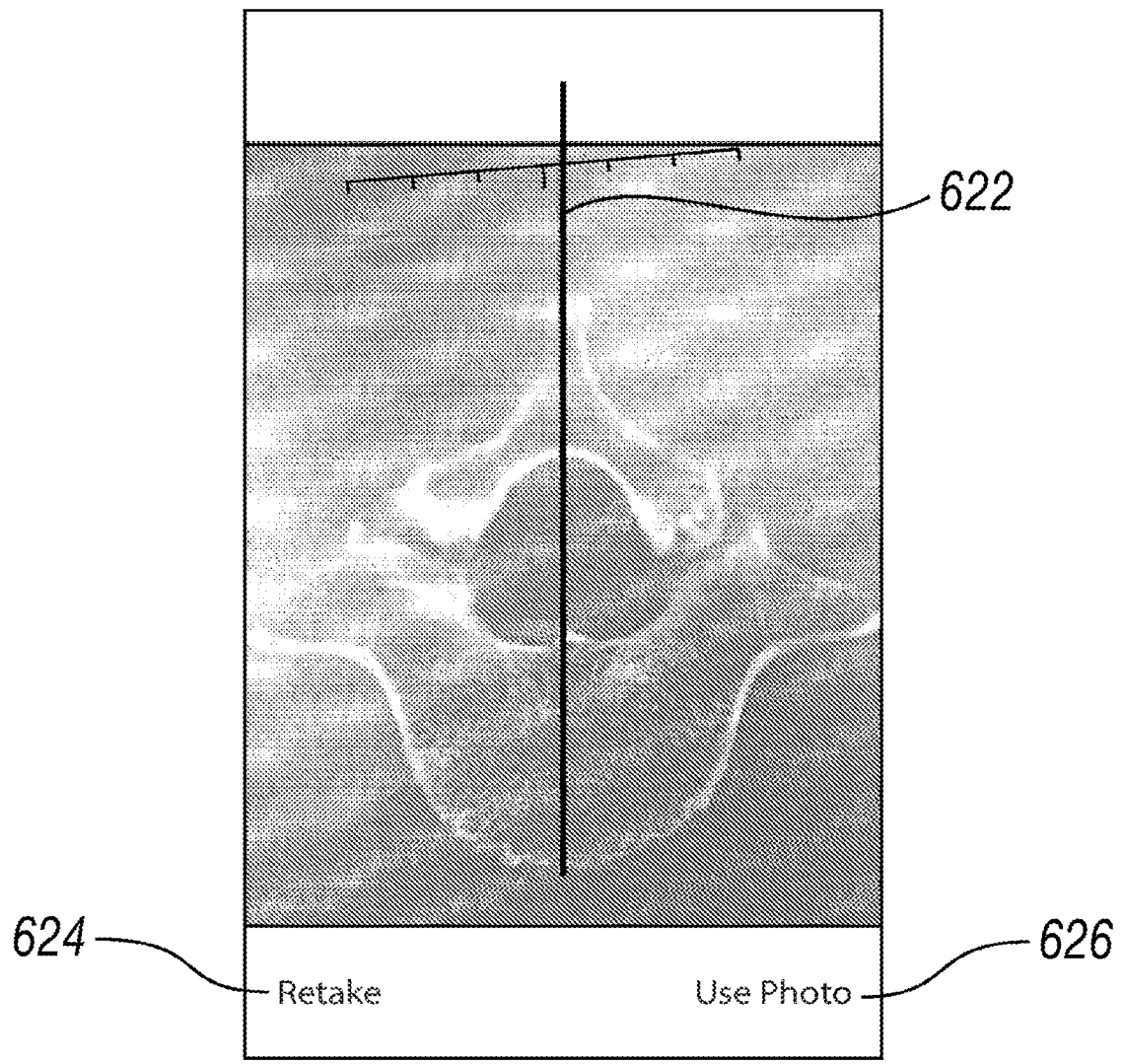
Figure 6C:
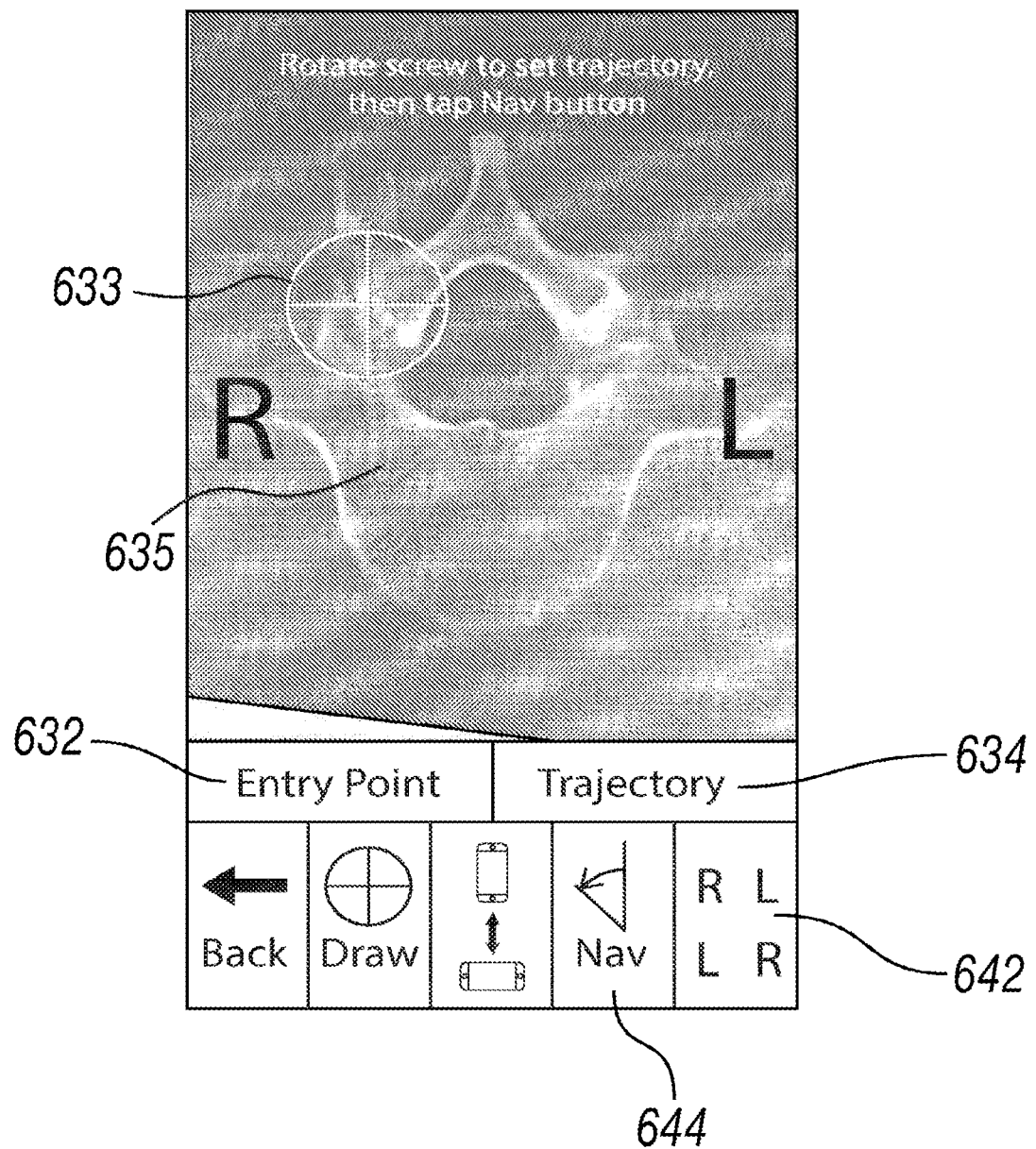
Figure 6D:
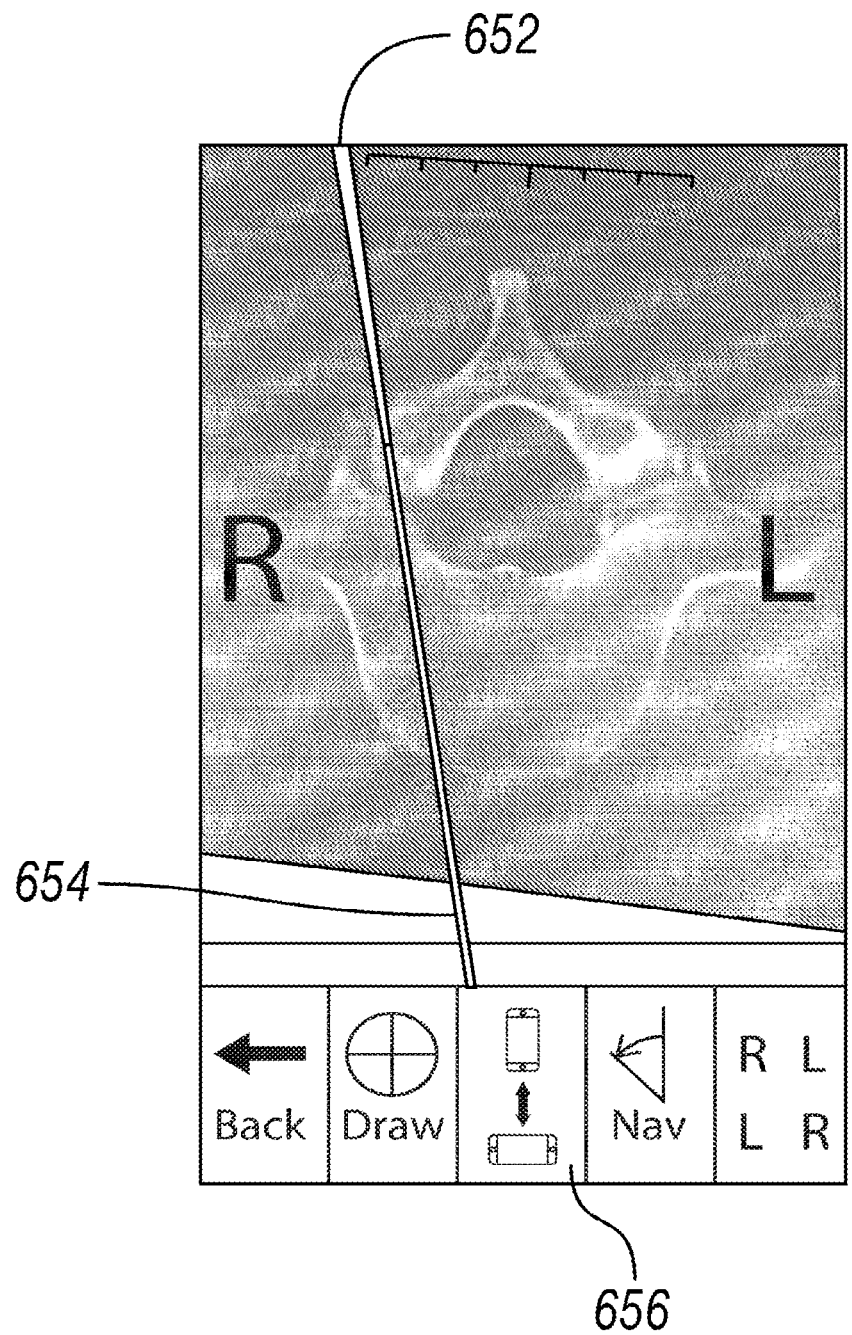

FIGS. 6A-6D illustrate examples of user interfaces for controlling a computer implemented program to perform the methods shown in FIG. 5A-5D. FIG. 6A illustrates an interface 600 for selecting vertebra of a patient, FIG. 6B illustrates displaying a diagnostic image and aligning (or confirming the alignment) the axis 305 of the apparatus 300 with the sagittal plane of the image, FIG. 6C illustrates defining a pedicle screw's position, including its insertion location or entry point at the cross hair, and its sagittal angle 370 on the diagnostic image, and FIG. 6D illustrates generating an angle-indicative line 652 for showing the angle between the longitudinal axis of the apparatus and the sagittal plane. In some embodiments, the angle-indicative line may represent a virtual gear shift pedicle probe, or other instrument for aligning a pedicle screw or pilot hole. When the virtual gear shift or angle is properly aligned, the virtual gear shift may change colors, or may change length or width. The angle-indicative line can rotate or reorient in response to the apparatus 300 rotation or reorientation, and provides a notification when the apparatus 300 approximately forms the desired alignment angle in this view between the apparatus 300 longitudinal axis 305 and the desired alignment angle.

In FIG. 6A, the patient's profile may be selected or added by typing the last name of the patient in the window 610. The corresponding vertebra for the desired angle is selected in the window 620. The camera button 640 allows a user to take a picture of a diagnostic image of the actual vertebra or to receive such a diagnostic image. The diagnostic image or picture is shown in the window 630. The button 650 allows the user to move onto the next step. As previously discussed, the picture at the vertebra may be provided without use of the camera or camera button 640.

For example, by using a camera of a mobile device, a user can take a picture of an axial view (either CT or MRI) in the transverse plane 130, of the desired vertebral body 205. Use the line 622 to line up the vertebral body so that it is proximately vertical for aligning with the sagittal plane (or other desired plane), as shown in FIG. 6B. A retake button 624 allows the user to go back to the previous steps to retake the image to ensure the alignment is proper. The button 626 allows the user to select the current photo to be used in the following operations.

After selecting button 626, the user may be returned to the detail view as shown in FIG. 6C. The photo may, in some embodiments, be automatically flipped to approximate its position during surgery. Button 642 may be selected to flip the orientation of the photo. For example, the RL button 642 can be used to flip the picture (and pedicle screw) depending on whether the surgeon is placing the screw while looking towards the patient's head (e.g., in the longitudinal axis toward the cephalad direction) or towards their feet (e.g., in the longitudinal axis toward the caudal or caudad direction).

The user next selects the optimal or desired pedicle screw position by selecting the navigation button 644 to move the simulated pedicle screw to a desired location by moving the crosshairs 633 to the cortical entry point of the screw, for example, by tapping the entry point button 632 to confirm, and then tapping the trajectory button 634 and rotate the screw to its desired position 635. The crosshairs 633 specify the insertion location, such as the initial position 375 of FIG. 3B.

Tap the Nav button 644 and a virtual gear shift probe 652 (which may represent any tool or axis, such as a drill or pilot hole longitudinal axis) appears on the screen. The gear shift probe's orientation matches the orientation of the apparatus 300, which will include orientation circuitry, such as a gyroscope to determine the orientation of apparatus 300. In some embodiments, once the angle of the gear shift probe 652 is about 20 degrees within the selected trajectory, the gear shift probe 652 will turn yellow, at 5 degrees, it will turn green, and when the alignment is within 1 degree of the target angle, a green line 654 will extend outward and the pedicle screw will disappear to signify that the apparatus 300 is properly aligned.

In some embodiments, the device or apparatus 300 can be placed in a sterile bag and then be placed against the gear shift probe as it is being used to create the path for the pedicle screw. As provided herein, the apparatus 300 may be positioned in an attachment apparatus so that the apparatus 300 may be conveniently aligned or abutted with a tool, such as the gear shift probe, drill, and the like.

Some gear shift probes may be too short to allow the device (apparatus 300) to be placed against them lengthwise. If this is the case, tap the 90 degree button 656 and the screen will be rotated so the short edge of the device can be placed against the gear shift probe.

Other implementations of the disclosed system and method are possible. For example, the apparatus 300 may also use a second or more views to define various angles not limited within the sagittal plane. For example and in accordance with the foregoing disclosure, images of the vertebra may be captured from two orthogonal planes, such as through superior, lateral, posterior, anterior views, and various combinations thereof, to provide multiple reference points so that three-dimensional representations of the alignment angles can be presented.

In addition, different mobile computer devices may be used or modified into the apparatus 300 by equipping corresponding image acquisition units, input terminals, and motion or orientation sensing units. In some embodiments, the apparatus 300 includes a smart phone or another electronic device having a gyroscope. In addition, other motion or orientation sensors may be included such as the inertial measurement unit 334, and the accelerometers 336. The apparatus 300 may also be attached onto various medical devices or equipment for guiding insertion angles that require high precision and ease of use. The smartphone may be an iPhone for example. Also, in some application, the mobile computer device may be an iPod Touch, iPad, Android phone, Android tablet, Windows Phone, Windows tablet, or Blackberry phone. Also, in some applications, the mobile computer device may be an Apple TV in combination with an Apple TV remote, or a Nintendo Wii in combination with a Nintendo Wii remote. Indeed, the mobile computer device may be any combination of electronic devices where the orientation sensor (such as a gyroscope) is in one electronic device and the processor is in another electronic device.

In some embodiments, axis other than the device's longitudinal axis may be used. Axes can be defined by a portion of the device (e.g., an edge or surface of the device). More than one orientation apparatus 330 may be used at the same time, if desired. Surgical apparatus may include pedicle screws, gear shift probes, and other medical devices.

It should be appreciated that the various methods and techniques described above may be utilized with a virtual reality or augmented reality device, either on its own or in conjunction with another electronic device such as a smartphone or computer. The determination of the insertion point or pilot hole and the proper angle for the surgical tool used to attach or install the pedicle screw or other medical device may proceed in any of the fashions as described above, and then the virtual reality or augmented reality device may be used to display the proper insertion point or pilot hole and proper angle for the surgical tool to a physician.

In the case of a virtual reality device, the simulation of a tool or axis at a desired three-dimensional alignment angle or other alignment angle may be displayed to the surgeon or user in an immersive three-dimensional fashion so that the surgeon can view the bone or tools used in a procedure as it will appear during a surgery. In addition, the planning of the insertion point or pilot hole and the proper angle for the surgical tool may be conducted with the aid of the virtual reality device.

In the case of an augmented reality device, during the actual surgery, virtual visual indicia may be displayed superimposed over the real bone, illustrating to the physician precisely where to insert the surgical tool and at precisely which angle the surgical tool should be inserted and operated.

An augmented reality or virtual reality based system 700 for use in assisting of the determination of the proper insertion point and proper angle for a surgical tool to be used to install a pedicle screw is now described with reference to FIG. 8. The system 700 includes an electronic computing device 702, such as a smartphone, tablet, desktop based personal computer, or laptop based personal computer. A virtual reality based or augmented reality based device 704, such as a wearable headset, wearable goggles, three dimensional projector, or holoprojector, may be capable of wired or wireless communication with the electronic computing device 702.

Figure 9:
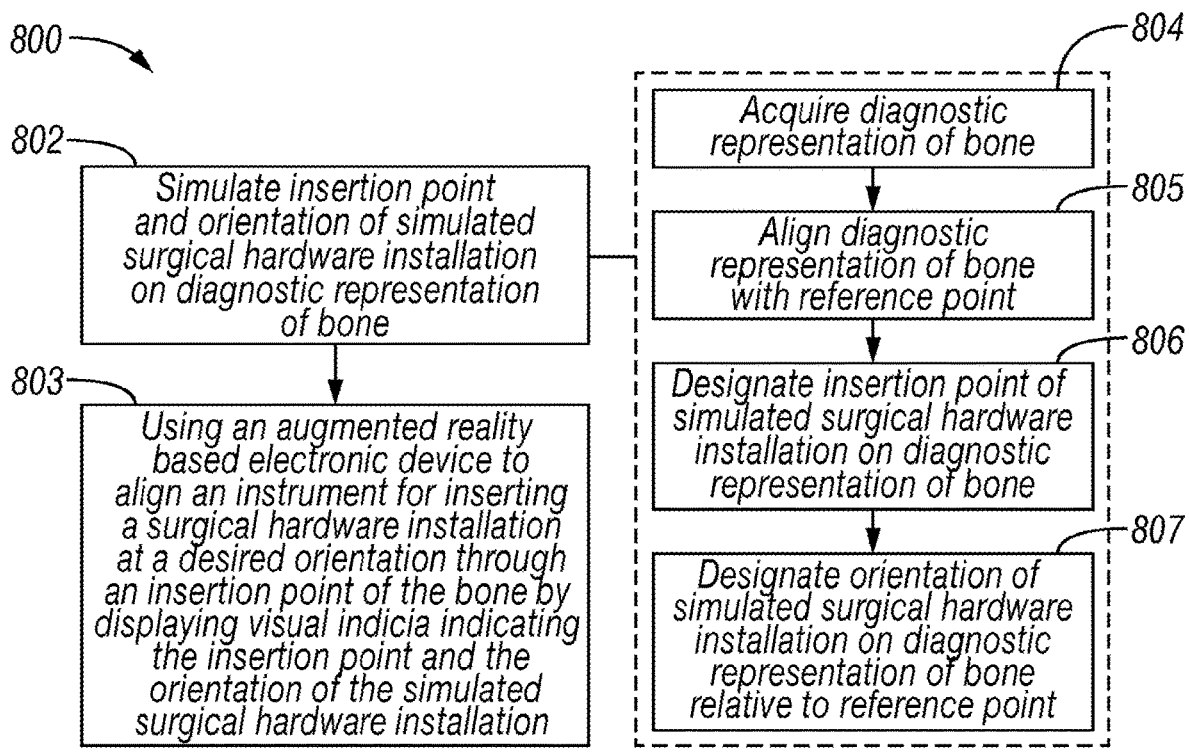
FIG. 9 illustrates an example flowchart for a method of determining and displaying an orientation of an instrument for inserting a medical device in a bone, using an augmented reality device, in accordance with one or more embodiments of the present disclosure.

Operation of the system 700 is now described with reference to the flowchart 800 shown in FIG. 9. Operation begins with the electronic computing device 702 simulating an insertion point and orientation of a surgical hardware installation on a diagnostic representation of the bone onto which it is to be installed (Block 802). This operation can proceed in any of the ways described above, although it should be understood that the virtual reality based or augmented reality based device 704 may be used as a display during this process. It should further be appreciated that the virtual reality or augmented reality based device 704 may have a camera associated therewith used to image the real world and provide it to the user when operating in an augmented reality mode (Block 803).

One way to proceed with this simulation begins with acquiring a diagnostic representation of the bone (Block 804). This may be performed using an image capturing device associated with the electronic computing device 702, such as a two dimensional or three dimensional camera, or this may be performed using a standalone image capturing device and then receiving the image data from that device at the electronic computing device 702. Still further, this may be performed using a medical imaging device, such as a CT scan or MM scan, and then receiving that image data at the electronic computing device 702, which may serve as apparatus 300.

Thereafter, the diagnostic representation of the bone is aligned with a suitable reference point (Block 805). Then, an insertion point of for a simulated surgical hardware installation is designated on the diagnostic representation of bone (Block 806). Next, an orientation of the simulated surgical hardware installation on the diagnostic representation of bone relative to reference point is determined (Block 807). This orientation is determined in three dimensions, and can be referenced to suitable planes of the body as defined by typical medical terminology and known to those of skill in the art.

Figure 10:
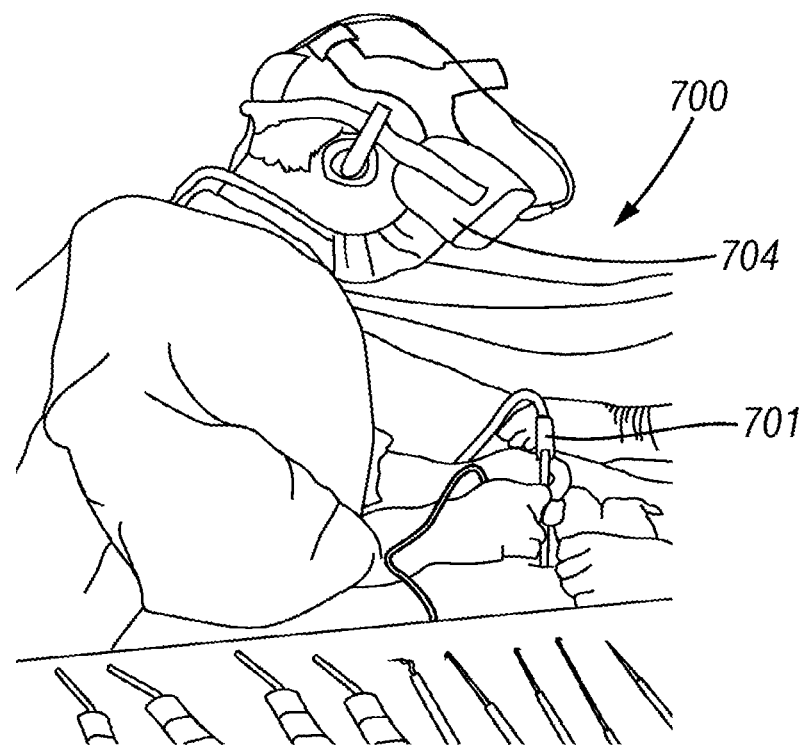
FIG. 10 illustrates the system of FIG. 8 in use to assist with inserting a medical device in a bone.
Figure 11:
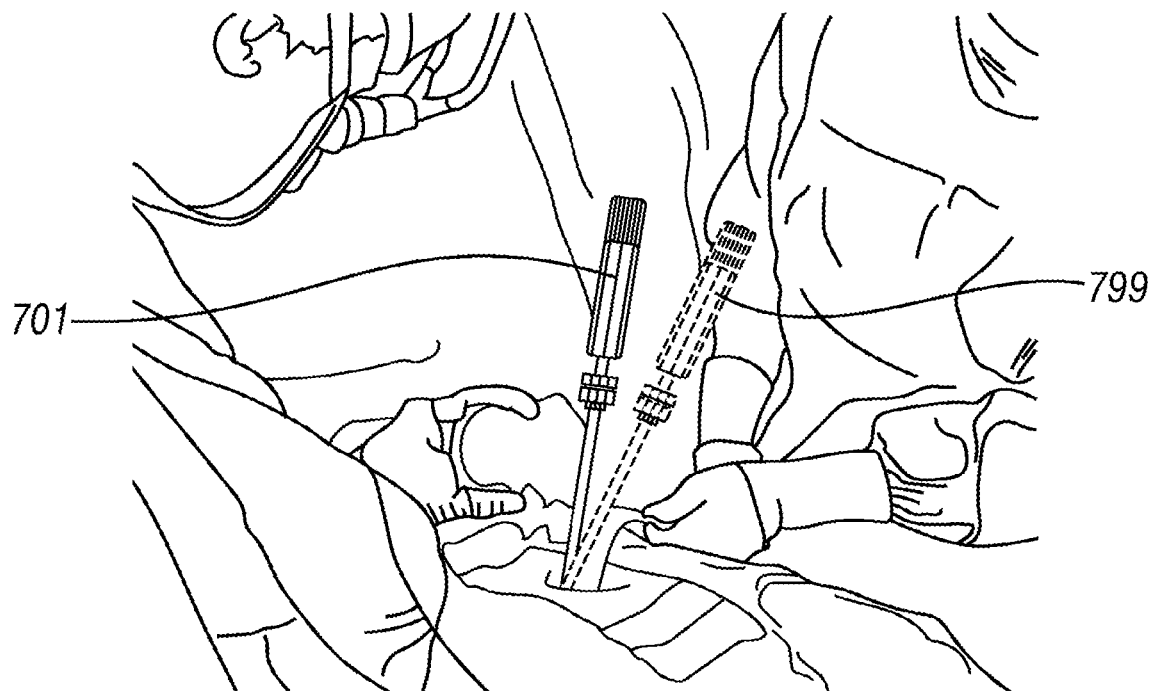
FIG. 11 illustrates an augmented reality display presented by the system of FIG. 8 showing an orientation angle for an instrument for inserting a medical device in a bone.

Then, the surgery itself may be performed. During surgery, virtual reality based or augmented reality based device 704 is worn by the operating physician or surgeon, as shown in FIG. 10. Here, the virtual reality or augmented reality based electronic device 704 is used to align an instrument or tool 701 for inserting a surgical hardware installation at a desired orientation through an insertion point of the bone by displaying visual indicia indicating the insertion point and the orientation of the simulated surgical hardware installation (Block 803). This visual indicia can be shown superimposed over the bone itself, such as shown in FIG. 11 by the virtual representation of the tool 799. It should be appreciated that the visual indicia need not be a virtual representation of the tool 799 as shown, and may instead be an arrow, a line, or any other suitable visual representation.

In some instances, cameras, position detectors, or other devices situated about the surgery site may be used to gather real time information about the actual position of the tool 701, so that feedback may be presented to the surgeon. For example, the visual indicia may change when the tool 701 is properly aligned, or may inform the surgeon that the tool 701 is not properly aligned. Likewise, additional visual indicia may be displayed when the tool 701 is properly aligned, or when the tool 701 is not properly aligned. Similarly, an audible response may be played by the virtual reality based or augmented reality based device 704 either when the tool 701 is properly aligned, or when the tool 701 is not properly aligned, or to guide the surgeon in moving the tool 701 into the proper position. In some cases, a position detector may be associated with or collocated with the tool 701, and the position detector such as an accelerometer may be used in determining whether the tool 701 is properly aligned, or when the tool 701 is not properly aligned.

In some instances, based on the above feedback, if the patient moved or the bone is moved, the visual indicia 799 is moved along with the bone by the virtual reality based or augmented reality based device 704 so that proper alignment is maintained during the surgery.

Figure 8:
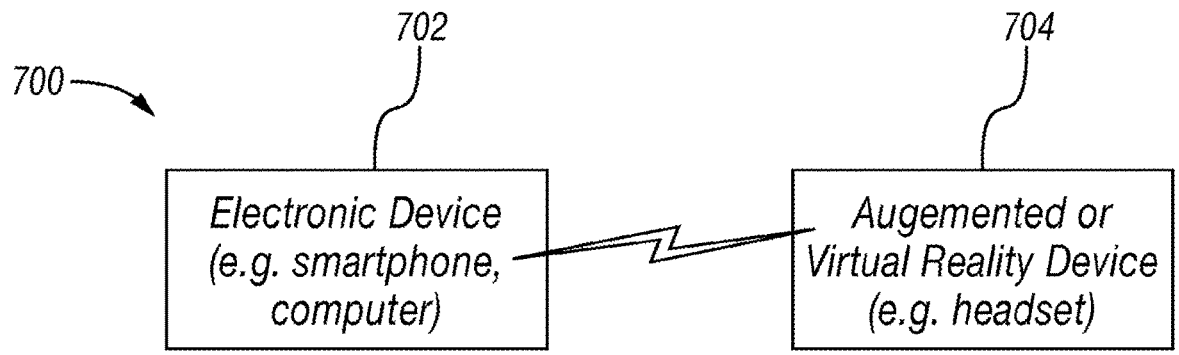
FIG. 8 presents a schematic diagram of a system used in accordance with an embodiment to define and verify an insertion angle for a pilot hole in a vertebra.
Figure 12:
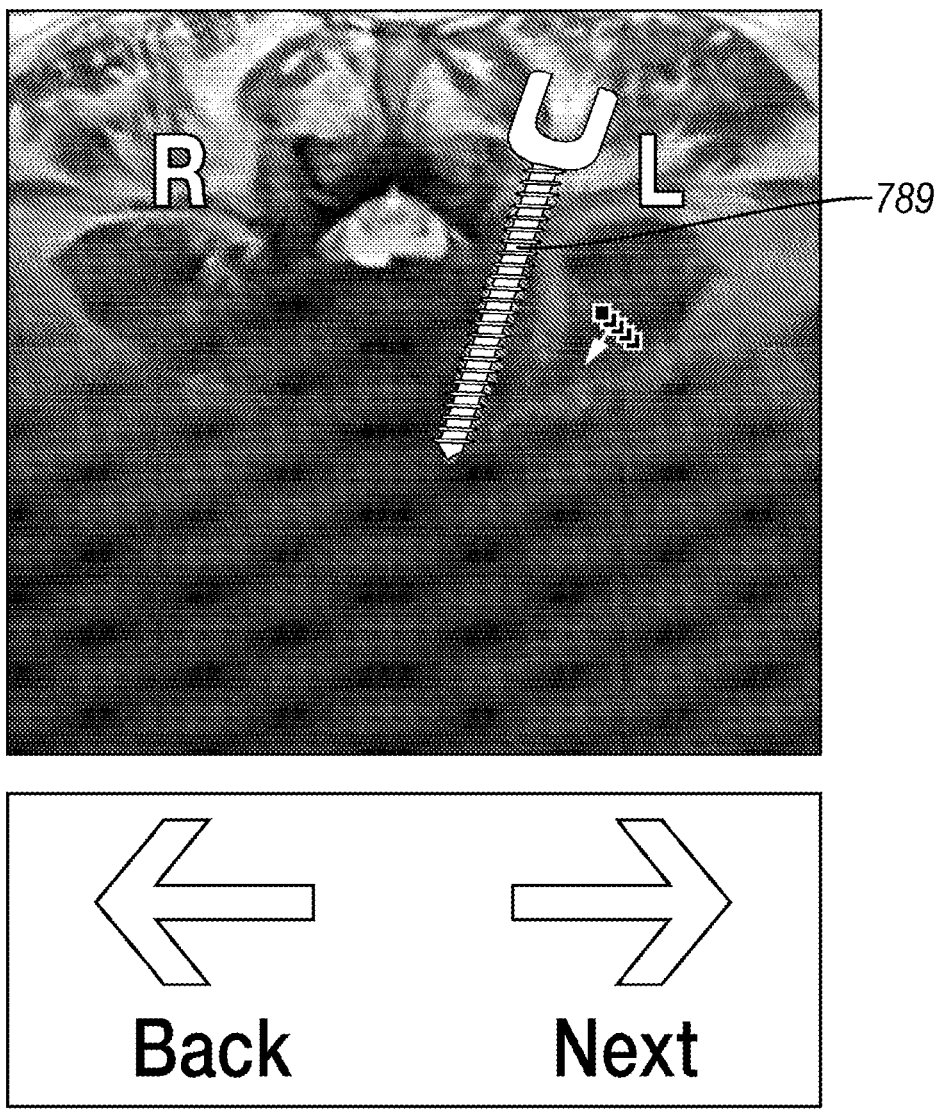
FIG. 12 illustrates a virtual representation presented by the system, such as the medical alignment device or electronic device of FIG. 8, showing an axial view of a vertebra with a proposed alignment position of a pedicle screw shown that includes an insertion point and alignment angle for insertion or installation of the medical device into the bone or vertebra in this plane.

FIG. 12 illustrates a virtual representation presented by the system, such as the medical alignment device or electronic device of FIG. 8, showing a diagnostic image of a vertebra in an axial view with a simulated pedicle screw 789 shown that can be manipulated and moved to set a desired insertion point or location, and a desired alignment angle. Once set, an insertion location and alignment angle are stored, such as by a medical alignment device 300, for this two-dimensional view of the vertebra or object in this plane.

Figure 13B:
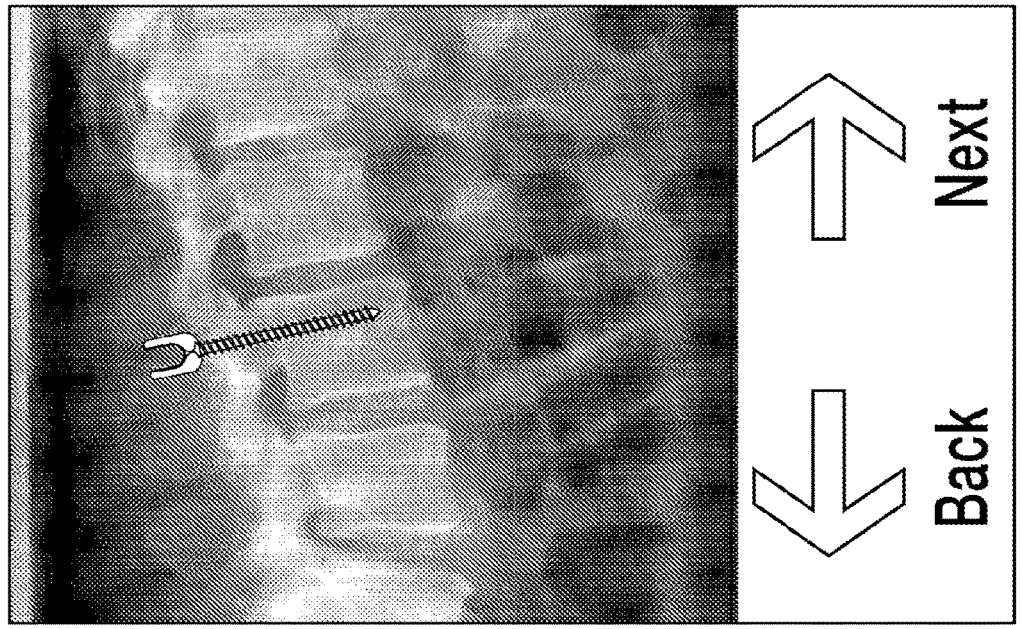
FIGS. 13A and 13B illustrate a virtual representation showing an orthogonal, lateral view of the vertebra and pedicle screw as set in the plane of FIG. 12, with the user able to establish the insertion location and alignment angle of the pedicle screw to be set in this plane so that the system, such as a medical alignment device, now has enough information as to the location of the pedicle screw in two orthogonal planes to determine a three-dimensional alignment angle for the installation of the pedicle screw in this vertebra.
Figure 13A:
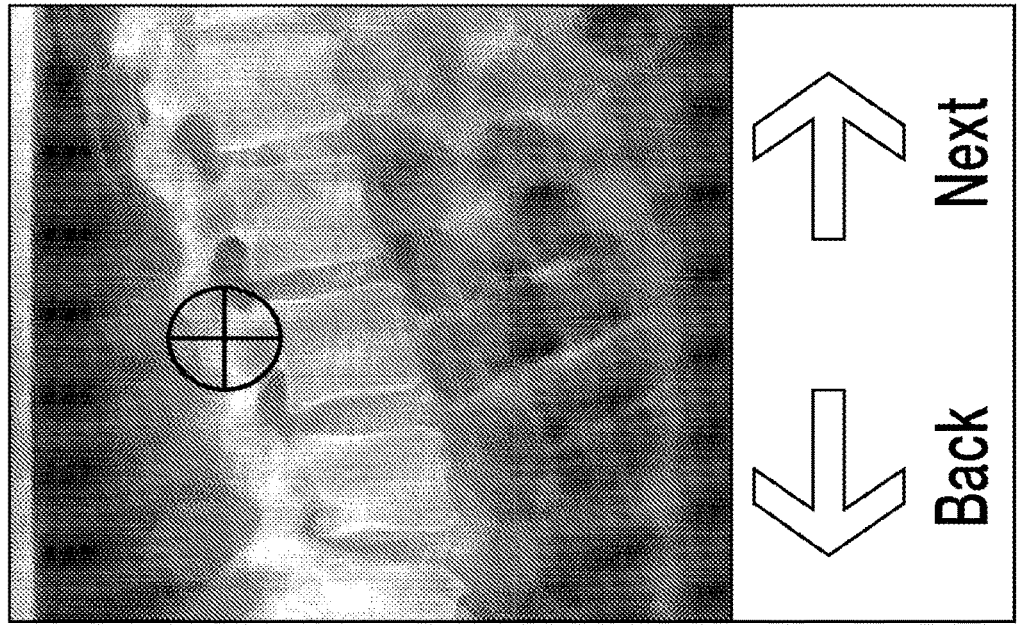

FIGS. 13A and 13B illustrate a virtual representation showing an orthogonal, lateral view of the vertebra and pedicle screw as shown and as set in the plane of FIG. 12, with the user able to establish or set the insertion location and alignment angle of the simulated pedicle screw in this plane so that the system, such as a medical alignment device, now has enough information as to the location of the pedicle screw in two orthogonal planes to determine a three-dimensional alignment angle for the installation of the pedicle screw (or drilling of a pilot hole for the pedicle screw) in this vertebra. FIG. 13A illustrates the cross-hair to set the desired insertion point, while being constrained with the positioning of the pedicle screw as defined in the view of FIG. 12, and, similarly, the angle of the pedicle screw may be set as desired as shown in FIG. 13B, while also being constrained with the positioning of the pedicle screw as set in the view of FIG. 12.

The medical alignment device 300 may calculate a desired three-dimensional alignment angle based on the inputs as just described in connection with FIGS. 12 and 13. The medical alignment device 300, knowing its own orientation, may notify a user, such as a surgeon, when a side, surface, or portion of the medical alignment device 300 is oriented according to the desired three-dimensional alignment angle. Thus, the apparatus 300, which may be referred to as a medical alignment device 300 in certain implementations, may be positioned relative to a tool (such as adjacent to or abutted with) to align the tool to the desired three-dimensional alignment angle. The tool may include, for example, a drill or gear shift probe to create a pilot hole for installing a pedicle screw. The tool, of course, could be any tool to be aligned at a desired three-dimensional angle.

Figure 14:
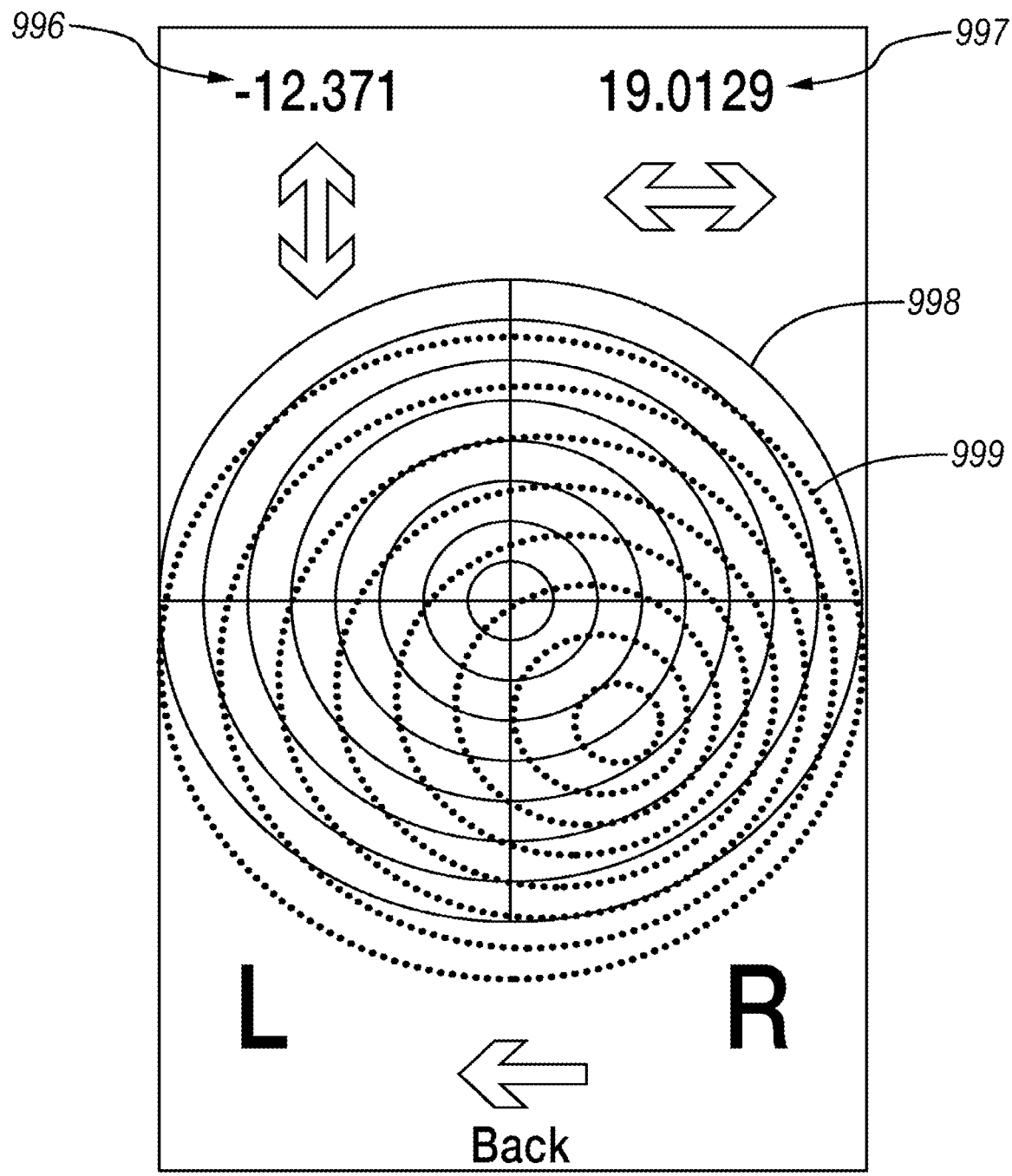
FIG. 14 illustrates an example application of the aligning method presented in FIG. 5A in which the medical device is not properly angled for insertion into the bone.
Figure 15:
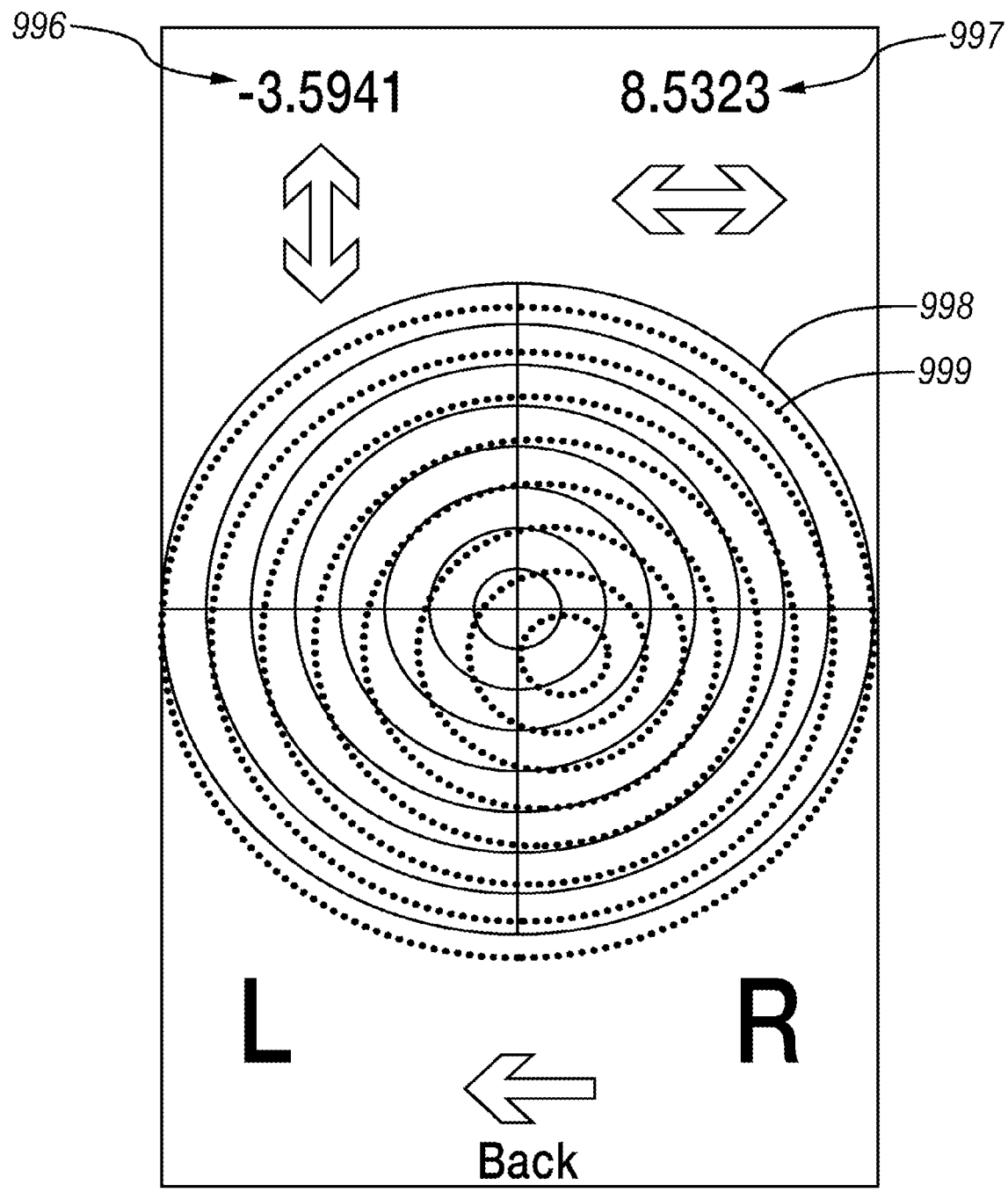
FIG. 15 illustrates an example application of the aligning method presented in FIG. 5A in which the medical device is not properly angled for insertion into the bone, yet is more properly aligned than it was in FIG. 14.
Figure 16:
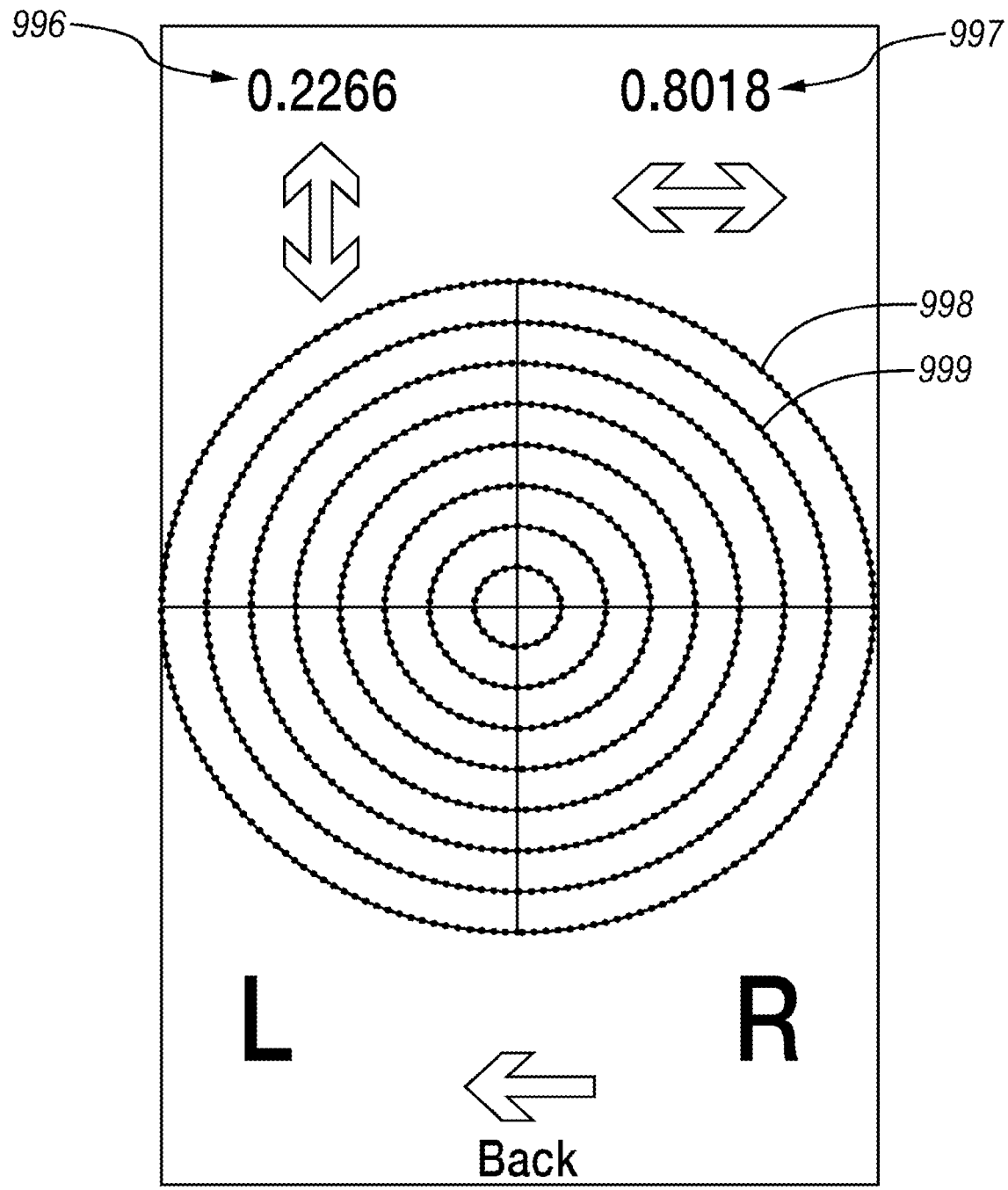
FIG. 16 illustrates an example application of the aligning method presented in FIG. 5A in which the medical device is properly angled for insertion into the bone.

FIGS. 14-16 illustrate a series of two-sets of concentric circles illustrating one embodiment of a graphical indicator or notification showing how the current position of the apparatus 300 is oriented relative to the desired alignment angle. As the orientation of the apparatus 300 is moved or aligned more closely to the desired three-dimensional alignment angle, as illustrated when looking at FIGS. 14-16 consecutively, the concentric circles are moved closer to one another providing a graphical indication or feedback to assist a user or surgeon to align the apparatus 300, and hence an attached or adjacent tool, to the desired alignment angle. Once the apparatus 300 is oriented within a desired threshold close to the three-dimensional alignment angle, an auditory, visual, and/or tactile notification may be provided to alert the user.

Numerical indicators 996 and 997 may also be provided as shown in FIGS. 14-16, along with double arrows adjacent the numerical indicators to denote alignment in each such plane. The apparatus 300 may display numerical differences (or errors) in each of the two planes of the desired alignment angles. The numerical indicators 996 and 997 show how close and in what direction the orientation of the apparatus 300 is positioned relative to the desired alignment angles in each of the two planes or two-dimensions as previously set and stored in the apparatus 300.

For example, FIG. 14 is a sample display of the apparatus 300 with two sets of concentric circles 998 and 999. In one implementation, the set of concentric circles 998 represents the desired three-dimensional alignment angle or orientation, such as the orientation of a pilot hole for a pedicle screw, while the set of concentric circles 999 represents the current three-dimensional orientation of the apparatus 300 showing the current orientation of the apparatus 300. As the apparatus 300 is oriented closer and closer to the desired three-dimensional alignment angle in FIGS. 15 and 16, the set of concentric circles 999 moves closer to the set of concentric circles 998 until the sets of circles are positioned over one another, or within a specified threshold, as illustrated in FIG. 16, to indicate that the apparatus 300 is aligned according to the desired three-dimensional alignment angle.

Similarly, the numerical indicators 996 and 997 in each of their respective planes are shown moving closer to zero, or within a specified threshold, as the apparatus 300 is moved closer and closer to the three-dimensional alignment angle when viewing FIGS. 14-16.

In one implementation, FIG. 15 is a sample display of the apparatus 300 in generating an indicator on the display 310 that indicates a degree of alignment between a tool aligned with a pedicle screw (or pilot hole or tool to install the pedicle screw) and the desired alignment angle, which may include an insertion sagittal angle, transverse angle, and/or coronal angle between an axis of the apparatus 300 and the sagittal plane, transverse plane, or coronal plane of the vertebra. As can be seen in FIG. 15, the indicator is in the form of a first set of concentric circles 998 and a second set of concentric circles 999. As the degree of alignment between the pedicle screw and the insertion sagittal angle, transverse angle, or coronal angle between an axis of the apparatus and the sagittal plane, transverse plane, or coronal plane of the vertebrae changes, the position of the first set of concentric circles 998 and position of the second set of concentric circles changes 999, or the position of one of the sets of the concentric circles 998 or 999 changes with respect to the other.

For example, as shown in FIG. 15, the set of concentric circles 999 is moved and positioned downward and to the right with respect to the set of concentric circles 998. This indicates that the proper alignment has not been found. By reorienting the apparatus 300, which it is noted would be directly or indirectly coupled to the pedicle screw or pilot hole location, in the appropriate direction, the set of concentric circles 999 moves closer to alignment with the set of concentric circles 998, as shown in FIG. 16. Once the proper alignment of the pedicle screw and the desired three-dimensional insertion angle between an axis of the apparatus and the vertebra has been reached, the sets of concentric circles 998 and 999 overlap one another, becoming one and the same, as shown in FIG. 16.

It can be noted that the color of the concentric circles 998 and 999 may be changed to further illustrate the degree of alignment between apparatus 300 and the desired alignment angle. For example, the misalignment indicated in FIG. 14 could be indicated by the set of concentric circles 999 being red, with the set of concentric circles 998 being blue; the better, but still not ideal, alignment indicated in FIG. 15 could be indicated by the set of concentric circles changing from red to yellow; and the ideal alignment indicated in FIG. 16 can be shown with both sets of concentric circles 998 and 999 being green.

It should be appreciated that although concentric circles have been shown, any concentric shapes can be used instead. In addition, concentric shapes need not be used, and any two individual shapes of the same size, or of a different size, may be used. Furthermore, it should be appreciated that in some instances one set of shapes may deform with respect to one another, in other instances both sets of shapes may remain at their original dimensions during operation.

In addition, in some instances, numerical indicators 996 and 997 may indicate the degree of alignment between the apparatus and a desired angle in a plane, a two-dimensional angle, such as the desired insertion sagittal angle, transverse angle, or coronal angle.

Figure 17:
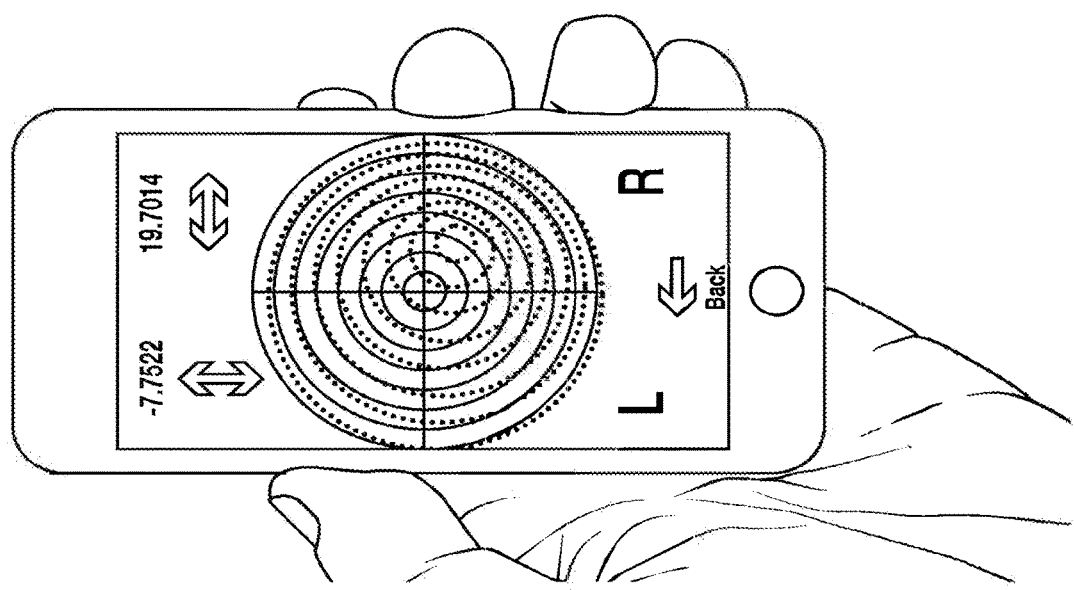
FIG. 17 illustrates the example applications shown in FIGS. 14-16 in operation on a smartphone.

FIG. 17 illustrates the example of implementing the apparatus 300 as a smartphone or smart device application, with the sets of concentric circles and numerical indicators displayed and showing relative alignment of the apparatus 300 with a desired alignment angle, such as was shown in FIGS. 14-16. The apparatus 300 includes orientation circuitry/apparatus, such as a gyroscope, to know its three-dimensional orientation.

Figure 18:
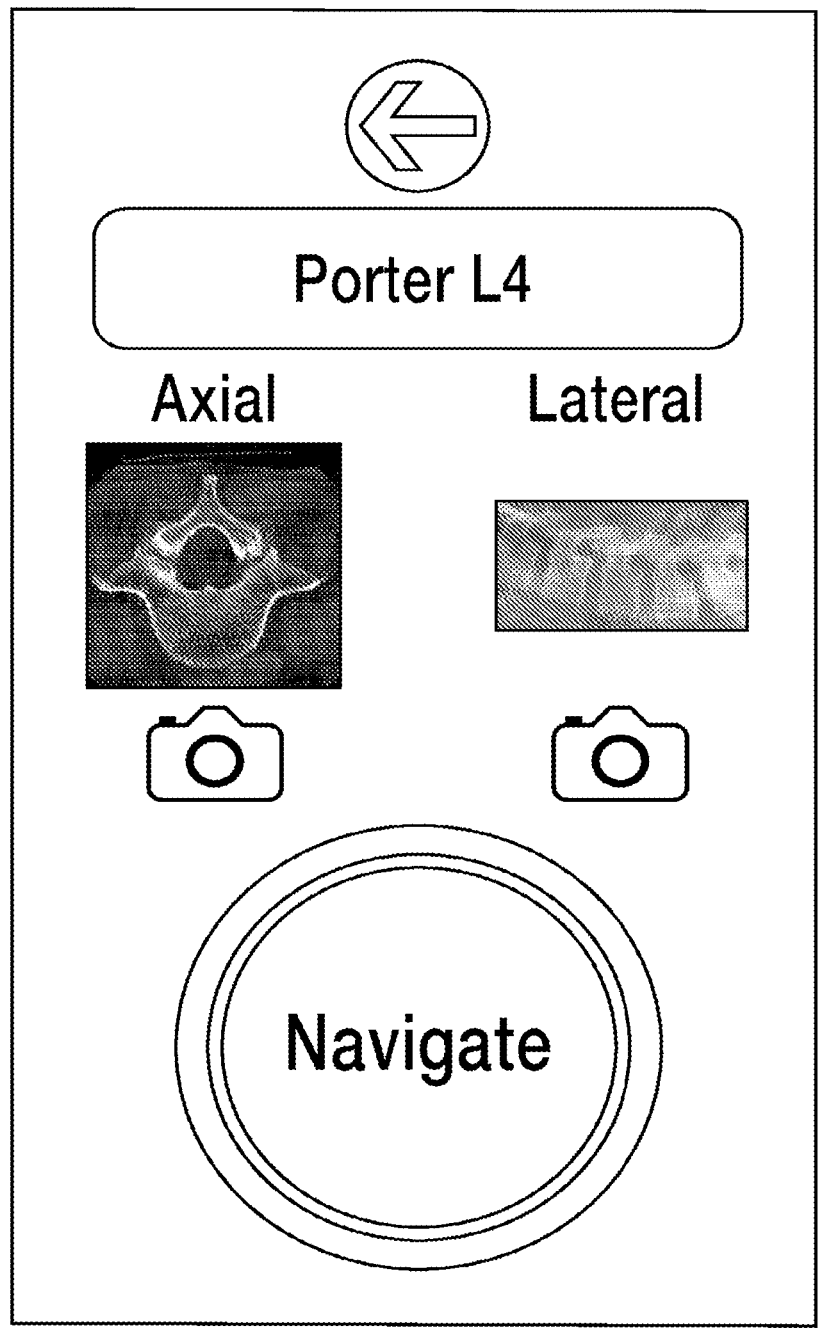
FIG. 18 illustrates a user interface of the device of FIG. 3A in operation when selecting different views of a bone.

Shown in FIG. 18 is a user interface of the apparatus 300 of FIG. 3A in operation when selecting different diagnostic image views of a vertebra that are orthogonal to one another in preparation for establishing desired alignment angles so that the three-dimensional alignment angle may be determined to install a pedicle screw. Also, a patient may be identified, as well as the specific vertebra is identified. The diagnostic images may be provided to the apparatus 300 by digital transmission, or by using a camera of the apparatus 300 to capture these two images of the vertebra that are orthogonal to one another.

Figure 19:
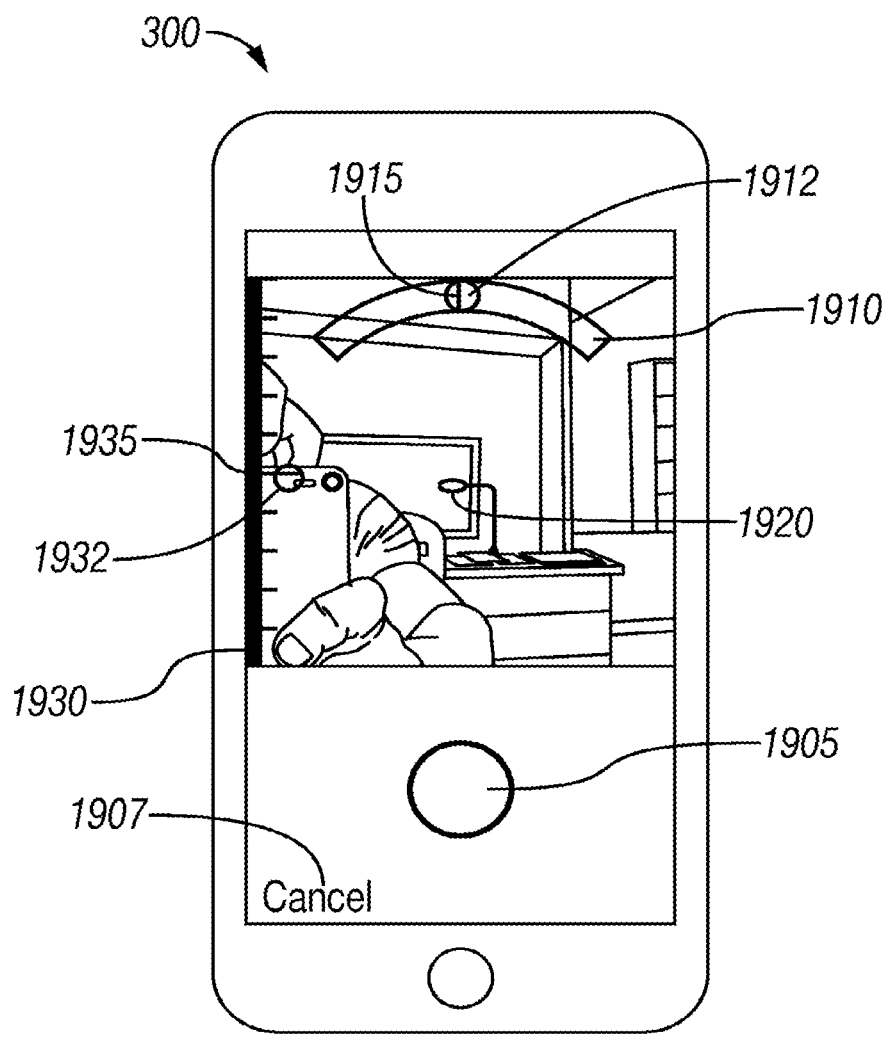
FIG. 19 illustrates a graphical user interface (GUI) of an orientation calibration system when the medical alignment device is properly oriented.

FIG. 19 illustrates a graphical user interface (GUI) of an orientation calibration system implemented using a smart device, such a smartphone, iPhone, iPod Touch, iPad, tablet computer, and the like. For example, the orientation calibration system may be implemented as part of the medical alignment device 300 (also referred to as apparatus 300 or orientation calibration system 300) to ensure that the medical alignment device is properly oriented or aligned when acquiring an image, such as a diagnostic image, appearing on an external display monitor. The diagnostic image may be acquired using a camera (not shown, and located on the other side) of the apparatus 300. The user interface may include a capture button 1905 (which may be thought of, or function as, a shutter button of a digital camera), a cancel button 1907, and an active viewfinder (the display capturing a live or current view using the camera of the device). For example, the diagnostic image to be captured may be displayed on a monitor as shown in the live view in FIG. 19 in the user interface. The display monitor shown in the live view is external to the apparatus 300 and may be referred to as an imaging source 1920. This may be a monitor to display any image, such as for example, a diagnostic medical image such as a CT or MM scan. Inside the viewfinder or display of the apparatus 300, one or more graphical elements, such as dynamic graphical elements, may be provided to aid in displaying the present orientation of the apparatus 300, which may include a gyroscope or some other orientation sensor. In the illustrated example, dynamic graphical element includes a circle 1912 movable in a curved track 1910. The circle 1912 may change its color when the difference between the present orientation of the apparatus 300 and reference orientation is within a threshold value. The curved track 1910 may be indicated with a center position 1915, for which the user is intended to align the circle 1912. The tilt of the apparatus 300 to the left or right, in one implementation, should move the circle in each direction in the curved track 1910. This dynamic graphical element may be referred to as a left/right indicator, alignment, or orientation of the apparatus 300, and detects orientation, rotation, or alignment along, for example, a first axis, such as a "z" axis extending into and out of the page. This determines the position or orientation of the apparatus 300 along at least one axis.

The dynamic graphical element may further include a vertical indicator, such as a vertical gauge 1930 indicating a tilt of the medical alignment device 300 into or out of the page, in one implementation. The vertical gauge 1930 may include a center position 1935 and a circle 1932 movable along or adjacent the vertical gauge 1930. When the center (or some desired portion) of the circle 1932 reaches the center position 1935, the medical alignment device 300 becomes vertical and aligned with the gravitational direction (also referred to as orthogonal to the ground) or some other desired reference direction. This dynamic graphical element may be referred to as an up/down indicator, alignment, or orientation of the apparatus 300, and detects orientation, rotation, or alignment along, for example, a second axis, such as an "x" axis extending left to right on the page (or horizontal to the ground with the ground at the bottom of the page). This determines the position or orientation of the apparatus 300 along at least one axis.

Figure 20:
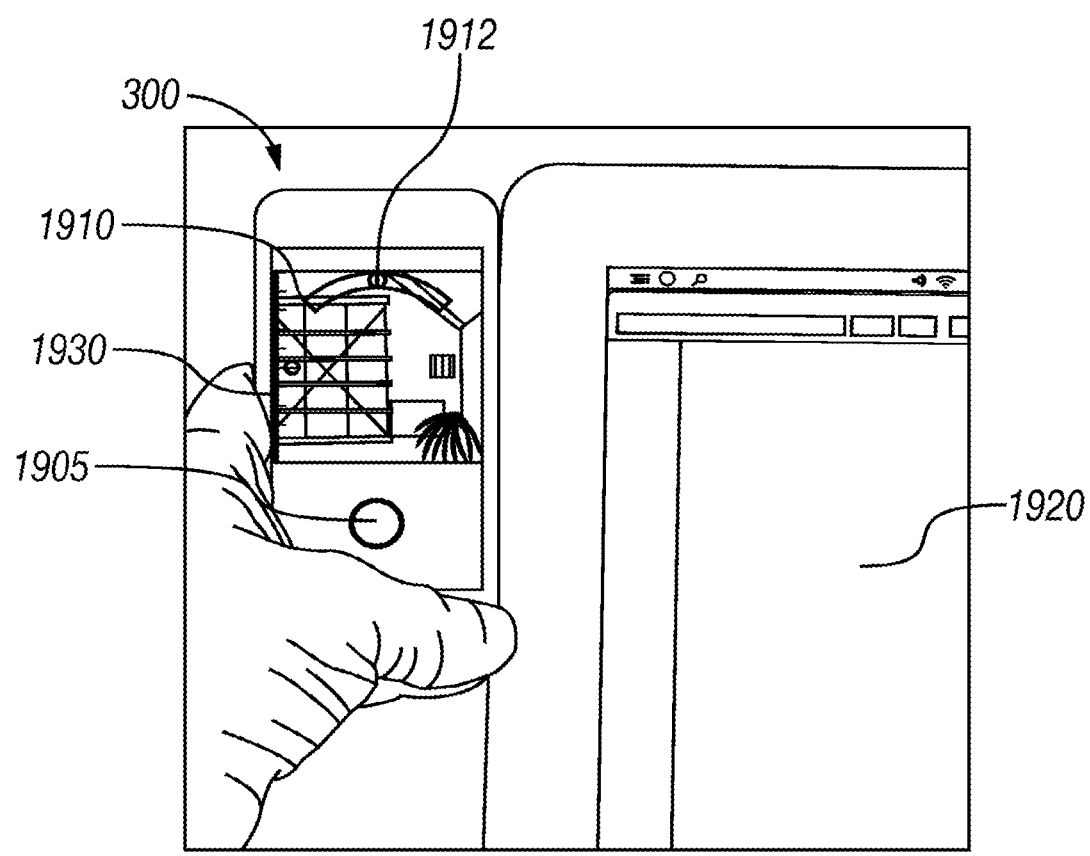
FIG. 20 illustrates an operation of using an orientation calibration system to calibrate an imaging source.

FIG. 20 illustrates an operation of using an orientation calibration system 300 to calibrate or align an imaging source 1920, which may be a computer monitor, external monitor, or any object where a target image is located. In certain applications, such as medical applications, having the imaging source 1920, such as a monitor displaying a diagnostic medical image that will be used in a medical alignment device, the need to ensure that the imaging source 1920 is properly oriented or aligned so that the image is not skewed when taken or captured by the medical alignment device. As shown, the imaging source 1920 is calibrated or adjusted to a desired orientation. This may be achieved by utilizing the orientation sensor of the apparatus 300 with a built in orientation sensor and the dynamic graphical elements described above. This apparatus 300 may be placed adjacent (or abutted against) certain sides, edges, or locations of the imaging source 1920 to ensure that the imaging source may be adjusted and aligned as desired. In one example, the apparatus 300 is first aligned to a known edge or side of the imaging source 1920 such that, in one example, they are coplanar and having at least one edge aligned, adjacent, and/or abutting one another as shown in FIG. 20.

The orientation sensor in the apparatus 300 may be active and shows the present orientation relative to a known reference orientation, such as a calibrated orientation or the ground. In some embodiments, the user may use the present orientation as the calibrated orientation or redefine the calibrated orientation, in certain implementations. The user may adjust the orientation of both the apparatus 300 and the imaging source 1920 to desired position or orientation. In one embodiment, the user desires that the display screen of the imaging source 1920 is perpendicular to the ground and all sides of the imaging source 1920 are orthogonal to one another and to the ground. This may be achieved, in one embodiment by (i) aligning the edge of the apparatus 300 adjacent a straight, left edge of the imaging source 1920, as shown, and adjusting the imaging source 1920 using the circle 1912 and the curved track 1910 until the left edge of the imaging source 1920 is vertical and orthogonal to the ground, and (ii) aligning the back of the apparatus 300 adjacent the flat face (or surface) of the display screen of the imaging source 1920, as shown, and adjusting the orientation of the imaging source 1920 using the circle 1932 and the vertical gauge 1930 until the face of the display screen of the imaging source 1920 is vertical and orthogonal to the ground. As such, two axes of rotation are aligned, and the imaging source 1920 may display a target image, such as a medical diagnostic image, that is positioned orthogonal to the ground. The apparatus 300 may then be used to capture or take a picture of that image displayed on the imaging source 1920 while the apparatus 300 itself, including the camera of the apparatus 300, is positioned orthogonally to the ground as well. This enhances the accurate capture of such target image, and reduces skew or errors, which are often not readily visible, that are introduced by capturing images at angles that are not properly aligned.

In some embodiments, a default orientation may be used, such as one of the sagittal plane, the transverse plane, the coronal plane, or planes orthogonal to the ground. The user may report the calibrated orientation by noting the relative positions between the circle 1912 and the curved track 1910, in the circle 1932 and the vertical gauge 1930. If the apparatus 300 captures the target image from the imaging source 1920 at the same default orientation, an accurate target image may be obtained.

Figure 21:
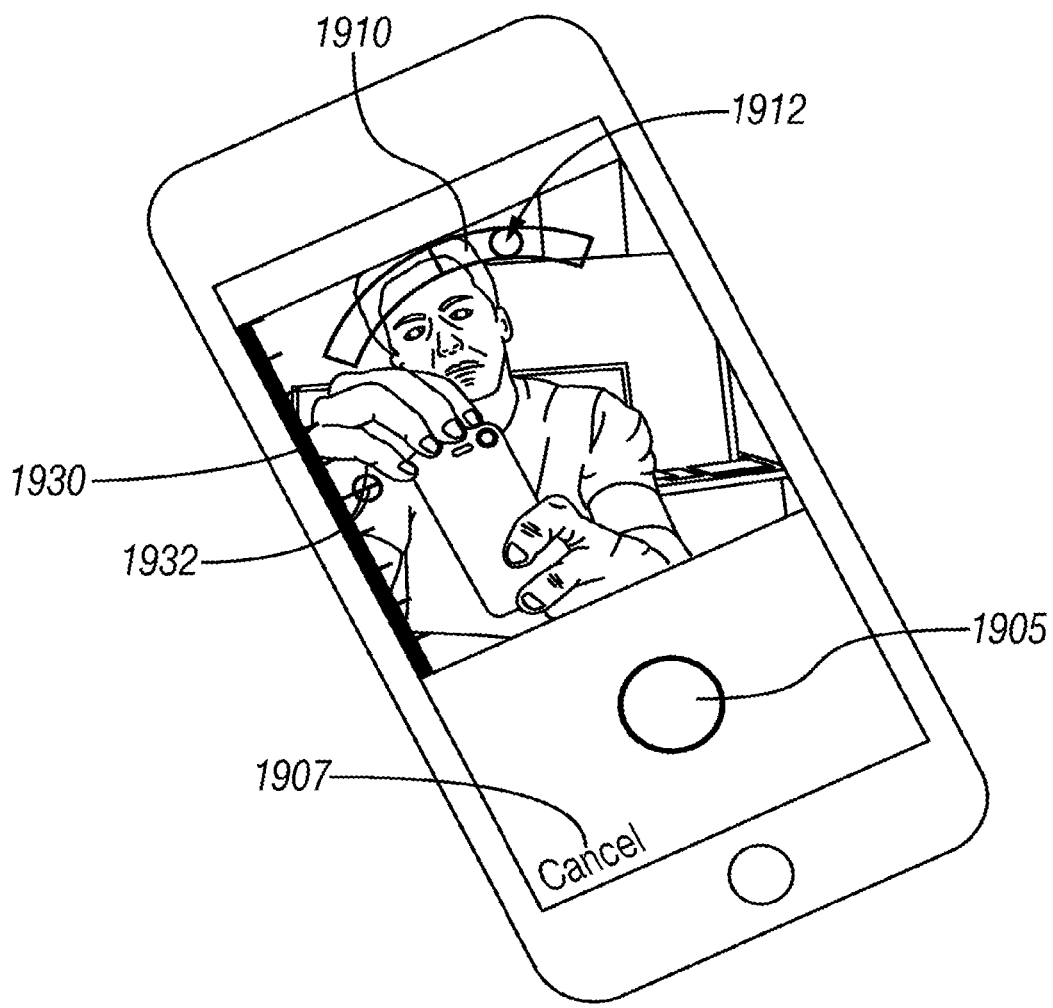
FIG. 21 illustrates a GUI of an orientation calibration system when the medical alignment device is out of the proper orientation.

FIG. 21 illustrates a GUI, such as that shown in FIG. 19, of an orientation calibration system when the medical alignment device 300 (which may also be referred to as the apparatus 300 or the orientation calibration system 300) is out of the proper or desired orientation. Because the apparatus 300 is shown tilted to the "left" on the page while positioned on a flat surface parallel to the ground, for example, the circle 1912 is far away from the center 1915 on the track 1910 indicating the "left" orientation of the apparatus 300, while the circle 1932 is positioned in the middle or adjacent the center position of the vertical gauge 1930 indicating that the back surface of the apparatus 300 is orthogonal to the ground. If the apparatus was tilted to the "right", the circle 1912 would be on the other side from the center 1915 on the track 1910 indicating the "right" orientation of the apparatus 300 in such a case.

Once the imaging source 1920 is properly oriented, a user may use the apparatus 300 to capture a target image displayed on the imaging source 1920. In doing so, it is important that the apparatus 300, which includes a camera, is properly aligned when capturing such target image. Thus, the same alignment tools of the apparatus 300 used to align and properly orient the imaging source 1920, including the dynamic graphical elements such as the circle 1912 and the curved track 1910 as well as the circle 1932 and the vertical gauge 1930, may be used to ensure that the apparatus 300 itself is properly oriented before the target image is captured by the apparatus 300. It should be understood that the present disclosure is not limited to the specific dynamic graphical elements illustrated herein, and that any number of other dynamic graphical elements may be used to ensure a desired orientation or alignment of the apparatus 300. For example, the curved track 1910 may be a straight track.

Figure 22:
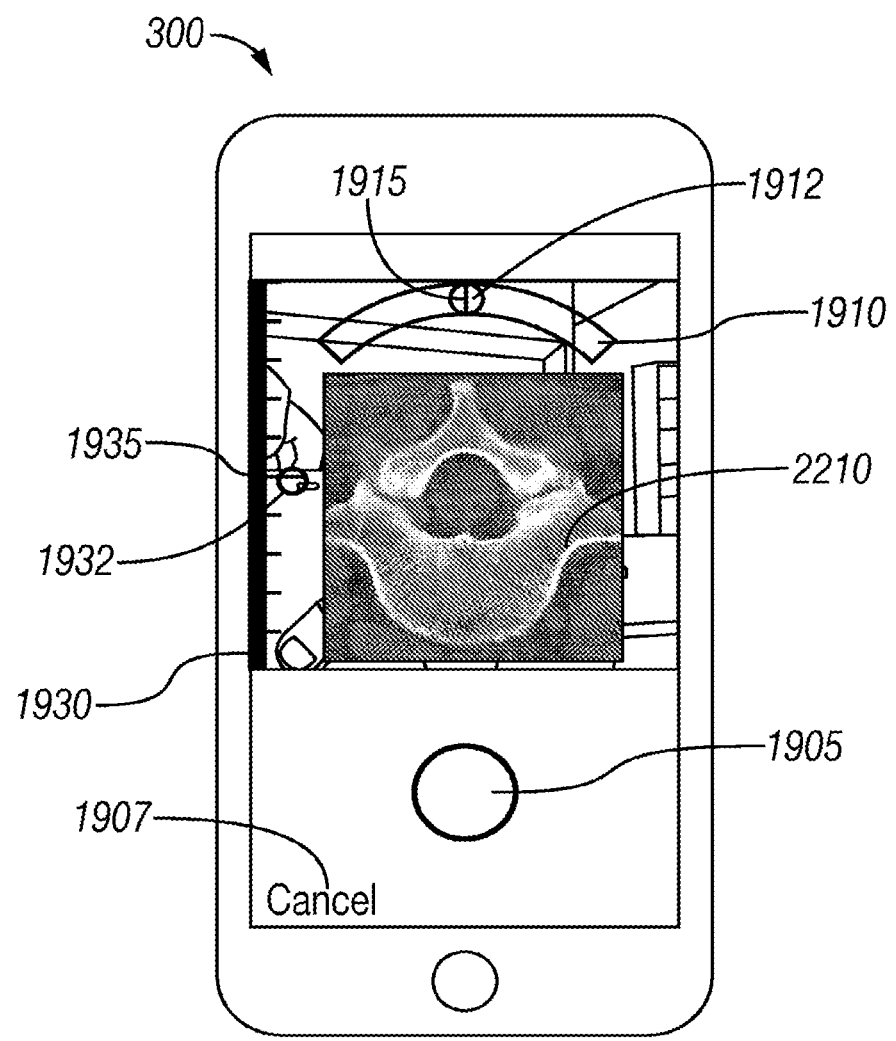
FIG. 22 illustrates an operation of using an orientation calibration system to capture a reference image from an imaging source.

FIG. 22 illustrates an operation of using the orientation calibration system 300 to capture a target image, which may also be referred to as a reference image 2210, from an imaging source, such as a display or monitor with a diagnostic image being displayed. For example, when the apparatus 300 is properly oriented, such as when the circle 1912 reaches a predetermined range or threshold near or adjacent the center 1915, and when the circle 1932 reaches a predetermined range or threshold of the center 1935, the reference image 2210 may be captured by the camera of the apparatus 300. In some embodiments, the processor of the medical alignment device 300 can automatically capture the reference image 2210 when alignment is achieved. In some other embodiments, in response to the alignment, a user can capture the reference image 2210 by pressing the capture button 1905. If a capture reference image 2210 is not satisfactory, a user may cancel to capture reference image 2210 by operation of the cancel button 1907.

Figure 23:
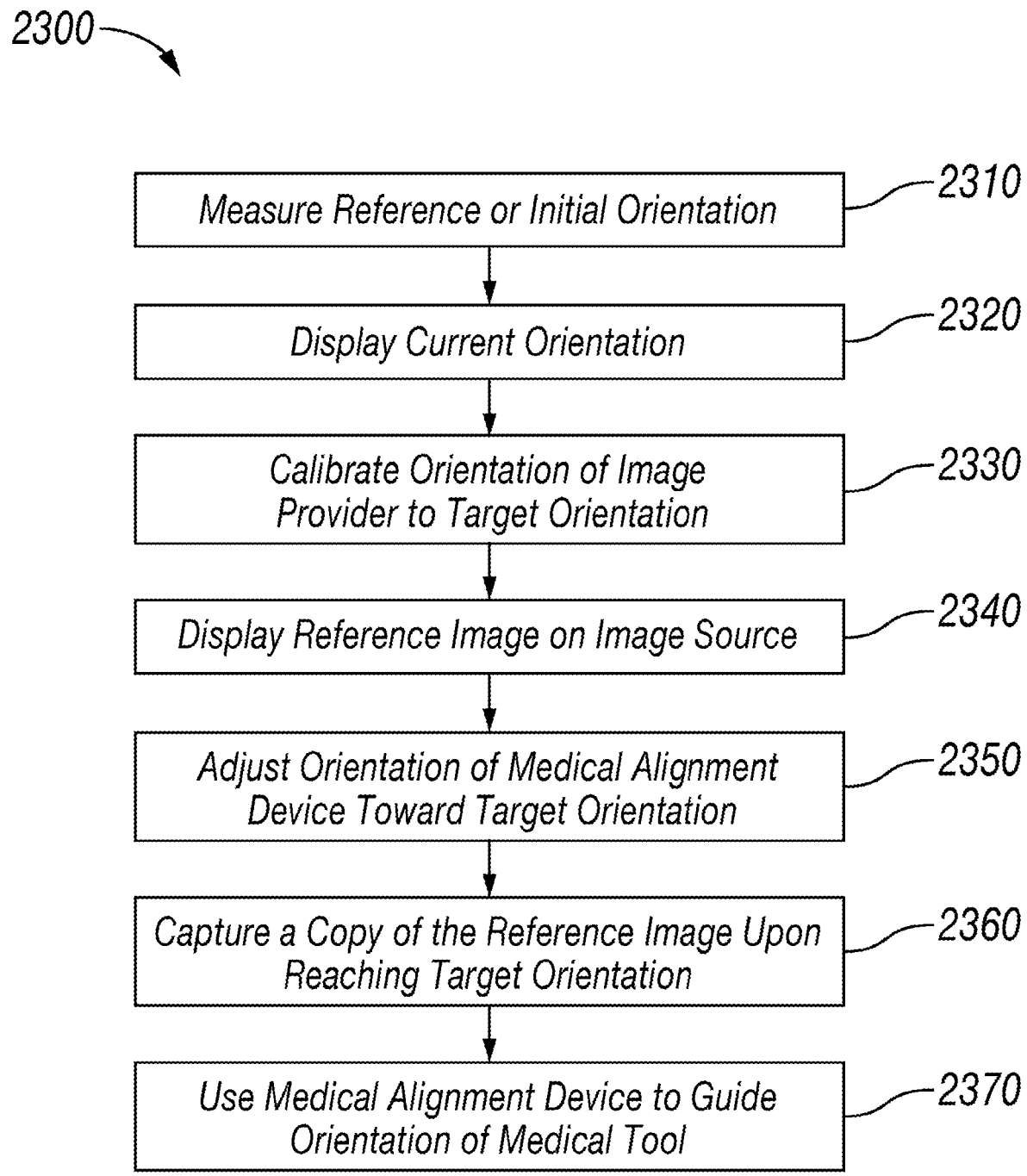
FIG. 23 is a flowchart showing an example of an orientation calibration process.

FIG. 23 is a flowchart 2300 showing an example of an orientation calibration process that may include one or more of a method for orienting a system for capture of a target image (or reference image), and a method for using an orientation calibration system to align a display monitor in an orthogonal position relative to the ground.

At 2310, the reference or initial orientation is measured. For example, the reference orientation may be an initial orientation recorded by the orientation sensor of the medical alignment device 300. Some embodiments, the reference orientation may be a specific orientation defined by the user relative to a known reference frame. Subsequent measurement of the orientation change by the orientation sensor may be made with reference to the measured reference orientation. In one embodiment, the reference orientation is already set and does not have to be set each time, and this may include a first axis orthogonal to the ground (a gravitational vector axis), with two additional axis each orthogonal to each other and each orthogonal to the first axis. This may be visualized as an x,y,z cartesian coordinate system in three-dimensional space.

At 2320, the current orientation of the apparatus 300 is displayed on a display screen of device, which may be an orientation calibration system or a medical alignment device, which we will use in describing the flowchart 2300. In some embodiments, the current orientation may be displayed when other visual devices, wirelessly or by cable, are in communication with the medical alignment device. The current orientation may be represented by a dynamic graphical representation, such as a circle moving along a track or gauge or numerically. The current orientation of the medical alignment device may be shown, in one implementation, as two or three axis of rotation, and this information is provided by an orientation sensor using a gyroscope in the medical alignment device 300.

At 2330, the user calibrates the orientation of the imaging source, which may be a computer monitor, to a target orientation. For example, the target orientation may be the sagittal plane, the transverse plane, and the coronal plane, or orthogonal to the ground along a side edge, and parallel to the ground along a top or bottom edge.

At 2340, a reference image or target image is displayed by the imaging source, such as a display monitor. For example, an imaging source may be connected to a CT scanner that provides images of a patient. In some other embodiments, the imaging source may be connected to a database storing images of the patient.

At 2350, orientation of the medical alignment device 300 is adjusted to the target orientation so that when the target image is captured by the camera of the apparatus 300, the image will not be distorted or skewed. For example, a user may hold the medical alignment device 300 and view the dynamic graphical representations of its current orientation on its display, such as by tracking the circles along a curved track or the vertical gauge as shown in FIGS. 19-22, until a camera of the medical alignment device 300 is properly aligned in front of the target image to properly capture such image being displayed by the imaging source.

At 2360 when a target orientation is reached, a copy of the reference or target image may be captured by the medical alignment device. For example, the processor of the medical alignment device 300 may capture the reference image automatically when the target orientation is reached. In other instances, a user may provide a command to capture the reference image in response to reaching the target orientation. The command may be by touch, may be by voice, and may include other sources of inputs.

At 2370, the now calibrated medical alignment device 300, in certain implementations, may be ready to guide orientation of the medical tool, for example, as discussed in FIG. 7.

B. Systems and Methods for Capturing and Analyzing Photos for Calculating and Determining Optimal or Desired Placement of Posterior Fixation Placement Implementations of the systems and methods discussed above provide for accurate measurement of relative orientations between a medical alignment device and a patient, and avoids a mistaken reading of the relative angle as measured by the orientation sensor between the medical alignment device and the reference image, thus enabling accurate subsequent alignment indications. However, these systems and methods may require the physician to have identified optimal or desired placement of the medical alignment device in advance.

In a further implementation, a machine learning-based or artificial intelligence-based system may be trained on data from historical placement of medical alignment devices, captured via the orientation systems and methods discussed above, and may automatically identify and suggest optimal or desired placement positions and orientations. The physician may then utilize the orientation system to match the identified or suggested placement position and orientation, both for training purposes and for accurate placement of devices in patients. The system may also be improved via a supervised learning process as the physician accepts or rejects the suggested placement position and orientation, with the machine learning system adjusting weights of a model accordingly.

Figure 24:
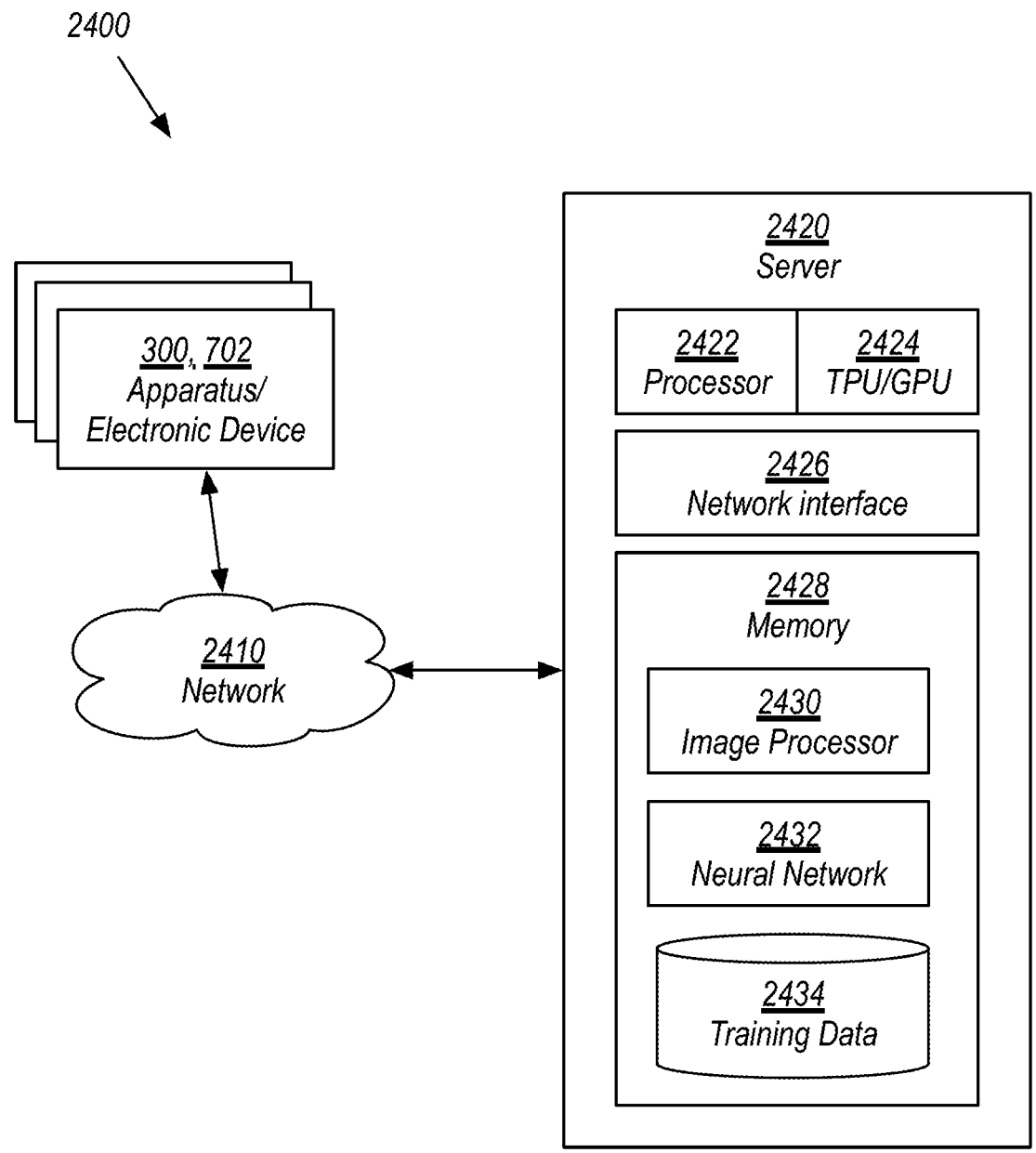
FIG. 24 is a block diagram of an implementation of a system for calculating and determining placement of posterior fixation placement.

FIG. 24 is a block diagram of an implementation of a system 2400 for calculating and determining optimal or desired placement of posterior fixation placement. An apparatus or electronic device, such as apparatuses 300 and electronic devices 702 discussed above, may communicate via a network 2410 with a server 2420. Server 2420 may comprise one or more computing devices, including servers, workstations, appliances, clusters or farms of servers, virtual computing devices (e.g. clouds) executed by one or more physical computing devices, or any other type of computing device for receiving and processing captured images and identifying optimal or desired alignment device placement, and may be referred to as a server, cloud service, neural network processor, machine learning system, or by similar terms. Although shown separate from apparatuses 300 and electronic devices 702, in many implementations, one or more functions of server 2420 may be incorporated in the apparatuses and/or electronic devices (e.g. image processing, classification or analysis of images via a neural network, etc.). For example, in some implementations to reduce network latency issues, a server 2420 may train a neural network based on captured images of device placement, and then provide nodal weights and coefficients or other hyperparameters to an apparatus 300 or electronic device 702 for subsequent post-training analysis or classification of new images.

Network 2410 may comprise any type and form of communications network or networks, including local area networks (LANs), wide area networks (WANs) such as in the Internet, virtual private networks, cellular networks, broadband networks, satellite networks, or any other type and form of communications network or combinations of these or other networks. In many implementations, network 2410 may comprise additional devices not illustrated, such as one or more switches, gateways, routers, firewalls, network accelerators, caches, load balancers, or other such devices.

Server 2420 may comprise one or more processors 2422. A processor 2422, sometimes referred to as a central processing unit or CPU, may comprise one or more logic circuits that respond to and process instructions. Thus, CPUs provide flexibility in performing different applications because various instructions may be performed by the CPU. In many implementations, the processor or processors 2422 may be provided by one or more microprocessor units, such as those manufactured by Intel Corporation of Mountain View, California; those manufactured by International Business Machines of White Plains, New York; or those manufactured by Advanced Micro Devices of Sunnyvale, California. One or more algorithmic logic units (ALU) may be incorporated in processors to perform necessary calculations in the event an instruction requires a calculation be performed. When a CPU performs a calculation, it performs the calculation, stores the calculation in memory, and reads the next instruction to determine what to do with the calculation. Although shown as a single processor 2422, in many implementations, a server 2420 may comprise a plurality of processors 2422, including parallel processors, co-processors, or other processors. Furthermore, in some implementations, processor 2422 may comprise one or more virtual processors (e.g. vCPUs) provided by a virtual machine managed by a hypervisor of a physical computing device and deployed as a service or cloud or in similar architectures.

Server 2420 may comprise additional specialized processors, such as a graphics processing unit (GPU) or tensor processing unit (TPU) 2424. A GPU may comprise a specialized electronic circuit designed to quickly perform calculations and access memory. As GPUs are specifically designed to perform calculations quickly, GPUs may have many ALUs allowing for parallel calculations. Parallel calculations allow calculations to be performed more quickly. GPUs, while specialized, are still flexible in that they are able to support various applications and software instructions. As GPUs are still relatively flexible in the applications they service, GPUs are similar to CPUs in that GPUs perform calculations and subsequently store the calculations in memory as the next instruction is read. A TPU, while still a processor like a CPU and GPU, is an Artificial Intelligence application-specific integrated circuit. TPUs may not include on-board memory circuits, in many implementations, and may instead comprise a large number of ALU circuits to perform computations quickly. A TPU may perform calculations under the direction of a CPU and subsequently passes the calculations to an ALU of the CPU or GPU or output the calculations such that more calculations may be performed. Thus, TPUs may be faster than their counterpart CPUs and GPUs.

Server 2420 may comprise one or more network interfaces 2426 for communicating via a network 2410 with apparatuses 300, electronic devices 702, or other servers 2420 or devices (not illustrated) through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, IEEE 802.11ac, IEEE 802.11ad, CDMA, GSM, WiMax and direct asynchronous connections). In one embodiment, the server 2420 communicates with other computing devices 300, 702, 2420 via any type and/or form of gateway or tunneling protocol such as Secure Socket Layer (SSL) or Transport Layer Security (TLS). The network interface 2426 may include a built-in network adapter, network interface card, PCMCIA network card, card bus network adapter, wireless network adapter, USB network adapter, modem or any other device suitable for interfacing the server 2420 to any type of network capable of communication and performing the operations described herein.

Server 2420 may comprise one or more memory or storage devices 2428, referred to generally as memory 2428. Memory 2428 may comprise one or more memory chips capable of storing data and allowing any storage location to be directly accessed by the processor 2422 and/or GPU or TPU 2424, such as any type or variant of Static random access memory (SRAM), Dynamic random access memory (DRAM), Ferroelectric RAM (FRAM), NAND Flash, NOR Flash and Solid State Drives (SSD). The memory 2428 may be based on any of the above described memory chips, or any other available memory chips capable of operating as described herein. Memory 2428 may also comprise one or more storage devices, such as hard drives, solid state drives (SSDs) including flash memory devices, optical drives, or any other type and form of data storage device. Although shown internal to server 2420, in many implementations, memory 2428 may be external, such as network attached storage, bus attached storage, or any other type and form of storage device or devices.

Server 2420 or a processor 2422 of a server may execute an image processor 2430. Image processor 2430 may comprise an application, service, server, daemon, routine, or other executable logic for receiving and processing images from sensors or cameras of apparatuses 300 and/or electronic devices 702 or other devices, including MRIs, CT scans, X-rays, or other images. In many implementations, image processor 2430 may be configured to identify a type of image, e.g. based on a bit depth or number of levels of gray of an image. For example, in many implementations, an MRI may have a bit-depth of 12 or 4095 levels of gray (or 10 bits or 1023 levels, in some implementations), while a CT image may have a bit-depth of 8 or 255 levels of gray. Based on the bit depth, the image processor may be able to determine the source or type of image.

Image processor 2430 may be configured to identify a largest area of homogeneity within an image, or a largest region having pixels with similar brightness or gray levels. This may be done by, for example, by counting contiguous regions of pixels having the same brightness level. In some implementations, to account for minor variations in pixel brightness, a bit depth of the image may be reduced by a predetermined amount with pixel brightness rescaled to predetermined levels (e.g. pixels having a brightness value between 100-120 being scaled to 110; those having a brightness value between 121-140 being scaled to 130; etc.). In another implementation, a resolution of the image may be reduced, with larger pixels replacing groups of smaller pixels and having a brightness equal to an average of the smaller pixels; contiguous regions may then be determined from the larger pixels' brightness, reducing minor variations across the image. In another implementation, a low-pass or noise filter may be applied to the image to reduce minor variations, with the resulting filtered image checked for contiguous regions with the same brightness. In some implementations, multiple of these techniques may be applied (e.g. noise filtering the image, and then reducing a bit depth of the image and counting the number of contiguous pixels with the same scaled brightness).

Figure 25A:
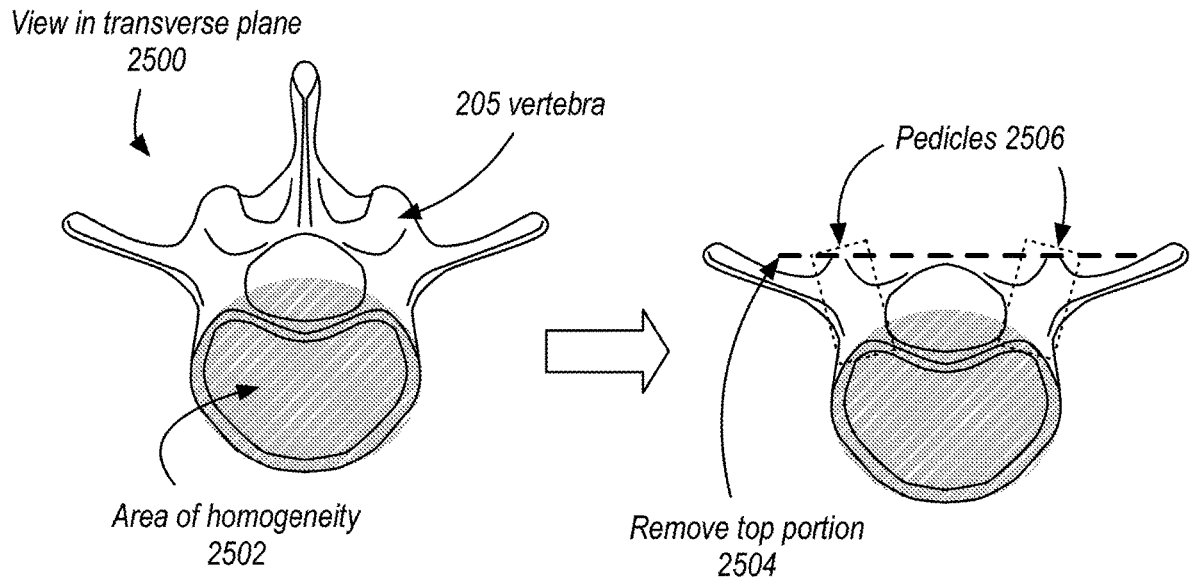
FIGS. 25A-25B are illustrations of an implementations of a process for processing captured images for calculating and determining placement of posterior fixation placement.

Once the largest area of homogeneity is identified, regions laterally adjacent to the area may be identified as pedicles, in some implementations. For example, referring to FIG. 25A, illustrated is an implementation of a process for processing captured images for calculating and determining optimal or desired placement of posterior fixation placement. A vertebra 205 is shown in cross section in the transverse plane 2500. A largest area of homogeneity 2502, corresponding to the vertebral body, may be identified as discussed above. A top portion of the image 2504 above the identified area 2502 may be removed or cropped, and pedicles defined as regions 2506 within the image lateral to the area of homogeneity. The pedicles may be bounded by edges detected by the image processor (e.g. edges corresponding to an edge between the vertebra and a background, which may typically have high relative contrast in MRI or CT images, such as a border between white bone and a dark background). Any sort of edge detection algorithm may be utilized, such as a Sobel or Laplacian filter.

Returning to FIG. 24, server 2420 or a processor 2422 of a server may execute a neural network 2432 or other machine learning system (e.g. a k-Nearest Neighbor classifier, a random forest classifier, etc.). A neural network may comprise an application, service, server, daemon, routine, or other executable logic for identifying relationships for a given set of inputs. Neural networks may be embodied in hardware (e.g. a TPU), software, or a combination of hardware and software. Various types of neural networks exist. For example, modular neural networks include a network of neural networks, each network may function independently to accomplish a sub-task that is part of tasks in a larger set. Breaking down tasks in the manner decreases the complexity of analyzing a large set of data. In some implementations, convolutional neural networks may be utilized because convolutional networks are inherently strong in performing image-based classifications. Convolutional neural networks are particularly suited for image-based classification because the networks take advantage of the local spatial coherence of adjacent pixels in images.

Convolutional layers may detect features in images via filters. The filters may be designed to detect the presence of certain features in an image. In a simplified example, high-pass filters detect the presence of high frequency signals. The output of the high-pass filter are the parts of the signal that have high frequency. Similarly, image filters may be designed to track certain features in an image. The output of the specifically designed feature-filters may be the parts of the image that have specific features. In some embodiments, the more filters that may applied to the image, the more features that may be tracked.

Two-dimensional filters in a two-dimensional convolutional layer may search for recurrent spatial patterns that best capture relationships between adjacent pixels in a two-dimensional image. An image, or an array mapping of an image, may be input into the convolutional layer. The convolutional layer may detect filter-specific features in an image. Thus, convolutional neural networks use convolution to highlight features in a dataset. For example, in a convolutional layer of a convolutional neural network, a filter may be applied to an image array to generate a feature map. In the convolutional layer, the filter slides over the array and the element by element dot product of the filter and the array is stored as a feature map. Taking the dot product has the effect of reducing the size of the array. The feature map created from the convolution of the array and the filter summarizes the presence of filter-specific features in the image. Increasing the number of filters applied to the image may increases the number of features that can be tracked. The resulting feature maps may subsequently be passed through an activation function to account for nonlinear patterns in the features. Various activation functions may be employed to detect nonlinear patterns including nonlinear sigmoid functions, hyperbolic tangent functions, or rectifier linear functions. The output of a convolution layer in a convolutional neural network is a feature map, where the values in the feature map may have been passed through a rectifier linear activation function. In some embodiments, the number of convolutional layers may be increased. Increasing the number of convolutional layers increases the complexity of the features that may be tracked. In the event that additional convolutional layers are employed, the filters used in the subsequent convolutional layers may be the same as the filters employed in the first convolutional layer. Alternatively, the filters used in the subsequent convolutional layers may be different from the filters employed in the first convolutional layer.

The extracted feature map that has been acted on by the activation function may subsequently be input into a pooling layer. A pooling layer down-samples the data to allow the neural network to retain relevant information while reducing the amount of processing required. While having an abundance of data may be advantageous because it allows the network to fine tune the accuracy of its weights, large amounts of data may cause the neural network to spend significant time processing. Down-sampling data may be important in neural networks to reduce the computations necessary in the network. A pooling window may be applied to the feature map. In some embodiments, the pooling layer outputs the maximum value of the data in the window, down-sampling the data in the window. Max pooling highlights the most prominent feature in the pooling window. In other embodiments, the pooling layer may output the average value of the data in the window. In some embodiments, a convolutional layer may succeed the pooling layer to re-process the down-sampled data and highlight features in a new feature map.

In some embodiments, the down-sampled pooling data may be further flattened or arranged into a one-dimensional vector before being input into fully connected layers of the convolutional neural network. In some implementations, the fully connected layer may only have one set of neurons, while in other implementations, the fully connected layer may have an input layer, one or more hidden layers, and an output layer. Neurons within the fully connected layers may be connected to each other by edges having weights or coefficients. During training, the weights are adjusted to strengthen the effect of some neurons and weaken the effect of other neurons. The adjustment of each neuron's strength allows the neural network to better classify outputs. In some implementations, the number of neurons in the neural network may be pruned during training: the number of neurons that are active in the neural network may be adaptively modified as the neural network leans how to classify the output.

After training, the error between the predicted values and known values may be so small that the error may be deemed acceptable and the neural network does not need to continue training. In these circumstances the value of the weights that yielded such small error rates may be stored and subsequently used in testing and analysis, including by other devices executing the neural network.

Figure 25B:
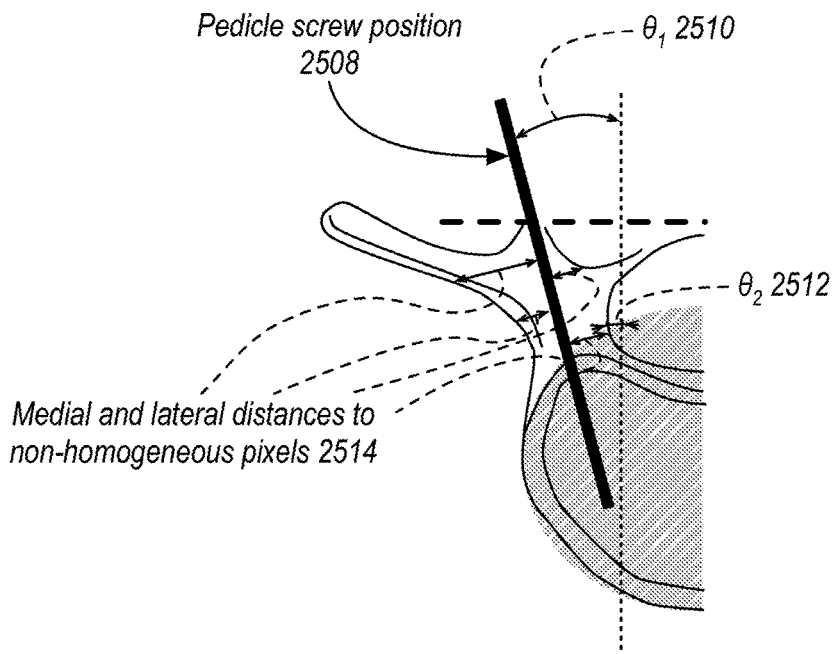
Figure 25C:
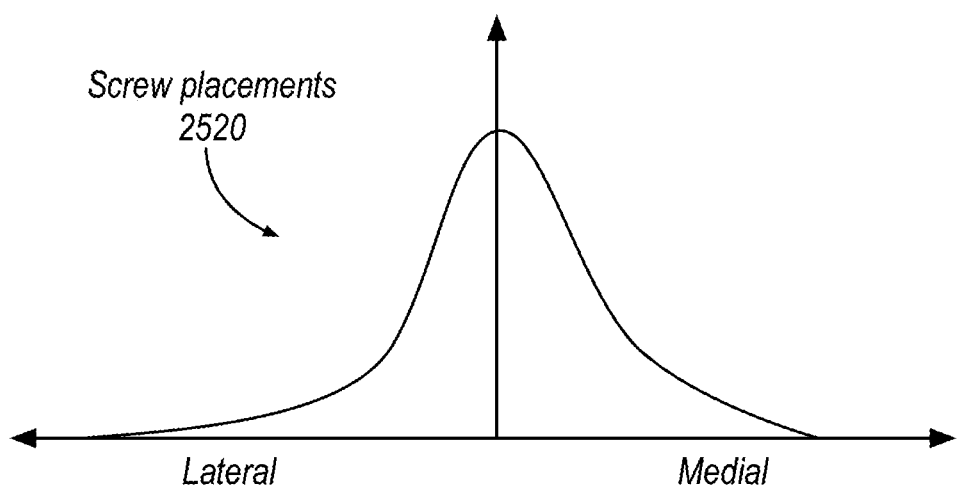
FIG. 25C is a graph of an example of historical placement positions, according to some implementations.

As discussed above, implementations of the orientation systems discussed herein may be utilized with physician-selected positions for medical alignment devices, and may record both the selected or intended position and orientation of the alignment device, as well as the actual position and orientation of the alignment device once installed (which may be more or less accurate relative to the selected position). The selected positions, as well as the installed positions, and the image data from corresponding CT and MRI scans or other captures may be utilized as training data 2434 for the neural network, and may be transmitted from apparatuses 300 and devices 702 to the server 2420 for storage in memory 2428 and analysis and training. For example, referring to FIG. 25B, illustrated is an enlarged portion of a transverse view of a vertebra 205, showing a pedicle screw position 2508. The position 2508 may be determined via image analysis of a CT or MM or other capture and edge detection of an inserted pedicle screw after surgery; may be determined via recorded position and orientation sensing during installation of the screw as discussed above; and/or may be determined via a position and orientation of a virtual pedicle screw by a physician before surgery. Sensor data and/or image analysis data may comprise identifications of relative positions of the screw or other medical device from the medial and lateral walls of the pedicle 2514, which may be measured at one or more predetermined locations such as the top, middle, or bottom of the pedicle (including one medial and lateral measurement, two medial and lateral measurements, three medial and lateral measurements, etc.); as well as measurements of the angle of the screw relative to the pedicle (which may be determined, e.g. as a difference between an angle $\theta_1$ 2510 of the screw to a vertical axis (shown in dotted line) and an angle $\theta_2$ 2512 of the pedicle to the vertical axis). In some implementations, medial and lateral distances 2514 may be measured as percentages of the distance from the center of the pedicle to the edge of the pedicle (e.g. with a perfectly centered screw being 0%, and medial and lateral offsets being values between −100% and 100%, or any other such range). For example, FIG. 25C is a graph of an example of historical lateral and medial pedicle screw placement positions 2520 within a pedicle, according to some implementations. As shown, while the majority of placements may be close to the center of the pedicle, some may be offset to either side.

As discussed above, these measurements and the corresponding image captures may be collected as training data and provided to the neural network for analysis, with positions and orientations defined by the measurements being outputs of analysis of the image captures and image processing discussed above, with training feedback provided according to differences between a calculated position and orientation from the neural network and the corresponding training data position and orientation for the same image. Once enough training data has been gathered and iterations of training performed, the neural network may be used to suggest screw positions and orientations, given an image capture. The suggested position and orientation may be displayed as an overlay on the image capture, e.g. as a virtual pedicle screw, red line, or any other such element. The user may choose to accept the suggested position and orientation, or decline and select their own position and orientation; in the latter case, the selected position and orientation (as well as the actual installed position and orientation after surgery) may be provided to the neural network as training data for the image, refining and improving future suggestions.

Figure 26:
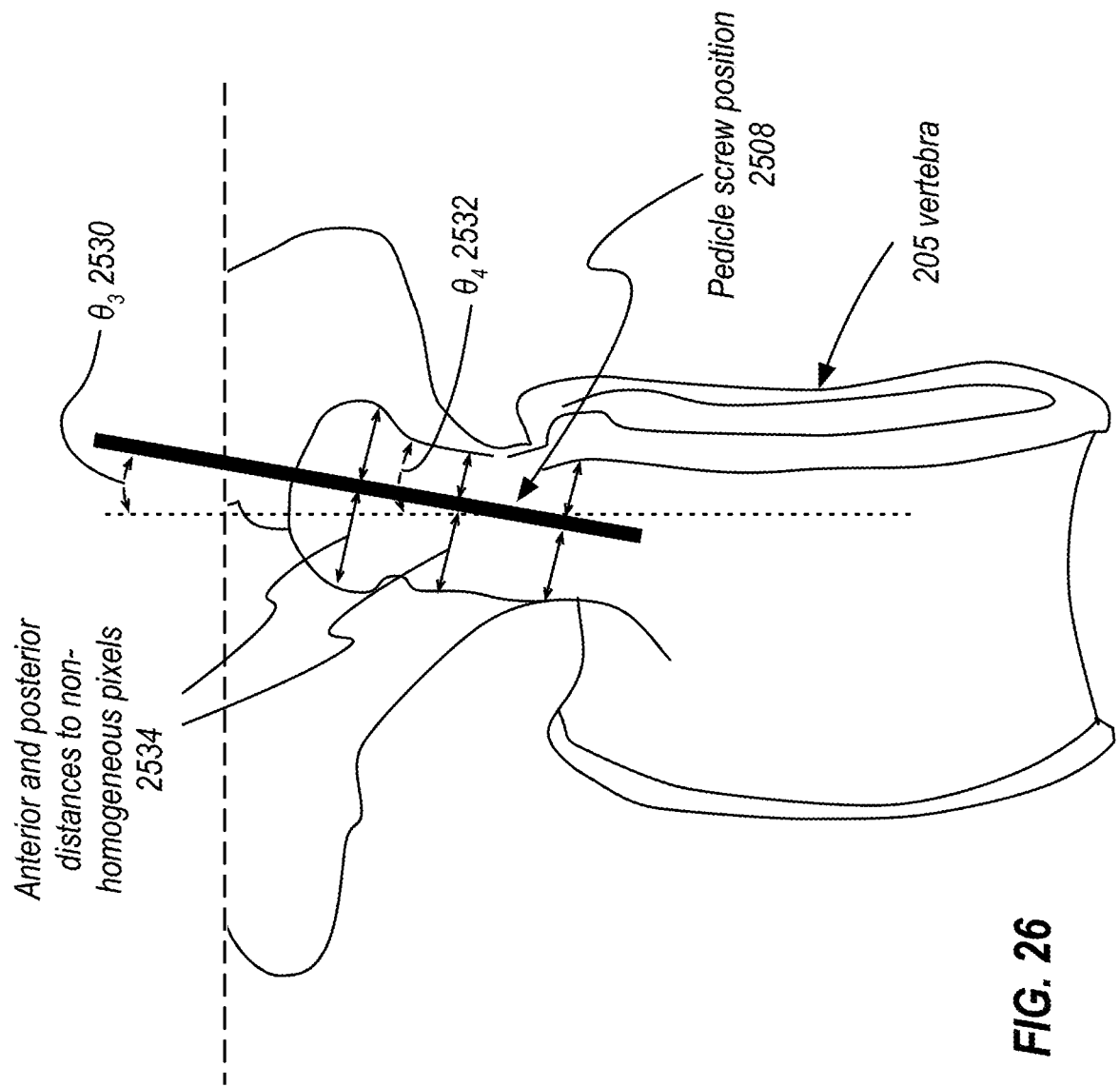
FIG. 26 is an illustration of another implementation of a process for processing captured images for calculating and determining placement of posterior fixation placement.

Although discussed above primarily in terms of axial images and two-dimensional orientations and placement, the systems and methods discussed herein may readily be applied to three-dimensional orientations and placement of medical devices, using a pair of orthogonal images (e.g. axial and lateral). FIG. 26 illustrates a lateral image of a vertebra 205, with a position of a medical device or pedicle screw 2508 illustrated as a black line overlay. As discussed above, image analysis may be performed on the lateral image in the same manner (e.g. identifying a largest area of homogeneity corresponding to the vertebral body; and identifying a pedicle as a second homogeneous region laterally adjacent to the identified largest area). One or more anterior and posterior measurements 2534 of the position of the screw relative to the pedicle body may be made, and angles of the medical device $\theta_3$ 2530 and pedicle body $\theta_4$ 2532 relative to a vertical axis (shown in dotted line) may be measured from the image or captured via position and orientation sensors of a device during installation as discussed above. The lateral image position and orientation measurements and image may be provided to the neural network as discussed above. In some implementations, the lateral and axial images (or other orthogonal images) may be provided separately to the neural network to generate corresponding lateral and axial placement and orientation suggestions; while in other implementations, both lateral and axial images (or other orthogonal images) may be provided to the neural network (e.g. as concatenated vectors after pre-processing or filtering as discussed above) with the network having outputs corresponding to the lateral, medial, anterior, posterior measurements and angle measurements. The outputs may be used to generate a virtual pedicle screw within a three-dimensional region defined by the combined axial and lateral images, which may be displayed as an overlay on the images (either in two dimensional views or in a three dimension virtual or augmented reality view).

Figure 27:
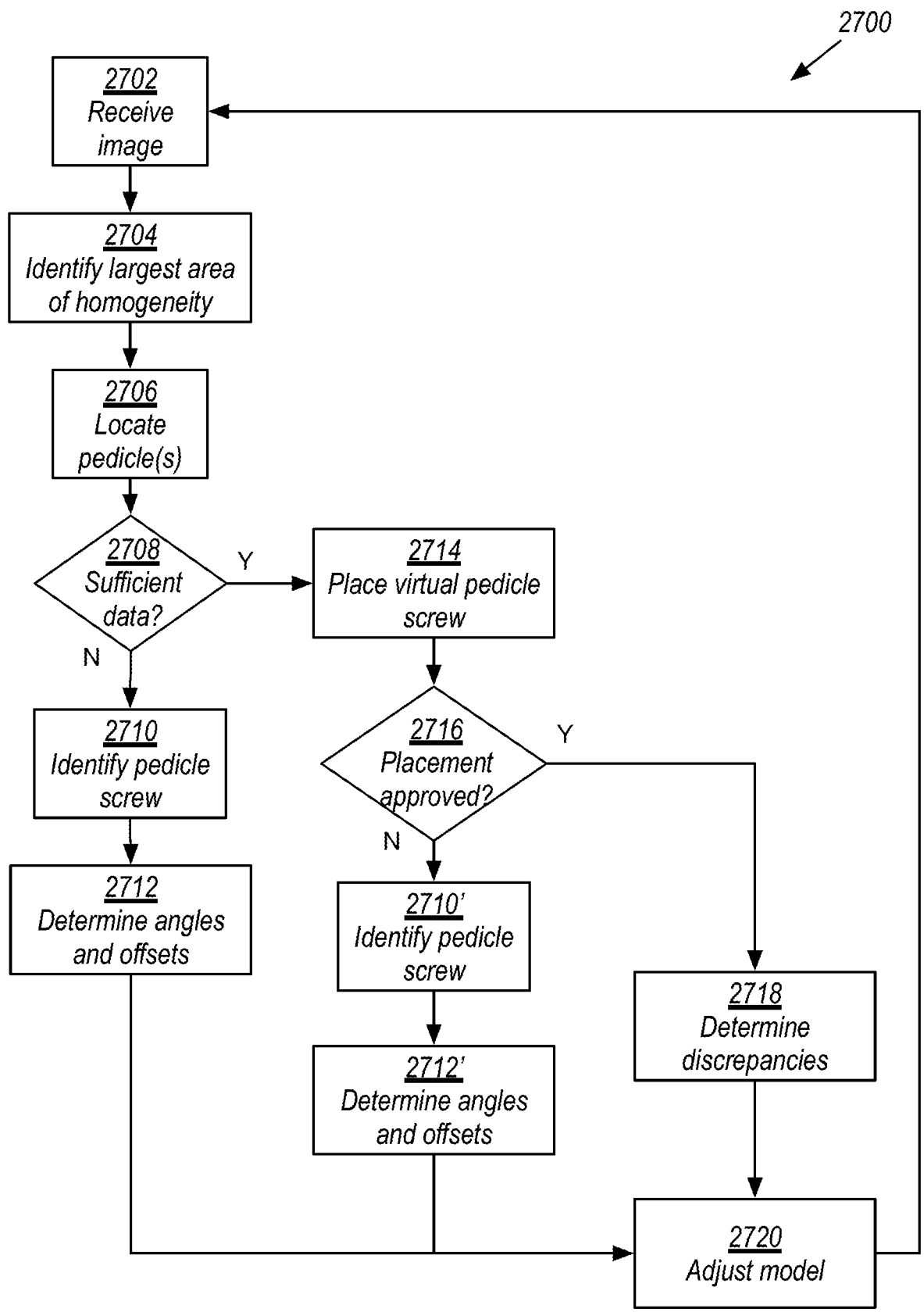
FIG. 27 is a flow chart of an implementation of a process for processing captured images for calculating and determining placement of posterior fixation placement.

FIG. 27 is a flow chart of an implementation of a method 2700 for processing captured images for calculating and determining optimal or desired placement of posterior fixation placement. In brief overview, at step 2702, a server or other computing device may receive an image. At step 2704, the computing device may identify a largest area of homogeneity in the image. At step 2706, the computing device may locate one or more pedicle bodies based on the identified largest area of homogeneity. If a neural network of the computing device has not been sufficiently trained or if the received image is associated with training data, then a screw position and orientation may be determined at step 2710, and at step 2712, angles and position offsets of the screw relative to the pedicle body may be measured. The measurements and image may be provided to the neural network at step 2720 for training. If the network has been sufficiently trained or if the received image is not associated with training data, then at step 2714, the neural network may process the image to identify a suggested position and orientation for the pedicle screw, and the computing device may provide an overlay to the image showing the suggested placement. If the placement is not approved, then at step 2710', the computing device may determine a new position or orientation selected by the user, measured during installation of the screw, or determined from image analysis after installation. At step 2712', the computing device may measure angles and position offsets of the screw relative to the pedicle. In some implementations, if the suggested placement is approved, then at step 2718, the computing device may determine discrepancies between the suggested placement and a subsequently measured or recorded actual placement of the screw, and at step 2720, may adjust or retrain the neural network model based on the image and measured actual angles and position offsets.

Still referring to FIG. 27 and in more detail, at step 2702, a server or other computing device may receive an image from an apparatus or other electronic device. The image may comprise a CT scan, X-ray, MM, or other such image, and may be received via any suitable means (e.g. via an attached storage device, such as a flash drive; via a network interface; etc.). The image may, in some implementations, be scaled to a predetermined size and/or have a resolution or bit-depth adjusted. In some implementations, a determination may be made as to a source of the image, e.g. based on metadata of the image, based on a bit-depth of the image corresponding to a bit-depth of a predetermined source, etc.

At step 2704, the computing device may identify a largest area of homogeneity in the image. In some implementations, the computing device may compare brightness or pixel values of adjacent pixels to identify contiguous regions having identical or similar pixels values, with the largest such region identified. In some implementations, the computing device may rescale pixel values or reduce a resolution and average pixel values of the image to reduce variations, may filter the image to reduce noise, or may perform other such pre-processing on the image. The area of largest homogeneity may correspond to a vertebral body, in some implementations.

At step 2706, the computing device may locate one or more pedicle bodies based on the identified largest area of homogeneity, in some implementations. The pedicle bodies may comprise additional homogeneous regions laterally adjacent to the identified largest area of homogeneity. In some implementations, the pedicle bodies may be defined by edge detection of borders in the image adjacent to a homogeneous region that is itself adjacent to the identified largest area of homogeneity. In some implementations, a portion of the image above the pedicle bodies may be cropped or removed to reduce processing requirements and limit analysis.

At step 2708, in some implementations, the computing device may determine whether a machine learning system or neural network has been sufficiently trained. In some implementations, the neural network may be considered sufficiently trained when a predetermined amount of training data has been analyzed and the output positions and orientations of the network are within a threshold range of the training data positions and orientations. In other implementations, step 2708 may be skipped, and suggestions may be provided for all input images that lack associated measurement data (e.g. from image analysis or sensor recordings); such suggestions may initially be poor, before the neural network is trained, but may improve over time.

In some other implementations, step 2708 may instead determine whether the received image is associated with measurement data for a position and orientation of a medical device that has already been installed—i.e. the image was captured after or during installation of the medical device. In some such instances, the image may include an image of the medical device, which may be identified via image analysis, and measurements made of position and orientation. In other such instances, the image may be associated with metadata of sensor values of orientation and position during installation of the device, as discussed above. If the image is associated with measurement data or contains an image of the medical device from which measurement data may be determined, then the image may be used as training data and the method may proceed to step 2710.

If a neural network of the computing device has not been sufficiently trained, or if the received image is associated with measurement data for training, then in some implementations at step 2710, a screw may be identified, and a position and orientation of the screw may be determined at step 2712. As discussed above, the screw position and orientation may be determined based on metadata included with the image, determined from sensor data received separately along with the image, determined from identification of an image of the screw within the received image and measurement of its position and orientation, etc.

The measurements and image may be provided to the neural network at step 2720 for training, and a model of the network (e.g. coefficients and/or weights, numbers of nodes or hidden layers, etc.) may be iteratively adjusted until the output of the neural network from the image is sufficiently close to the determined angles and offsets of the screw (e.g. with a correlation above a threshold value).

If the network has been sufficiently trained or if the image is not associated with measurement data, then at step 2714, the neural network may process the image to identify a suggested position and orientation for the pedicle screw, and the computing device may provide an overlay to the image showing the suggested placement. As discussed above, in many implementations, multiple images (e.g. orthogonal images) may be received at step 2702, and accordingly, steps 2704-2708 may be performed for each image. The images may be processed separately or together at step 2714 by the neural network, as discussed above, and the suggested placement of the pedicle screw may be determined for three dimensions. The overlay may be shown in orthogonal two-dimensional views (e.g. as overlays on each image) or rendered in three dimensions in virtual or augmented reality in many implementations.

In many implementations, a user interface may be provided to allow the user to accept the suggested position and orientation of the medical device, or to decline and/or adjust the position and orientation of the medical device. If the position is accepted, then the user may proceed with installation of the device, using the systems and methods discussed above.

If the placement is not approved or if it is modified, then at steps 2710' and 2712', the computing device may determine a new position or orientation of the medical device from the selection by the user, from sensor measurements or recordings during installation of the medical device, or determined from image analysis from a subsequent image captured after installation. The new position or orientation may be provided to the neural network at step 2720 for training or adjustment of the model, as discussed above.

In some implementations, if the placement is approved, the computing device may still receive or record sensor measurements during installation of the medical device and/or may identify an actual installed position of the medical device from image analysis from a subsequent image captured after installation, as discussed above, and at step 2718, may determine any discrepancies between the suggested position and orientation from step 2714 and the measured actual position and orientation. In some implementations, the actual position and orientation and may be provided as training data for the corresponding image to the neural network at step 2720. In some implementations, this may be performed for all installations, while in other implementations, this may be done only if the discrepancies exceed a threshold (to reduce processing requirements for retraining the model when the differences are negligible).

Accordingly, implementations of the systems and methods discussed herein provide for an artificial intelligence or machine learning-based image analysis and suggestion of placement of medical alignment devices, with supervised learning provided by users. A computing device may receive a target image captured via an image sensor; process the captured target image to identify anatomical features within the captured target image; calculate, via a trained neural network, a placement orientation and position of a virtual surgical appliance within the identified anatomical features; and render, on a display screen, the captured target image and the virtual surgical appliance at the calculated placement orientation and position.

In some implementations, software functionality or executable logic for execution by one or more processors of the system may be provided in any suitable format. For example, in some implementations, logic instructions may be provided as native executable code, as instructions for a compiler of the system, or in a package or container for deployment on a virtual computing system (e.g. a Docker container, a Kubernetes Engine (GKE) container, or any other type of deployable code). Containers may comprise standalone packages comprising all of the executable code necessary to run an application, including code for the application itself, code for system tools or libraries, preferences, settings, assets or resources, or other features. In many implementations, containers may be platform or operating system agnostic. In some implementations, a docker engine executed by a single host operating system and underlying hardware may execute a plurality of containerized applications, reducing resources necessary to provide the applications relative to virtual machines for each application (each of which may require a guest operating system).

Although the disclosure may reference one or more "users", such "users" may refer to user-associated devices or stations (STAs), for example, consistent with the terms "user" and "multi-user" typically used in the context of a multi-user multiple-input and multiple-output (MU-MIMO) environment.

Although examples of communications systems described above may include devices operating according to an 802.11 standard, it should be understood that embodiments of the systems and methods described can operate according to other standards and use wireless communications devices other than devices configured as devices and APs. For example, multiple-unit communication interfaces associated with cellular networks, satellite communications, vehicle communication networks, and other non-802.11 wireless networks can utilize the systems and methods described herein to achieve improved overall capacity and/or link quality without departing from the scope of the systems and methods described herein.

It should be noted that certain passages of this disclosure may reference terms such as "first" and "second" in connection with devices, mode of operation, transmit chains, antennas, etc., for purposes of identifying or differentiating one from another or from others. These terms are not intended to merely relate entities (e.g., a first device and a second device) temporally or according to a sequence, although in some cases, these entities may include such a relationship. Nor do these terms limit the number of possible entities (e.g., devices) that may operate within a system or environment.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a floppy disk, a hard disk, a CD-ROM, a flash memory card, a PROM, a RAM, a ROM, or a magnetic tape. In general, the computer-readable programs may be implemented in any programming language, such as LISP, PERL, C, C++, C#, PROLOG, Python, Nodejs, or in any byte code language such as JAVA. The software programs or executable instructions may be stored on or in one or more articles of manufacture as object code.

While the foregoing written description of the methods and systems enables one of ordinary skill to make and use what is considered presently to be the best mode thereof, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

What is claimed is:

1. A system for placement of surgical appliances, comprising:
    a plurality of orientation apparatuses configured to determine at least two axes of rotation of the system;
    one or more processors configured to:
        receive a target image captured via an image sensor,
        process the captured target image to identify anatomical features within the captured target image,
        calculate, via a trained neural network, a placement orientation and position of a virtual surgical appliance within the identified anatomical features corresponding with a first region of at least one region adjacent to a largest area of homogeneity within the captured target image, and wherein the calculation is based on a weighted average of historical placement orientations and positions of the virtual surgical appliance, wherein calculating the placement orientation and position of the virtual surgical appliance further comprises calculating a three-dimensional orientation and position of the virtual surgical appliance within a region defined by the target image and a second target image orthogonal to the target image,
        render on a display screen;
            the captured target image and the virtual surgical appliance at the calculated placement orientation and position, wherein the captured target image is rendered in three dimensions in virtual or augmented reality according to the three-dimensional orientation and position of the virtual surgical appliance, and
            at least a portion of a present orientation of the system and the virtual surgical appliance at the calculated orientation and position based on the determined at least two axes of rotation of the system, wherein the at least two axes is determined based on at least a first orientation apparatus of the plurality of orientation apparatuses and a second orientation apparatus of the plurality of orientation apparatuses.

2. The system of claim 1, wherein the one or more processors are further configured to measure a bit depth of the captured target image.

3. The system of claim 1, wherein the one or more processors are further configured to identify the largest area of homogeneity within the captured target image.

4. The system of claim 3, wherein the one or more processors are further configured to identify the at least one region adjacent to the identified largest area of homogeneity.

5. The system of claim 4, wherein the one or more processors are further configured to calculate the placement orientation and position of the virtual surgical appliance within the first region of the identified at least one region adjacent to the identified largest area of homogeneity.

6. The system of claim 1, wherein the one or more processors are further configured to:
    receive the second target image captured via a second image sensor, the second target image orthogonal to the target image, and
    process the captured second target image to identify anatomical features within the captured second target image.

7. The system of claim 1, further comprising a network interface configured to transmit the processed target image to a remote computing device executing the trained neural network; and wherein the one or more processors are further configured to receive, from the remote computing device, the calculated placement orientation and position of the virtual surgical appliance.

8. The system of claim 1, wherein the anatomical features within the captured target image comprise a portion of a vertebra or a pedicle, or any combination thereof, and wherein the virtual surgical appliance is a virtual pedicle screw.

9. A method for placement of surgical appliances, comprising:
    receiving, by a computing device, a target image captured via an image sensor;
    processing, by the computing device, the captured target image to identify anatomical features within the captured target image;
    calculating, by the computing device via a trained neural network, a placement orientation and position of a virtual surgical appliance within the identified anatomical features corresponding with a first region of at least one region adjacent to a largest area of homogeneity within the captured target image, and wherein the calculation is based on a weighted average of historical placement orientations and positions of the virtual surgical appliance, wherein calculating the placement orientation and position of the virtual surgical appliance further comprises calculating a three-dimensional orientation and position of the virtual surgical appliance within a region defined by the target image and a second target image orthogonal to the target image;
    rendering by the computing device on a display screen:
        the captured target image and the virtual surgical appliance at the calculated placement orientation and position, wherein the captured target image is rendered in three dimensions in virtual or augmented reality according to the three-dimensional orientation and position of the virtual surgical appliance; and
        at least a portion of a present orientation of an orientation calibration system and the virtual surgical appliance at the calculated orientation and position based on at least two axes of rotation of the orientation calibration system, wherein the at least two axes is determined based on at least a first orientation apparatus of a plurality of orientation apparatuses of the computing device and a second orientation apparatus of the plurality of orientation apparatuses.

10. The method of claim 9, wherein processing the captured target image further comprises measuring a bit depth of the captured target image.

11. The method of claim 9, wherein processing the captured target image further comprises identifying the largest area of homogeneity within the captured target image.

12. The method of claim 11, wherein processing the captured target image further comprises identifying the at least one region adjacent to the identified largest area of homogeneity.

13. The method of claim 12, further comprising calculating the placement orientation and position of the virtual surgical appliance within the first region of the identified at least one region adjacent to the identified largest area of homogeneity.

14. The method of claim 9, further comprising:
receiving, by the computing device, the second target image captured via a second image sensor, the second target image orthogonal to the target image, and
processing, by the computing device, the captured second target image to identify anatomical features within the captured second target image.

15. The method of claim 9, further comprising transmitting, via a network interface of the computing device, the processed target image to a remote computing device executing the trained neural network; and receiving, from the remote computing device, the calculated placement orientation and position of the virtual surgical appliance.

16. The method of claim 9, wherein the anatomical features within the captured target image comprise a portion of a vertebra and wherein the virtual surgical appliance is a virtual pedicle screw.

* * * * *